US008809629B2

(12) United States Patent
Forster et al.

(10) Patent No.: US 8,809,629 B2
(45) Date of Patent: Aug. 19, 2014

(54) MODIFICATION OF PLANT LIGNIN CONTENT

(75) Inventors: Richard L. Forster, Auckland (NZ); William H. Rottmann, Summerville, SC (US); Marie B. Connett, Canberra (AU); Paul Sanders, Auckland (NZ); Gary Zhang, Auckland (NZ); Sandra Joanne Fitzgerald, Auckland (NZ); Clare Eagleton, Auckland (NZ)

(73) Assignee: Arborgen Inc., Ridgeville, SC (US)

( * ) Notice: Subject to any disclaimer, the term of this patent is extended or adjusted under 35 U.S.C. 154(b) by 0 days.

(21) Appl. No.: 13/244,018

(22) Filed: Sep. 23, 2011

(65) Prior Publication Data

US 2013/0213592 A1 Aug. 22, 2013

Related U.S. Application Data

(62) Division of application No. 12/068,716, filed on Feb. 11, 2008, now Pat. No. 8,030,545, which is a division of application No. 10/946,650, filed on Sep. 22, 2004, now Pat. No. 7,402,428.

(51) Int. Cl.
*A01H 5/00* (2006.01)
*C12N 15/63* (2006.01)
*C12N 15/82* (2006.01)
*C12N 5/14* (2006.01)

(52) U.S. Cl.
USPC ........ 800/295; 800/285; 435/419; 435/320.1; 435/468

(58) Field of Classification Search
None
See application file for complete search history.

(56) References Cited

U.S. PATENT DOCUMENTS

| | | | |
|---|---|---|---|
| 5,491,090 A | 2/1996 | Handley, III et al. | |
| 5,506,136 A | 4/1996 | Becwar et al. | |
| 5,850,020 A | 12/1998 | Bloksberg et al. | |
| 5,856,191 A | 1/1999 | Handley, III | |
| 6,252,135 B1 | 6/2001 | Chiang et al. | |
| 6,380,459 B1 | 4/2002 | Perera et al. | |
| 6,410,718 B1 * | 6/2002 | Bloksberg et al. | 536/23.6 |
| 6,506,559 B1 | 1/2003 | Fire et al. | |
| 6,518,485 B1 | 2/2003 | Connett-Porceddu et al. | |
| 6,610,908 B1 | 8/2003 | Chapple | |
| 6,682,931 B2 | 1/2004 | Becwar et al. | |
| 2002/0078474 A1 | 6/2002 | Chiang et al. | |
| 2002/0100083 A1 | 7/2002 | Connett-Porceddu et al. | |
| 2002/0107644 A1 | 8/2002 | Meglen et al. | |
| 2002/0113212 A1 | 8/2002 | Meglen et al. | |
| 2003/0131373 A1 | 7/2003 | Bloksberg et al. | |
| 2004/0146904 A1 | 7/2004 | Phillips et al. | |
| 2004/0163146 A1 | 8/2004 | Phillips et al. | |
| 2006/0130183 A1 | 6/2006 | Forster et al. | |

FOREIGN PATENT DOCUMENTS

| | | |
|---|---|---|
| AU | 756359 | 10/2001 |
| EP | 0271988 B1 | 8/1995 |
| EP | 1050209 A2 | 11/2000 |
| JP | 2000-316403 | 11/2000 |
| JP | 2001-50038 | 1/2001 |
| JP | 2002-527058 | 8/2002 |
| JP | 2002-541764 | 12/2002 |
| JP | 2004-511216 | 4/2004 |
| JP | 2004-515224 | 5/2004 |
| JP | 2006-515509 | 6/2006 |
| WO | WO 98/11205 | 3/1998 |
| WO | WO 98/36083 | 8/1998 |
| WO | WO 99/10498 | 3/1999 |
| WO | WO 00/12715 A1 | 3/2000 |
| WO | WO 00/22099 | 4/2000 |
| WO | WO 00/36081 | 6/2000 |
| WO | WO 00/53724 A2 | 9/2000 |
| WO | WO 00/58489 | 10/2000 |
| WO | WO 01/98485 A1 | 12/2001 |
| WO | WO 02/20717 A2 | 3/2002 |
| WO | WO 03/040306 A2 | 5/2003 |
| WO | WO 2004/048595 A2 | 6/2004 |
| WO | WO 2006/036698 A2 | 4/2006 |

OTHER PUBLICATIONS

Levin et al. (Plant Molecular Biology, 44:759-775, 2000).*
The Notice of Reason for Rejetion, dated Aug. 24, 2011, received in the related Japanese Patent Application No. 2007-532667.
Blount, et al., "Altering Expression of Cinnamic Acid 4-Hydroxylase in Transgenic Plants Provides Evidence for a Feedback Loop at the Entry Point into the Phenylpropanoid Pathway", *Plant Physiol.*, (2000), 122, pp. 107-116.
Goujon, et al., "Genes involved in the biosynthesis of lignin precursors in *Arabidopsis thaliana*", *Plant Physiol. Biochem.*, (2003), 41, pp. 677-687.
Kawai, et al., "Isolation and Analysis of Cinnamic Acid 4-Hydroxylase Homologous Genes from a Hybrid Aspen, *Populus kitakamiensis*", *Biosci. Biotech. Biochem*, (1996), 60, No. 10, pp. 1586-1597.
"Development of new biological and applied researches of lignin biosynthesis", *Bioscience and Industry*, (2002), 60, No. 6, pp. 371-376.
Raes, et al., "Genome-Wide Characterization of the Lignification Toolbox in *Arabidopsis*", *Plant Physiol.*, (2003), 133, pp. 1051-1071.
Plant Physiol., vol. 131, 2003, pp. 1450-1459.
In vitro Cell. Dev. Biolg., vol. 34 (3Part2), 1998, p. 43A p. 1004.
Plant Cell, vol. 3, 1991, p. 435-443.
Notice of Reasons for Rejection received in the corresponding Japanese Patent Application No. 2007-532646, dated Aug. 29, 2011.

(Continued)

*Primary Examiner* — Vinod Kumar
(74) *Attorney, Agent, or Firm* — Foley & Lardner LLP

(57) ABSTRACT

DNA constructs comprising a first DNA segment that corresponds to at least a portion of a gene in the monolignol biosynthetic pathway, a spacer DNA segment, and a second DNA segment that is complementary to the first DNA segment can be used to reduce or modulate the lignin content in plants. In some embodiments, DNA constructs comprise at least a portion of a gene for 4CL, C3H, CCR, C4H or CCoAOMT. Vascular-preferred and constitutive promoters can be used to drive expression of the constructs.

7 Claims, 16 Drawing Sheets

(56) References Cited

OTHER PUBLICATIONS

The Office Action received in the parent U.S. Appl. No. 12/898,491, dated Dec. 1, 2012.

Blee, et al., "Antisense and sense expression of cDNA coding for CYP73A15, a class II cinnamate 4-hydroxylase, leads to a delayed and reduced production of lignin in tobacco", *Phytochemistry*, vol. 57, 2001, pp. 1159-1166.

The European Search Report received in the related European Patent Application No. 10180404.5, dated Jul. 19, 2011.

Chen, et al., "Plant production of transgenic *Eucalyptus camaldulensis* carrying the *Populus tremuloides* cinnamate 4-hydroxylase gene", *Taiwan Journal of Forest Science*, vol. 16, No. 4, 2001, pp. 249-258.

Kawai, et al., "Isolation and analysis of cinnamic acid 4-hydroxylase homologous genes from a hybrid aspen, *Populus kitakamiensis*", *Bioscience Biotechnology and Biochemistry*, vol. 60, No. 10, 1996, pp. 1586-1597.

Vanholme, et al., "Lignin engineering", *Plant Biology*, vol. 11, No. 3, 2008, pp. 278-285.

The English Translation of the Notice of the Reasons for Rejection received in the related Japanese Patent Application No. 2007-532646, dated Aug. 27, 2012.

Franke, et al., "Modified lignin in tobacco and polar plants over-expressing the *Arabidopsis* gene encoding ferulate 5-hydroxylase", *The Plant Journal*, 2000, 22(3), pp. 223-234.

Haufie, et al., "A Parsley 4CL-1 promoter fragment specifies complex expression patterns in transgenic tobacco", *The Plant Cell*, 1991, 3, pp. 435-443.

Higuchi, et al., "Pathways for monolignol biosynthesis via metabolic grids: coniferyl aldehyde 5-hydroxylase, a possible key enzyme in angiosperm syringyl lignin biosynthesis", *Proc. Japan Acad.*, 2003, 79, Ser. B.

The Pre-Appeal Examination Report, received in the related Japanese Patent Application No. 2007-532636—Appeal No. 2012-025606, dated Feb. 15, 2013.

Chen, et al., "Plant Production of Transgenic *Eucalyptus* . . . ", *Taiwan Journal of Forest Science*, vol. 16, No. 4, 2001, pp. 249-258.

Moralejo, et al., "Generation of transgenic *Eucalyptus globulus* . . . ", *Aust. J. Plant Physiol.*, vol. 25, pp. 207-212.

Fire et al., "Potent and specific genetic interference by double-stranded RNA in *Caenorhabditis elegans*," Nature, vol. 391, Feb. 19, 1998, pp. 806-811.

Carthew et al., (Current Opinion in Cell Biology, 13:244-248, 2001).

Arziman et al., (Nucleic Acids Research, 33: 582-588, 2005).

Levin et al., (Plant Molecular Biology, 44: 759-775, 2000).

Smith et al., (Nature, 407: 319-320, Sep. 2000).

Abbott et al., "Simultaneous Suppression of Multiple Genes by Single Transgenes. Down-Regulation of Three Unrelated Lignin Biosynthetic Genes in Tobacco," Plant Physiol., Mar. 2002, pp. 844-853, vol. 128(3).

Aharoni et al., "Novel Insight into Vascular, Stress, and Auxin-Dependent and -Independent Gene Expression Programs in Strawberry, a Non-Climacteric Fruit," Plant Physiol., Jul. 2002, pp. 1019-1031, vol. 129.

Anterola et al., "Trends in lignin modification: a comprehensive analysis of the effects of genecit manipulations/mutations on lignification and vascular integrity," Phytochemistry, 2002, pp. 221-294, vol. 61.

Baucher et al., "Lignin: Genetic Engineering and Impact on Pulping," Crit. Rev. Biochem. Mol. Biol., 2003, pp. 305-350, vol. 38(4).

Boerjan et al., "Lignin Biosynthesis," Ann. Rev. Plant Biol., 2003, pp. 519-546, vol. 54.

Boudet et al., "Tansley review No. 80 Biochemistry and molecular biology of lignification," New Phytol., 1995, pp. 203-236, vol. 129.

Campbell et al., "Fungal Elicitor-Mediated Responses in Pine Cell Cultures," Plant Physiol., 1992, pp. 62-70, vol. 98.

Chang et al., "A Simple and Efficient Method for Isolating RNA from Pine trees," Plant Molecular Biology Reporter, 1993, pp. 113-116, vol. 11, No. 2.

Chapple et al., "An *Arabidopsis* Mutant Defective in the General Phenylpropanoid Pathway," Plant Cell., Nov. 1992, pp. 1413-1424, vol. 4(11).

Cheng et al., "*Agrobacterium*-transformed rice plants expressing synthetic *cryIA(b)* and *cryIA(c)* genes are highly toxic to striped stem borer and yellow stem borer," Proc. Natl. Acad. Sci. USA, Mar. 1998, pp. 2767-2772, vol. 95.

Cheng et al., "Genetic Transformation of Wheat Mediated by *Agrobacterium tumefaciens*," Plant Physiol., 1997, pp. 971-980, vol. 115.

Cheong et al., "Transcriptional Profiling Reveals Novel Interactions between Wounding, Pathogen, Abiotic Stress, and Hormonal Responses in *Arabidopsis*," Plant Physiol., Jun. 2002, pp. 661-677, vol. 129.

Christensen et al., "The syringaldazine-oxidizing peroxidase PXP 3-4 from poplar xylem: cDNA isolation, characterization and expression," Plant Mol. Biol., 2001, pp. 581-593, vol. 47.

Dean et al., "Forest Tree Biotechnology," Adv. Biochem. Eng. Biotechnol., 1997, pp. 1-44, vol. 57.

Dean et al., "Laccases Associated with Lignifying Vascular Tissues, In Lignin and Lignan Biosynthesis," ACS Symposium Series, American Chemical Society, Washington, DC, 1998, pp. 96-108, vol. 697.

Delbreil et al., "*Agrobacterium*-mediated transformation of *Asparagus officinalis* L. long-term embryogenic callus and regeneration of transgenic plants," Plant Cell Reports, 1993, pp. 129-132, vol. 12.

Dixon et al., "Changes in the levels of enzymes of phenylpropanold and flavonoid synthesis during phaseollin production in cell suspension cultures of *Phaseolus vulgaris*," Physiol. Plant Pathol., 1978, pp. 295-306, vol. 13.

Effland et al., "Modified procedure to determine acid-insoluble lignin in wood and pulp," T.A.P.P.I., 1977, pp. 143-144, vol. 60(10).

Elbashir et al., "RNA interference is mediated by 21- and 22-nucleotide RNAs," Genes & Development, 2001, pp. 188-200, vol. 15.

Elkind et al., "Abnormal plant development and down-regulation of phenylpropanoid biosynthesis in transgenic tobacco containing a heterologous phenylalanine ammonia-lyase gene," Proc. Natl. Acad. Sci. U.S.A., Nov. 1990, pp. 9057-9061, vol. 87.

Enríquez-Obregón et al., "Herbicide-resistant sugarcane (*Saccharum officinarum* L.) plants by *Agrobacterium*-mediated transformation," Plants, 1998, pp. 20-27, vol. 206.

Evans et al., "Molecular Characterization of the Pyrolysis of Biomass. 1. Fundamentals," Energy & Fuels, Mar.-Apr. 1987, pp. 123-137, vol. 1(2).

Fukuda et al., "Lignin synthesis and its related enzymes as markers of tracheary-element differentiation in single cells isolated from the mesophyll of *Zinnia elegans*," Planta, 1982, pp. 423-430, vol. 155.

Fukushima et al., "Extraction and Isolation of Lignig for Utilization as a Standard to Determine Lignin Concentration Using the Acetyl Bromide Spectrophotometric Method," Journal of Agricultural and Food Chemistry, Jul. 2001, pp. 3133-3139, vol. 49, No. 7.

Gleave et al., "A versatile binary vector system with a T-DNA organizational structure conducive to efficient integration of cloned DNA into the plant genome," Plant Mol. Biol., 1992, pp. 1203-1207, vol. 20.

Goujon et al., "Down-regulation of the AtCCR1 gene in *Arabidopsis thaliana*: effects on phenotype, lignins and cell wall degradability," Planta, 2003, pp. 218-228, vol. 217.

Halpin et al., "Manipulation of lignin quality by downregulation of cinnamyl alcohol dehydrogenase," Plant J., 1994, pp. 339-350, vol. 6(3).

Hatfield et al., "Lignin Formation in Plants. The Dilemma of Linkage specificity," Plant Physiol., Aug. 2001, pp. 1351-1357, vol. 126.

Hauffe et al., "Combinatorial interactions between positive and negative *cis*-acting elements control spatial patterns of *4CL-1* expression in transgenic tobacco," The Plant Journal, 1993, pp. 235-253, vol. 4, No. 2.

Hiei et al., "Transformation of rice mediated by *Agrobacterium tumefaciens*," Plant Molecular Biology, 1997, pp. 205-218, vol. 35.

Hosokawa et al., "Progress of Lignification Mediated byIntercellular Transportation of Monolignols During Tracheary Element Differentiation of Isolated *Zinnia* Mesophyll Cells," Plant Cell Physiol., 2001, pp. 959-968, vol. 42(9).

(56) References Cited

OTHER PUBLICATIONS

Hu et al., "Repression of lignin biosynthesis promotes cellulose accumulation and growth in transgenic trees," Nature Biotechnol., Aug. 1999, pp. 808-812, vol. 17.
Humphreys et al., "Rewriting the lignin roadmap," Curr. Opin. Plant Biol., 2002, pp. 224-229, vol. 5(3).
Huntley et al., "Significant Increases in Pulping Efficiency in C4H-F5H-Transformed Poplars: Improved Chemical Savings and Reduced Environmental Toxins," J. Agric. Food Chem., 2003, pp. 6178-6183, vol. 51(21).
Ishida et al., "High efficiency transformation of maize (Zea mays L.) mediated by Agrobacterium tumefaciens," Nature Biotechnology, Jun. 1996, pp. 745-750, vol. 14.
Jefferson et al., "GUS-fusions: β-glucuronidase as a sensitive and versatile gene fusion marker in higher plants," The EMBO Journal, 1987, pp. 3901-3907, vol. 6, No. 13.
Kawaoka et al., "Functional analysis of tobacco LIM protein Ntlin1 involved in lignin biosynthesis," The Plant Journal, 2000, pp. 289-301, vol. 22, No. 4.
Kawaoka et al., "Transcriptional control of lignin biosynthesis by tobacco LIM protein," Phytochemistry, 2001, pp. 1149-1157, vol. 57.
Kozlowski and Pallardy ($2^{nd}$ eds.), "Physiology of Woody Plants," Academic Press, San Diego, CA, 1997, Title and Index pages.
Lagrimini et al., "Characterization of Antisense Transformed Plants Deficient in the Tobacco anionic Peroxidase," Plant Physiol., 1997, pp. 1187-1196, vol. 114.
Lapierre et al., "Structural Alterations of Lignins in Transgenic Poplars with Depressed Cinnamyl Alcohol Dehydrogenase or Caffeic Acid O-Methyltransferase Activity have an Opposite Impact on the Efficiency of Industrial Kraft Pulping," Plant Physiol., Jan. 1999, pp. 153-163, vol. 119.
Leple et al., "Transgenic poplars: expression of chimeric genes using four different constructs," Plant Cell Reports, 1992, pp. 137-141, vol. 11.
Li et al., "A new method for the analysis of phenolic groups in lignins by $^1$H NMR spectrometry," Nordic Pulp and Paper Research Journal, 1994, No. 3, pp. 191-195.
Liyama et al., "An improved acetyl bromide procedure for determining lignin in woods and wood pulps," Wood Sci. Technol., 1988, pp. 271-280, vol. 22.
Lu et al., "Derivatization Followed by Reductive Cleavage (DFRC Method), a New Method for Lignin Analysis: Protocol for analysis of DFRC Monomers," J. Agric. Food Chem., 1997, pp. 2590-2592, vol. 45.
Magrini et al., "Use of pyrolysis molecular beam mass spectrometry (py-MBMS) to characterize forest soil carbon: method and preliminary results," Environmental Pollution, 2002, pp. 5255-5268, vol. 116.
Maher et al., "Increased disease susceptibility of transgenic tobacco plants with suppressed levels of preformed phenylpropanoid products," Proc. Natl. Acad. Sci. U.S.A., Aug. 1994, pp. 7802-7806, vol. 91.
Marita et al., "NMR characterization of lignins from transgenic poplars with suppressed caffeic acid O-methyltransferase activity," J. Chem. Soc., Perkin Trans. I, 2001, pp. 2939-2945.
Marita et al., "NMR characterization of lignins in Arabidopsis altered in the activity of ferulate 5-hydroxylase," Proc. Natl. Acad. Sci. U.S.A., Oct. 26, 1999, pp. 12328-12332, vol. 96(22).
May et al., "Generation of Transgenic Banana (Musa acuminata) Plants via Agrobacterium-Mediated Transformation," Biotechnology, May 13, 1995, pp. 486-492, vol. 13.
McDougall et al., "Cell-wall-bound oxidases from tobacco (Nicotiana tabacum) xylem participate in lignin formation," Planta, 1994, pp. 9-14, vol. 194.
Norris et al., "The intron of Arabidopsis thaliana polyubiquitin genes is conserved in location and is a quantitative determinant of chimeric gene expression," Plant Molecular Biology, 1993, pp. 895-906, vol. 21.

Osakabe et al., "Coniferyl aldehyde 5-hydroxylation and methylation direct syringyl lignin biosynthesis in angiosperms," Proc Natl Acad Sci U.S.A., Aug. 1999, pp. 8955-8960, vol. 96(16).
Pilate et al., "Field and pulping performances of transgenic trees with altered lignification," Nature Biotechnol., Jun. 2002, pp. 607-612, vol. 20.
Ralph et al., "Abnormal Lignin in a Loblolly Pine Mutant," Science, Jul. 11, 1997, pp. 235-239, vol. 277.
Ranocha et al., "Laccase Down-Regulation Causes Alterations in Phenolic Metabolism and Cell Wall Structure in Poplar," Plant Physiol., May 2002, pp. 145-155, vol. 129.
Schenk et al., "Coordinated plant defense responses in Arabidopsis revealed by microarray analysis," Proc. Nat'l Acad. Sci., Oct. 10, 2000, pp. 11655-11660, vol. 97.
Sederoff et al., "Unexpected variation in lignin," Curr. Opin. Plant Biol., 1999, pp. 145-152, vol. 2.
Sederoff, R.R., "Building better trees with antisense," Nature Biotechnol., Aug. 17, 1999, pp. 750-751, vol. 17.
Sewalt et al., "Reduced Lignin Content and Altered Lignin Composition in Transgenic tobacco Down-Regulated in Expression of $_L$-Phenylalanine Ammonia-Lyase or Cinnamate 4-Hydroxylase," Plant Physiol., 1997, pp. 41-50, vol. 115.
Smith et al., "Antisense RNA inhibition of polygalacturonase gene expression in transgenic tomatoes," Nature, Aug. 25, 1988, pp. 724-726, vol. 334.
Smith et. al., "Inheritance and effect on ripening of antisense polygalacturonase genes in transgenic tomatoes," Plant Mol. Biol., 1990, pp. 369-379, vol. 14.
Sun et al., "Independent modulation of Arabidopsis thaliana polyubiquitin mRNAs in different organs and in response to environmental changes," Plant J., 1997, pp. 101-111, vol. 11.
Suzuki et al., "Production of transgenic plants of the Liliaceous ornamental plant Agapanthus praecox ssp. Orientalis (Leighton) Leighton via Agrobacterium-mediated transformation of embryogenic calli," Plant Science, 2001, pp. 89-97, vol. 161.
Thibaud-Nissen et al., "Clustering of Microarray Data Reveals Transcript Patterns Associated with Somatic Embryogenesis in Soybean," Plant Physiol., May 2003, pp. 118-136, vol. 132.
Tingay et al., "Agrobacterium tumefaciens-mediated barley transformation," The Plant Journal, 1997, pp. 1369-1376, vol. 11, No. 6.
Tournier et al., "An efficient procedure to stably introduce genes into an economically important pulp tree (Eucalyptus grandix x Eucalyptus urophylla)," Transgenic Research, 2003, pp. 403-411, vol. 12.
Wenck et al., "High-efficiency Agrobacterium-mediated transformation of Norway spruce (Picea abies) and loblolly pine (Pinus taeda)," Plant Molecular Biology, 1999, pp. 407-416, vol. 39.
Wesley et al., "Construct design for efficient, effective and high-throughput gene silencing in plants," Plant J., 2001, pp. 581-590, vol. 27.
Whetten et al., "Functional genomics and cell wall biosynthesis in loblolly pine," Plant Mol. Biol., 2001, pp. 275-291, vol. 47.
Ye et al., "Determination of S2-fibril-angle and fiber-wall thickness by microscopic transmission ellipsometry," Tappi J., 1997, pp. 181-190, vol. 80(6).
Zhong et al., "Essential Role of Caffeoyl Coenzyme A O-Methyltransferase in Lignin Biosynthesis in Woody Poplar Plants," Plant Physiol., Oct. 2000, pp. 536-577, vol. 124.
The Supplemental European Search Report of the related EP application No. EP 05 79 9768, dated Dec. 14, 2009.
Fukushima, Kazuhiko, "Regulation of syringyl to guaiacyl ratio in lignin biosynthesis", Journal of Plant Research, vol. 114, No. 1116, 2001, pp. 499-508.
Lee et al., "Antisense suppression of 4-coumarate:coenzyme A ligase activity in Arabidopsis leads to altered lignin subunit composition," Plant Cell., vol. 9 , No. 11, 1997, pp. 1985-1998.
Li et al., "Combinatorial modification of multiple lignin traits in trees through multigene cotransformation," Proc Natl Acad Sci U S A, vol. 100, No. 8, 2003, pp. 4939-4944.
Wagner et al., "Suppression of 4-Coumarate-CoA Ligase in the Coniferous Gymnosperm Pinus radiate", Plant Physiology, vol. 149, No. 1, 2009, pp. 370-383.

(56) References Cited

OTHER PUBLICATIONS

The English Translation of the Notice of Reasons for Rejection received in the corresponding Japanese Patent Application No. 2007-532646, dated Jul. 5, 2010.
The English Translation of the Notice of Reasons for Rejection received in the corresponding Japanese Patent Application No. 2007-532667, dated Jul. 5, 2010.

Voo et al., "4-Coumarate: Coenzyme A Ligase from Loblolly Pine Xylem", *Plant Physiol.*, vol. 108, 1995, pp. 85-97.

Anterola et al., "Transcriptional Control of Monolignol Biosynthesis in *Pinus taeda*", The Journal of Biological Chemistry, vol. 277, 2002, pp. 18272-18280.

\* cited by examiner

Figure 3
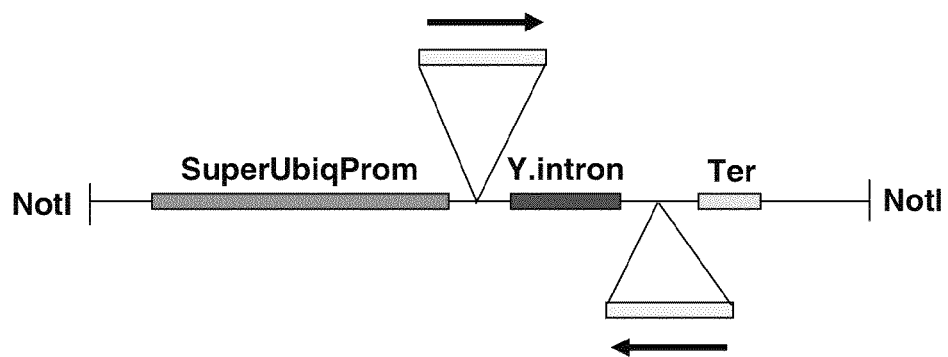
This shows the general design used for RNAi cconstruts using the SuperUbiquitin promoter
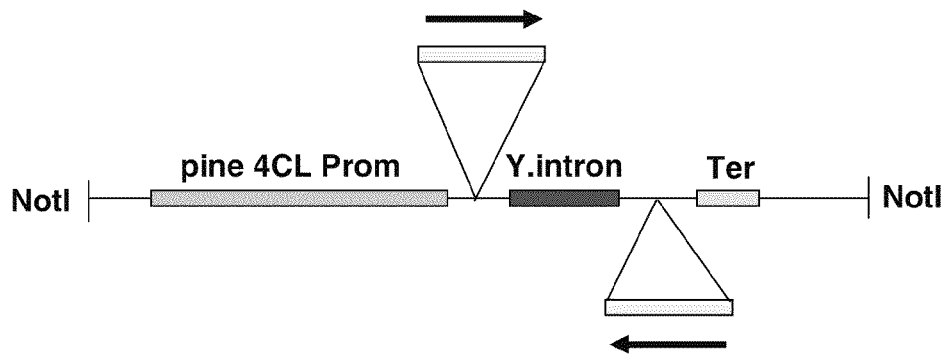
This shows the general design used for RNAi cconstruts using the pine 4CL promoter

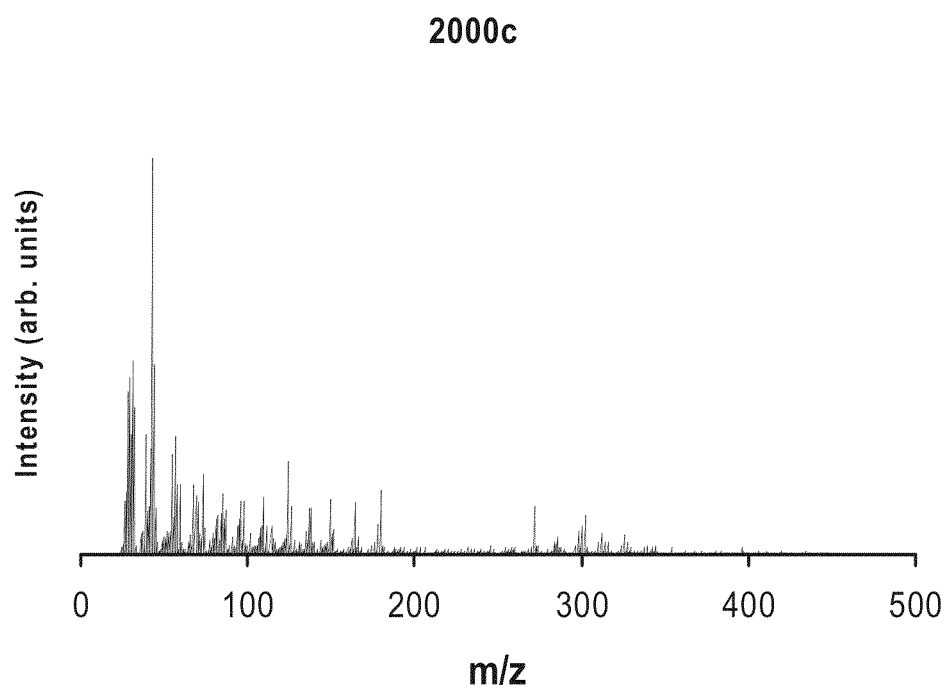
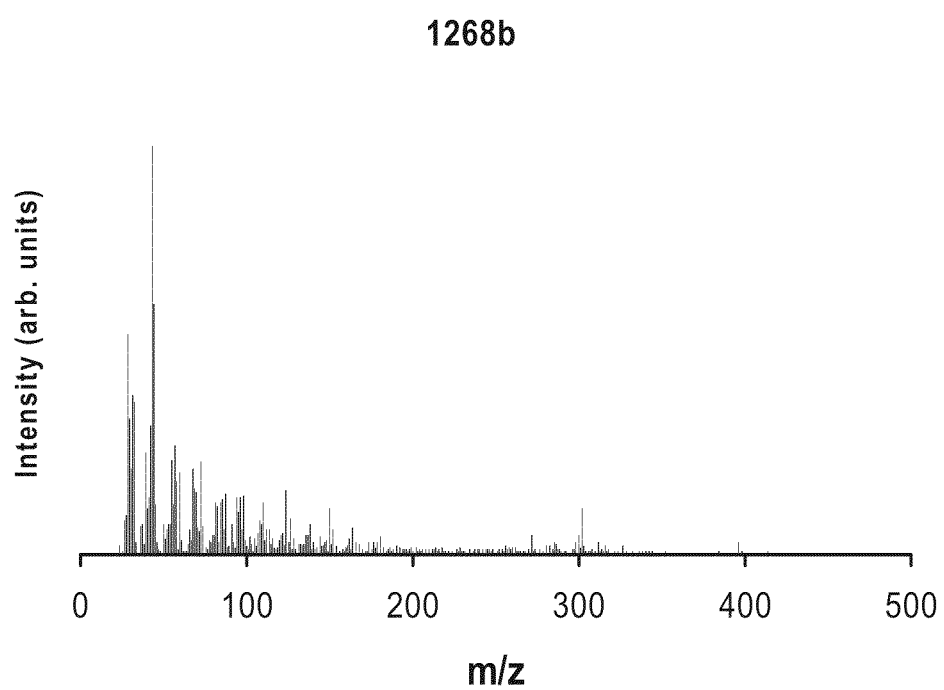
Figure 10. Representative mass spectra of loblolly pine samples. 2000c=control, 1268b = transgenic tree comprising the DNA construct pARB585

MODIFICATION OF PLANT LIGNIN CONTENT

CROSS-REFERENCE TO RELATED APPLICATION

This application is a divisional application of U.S. patent application Ser. No. 12/068,716, filed Feb. 11, 2008, which is a divisional application of U.S. patent application Ser. No. 10/946,650, filed on Sep. 22, 2004, now U.S. Pat. No. 7,402,428, all of which are hereby incorporated herein by reference.

FIELD OF INVENTION

The invention relates to genetically modifying plants, especially trees, through manipulation of the lignin biosynthesis pathway, and more particularly, to genetically modifying plants through the down regulation of 4CL, C3H, CCR, C4H or CCoAOMT to achieve altered lignin content.

BACKGROUND OF THE INVENTION

Lignin, a complex phenolic polymer, is a major component in cell walls of secondary xylem. In general, lignin constitutes 25% of the dry weight of the wood, making it the second most abundant organic compound on earth after cellulose. Although lignin contributes to the strength and rigidity of the stem, and protects microfibrils from physical, chemical and biological attack, it hinders the process of converting wood into paper. In order to liberate wood fibers for the production of paper, most of the lignin must be removed from the processed wood chips. Extracting lignin from wood fibers is a difficult and expensive process, involving harsh chemicals and yielding toxic waste products.

Consequently, practitioners have searched for more cost-effective and environmentally-friendly methods of reducing the lignin content in wood products. One alternative involves genetically modifying the biosynthetic pathway of lignin. For example, Chiang et al. have attempted to reduce the lignin content in a plant by genetically modifying the plant's monolignol biosynthetic pathway. See WO 02/20717. The method involved transforming a plant with multiple genes from the phenylpropanoid pathway, including key lignin control sites in the monolignol biosynthetic pathway such as the enzymes 4-coumarate-CoA ligase (4CL), coniferyl aldehyde 5-hydroxylase (CALD5H), S-adenosyl-L-methionine (SAM)-dependent 5-hydroxyconiferaldehyde, O-methyltransferase (AldOMT), coniferyl alcohol dehydrogenase (CAD) and sinewy alcohol dehydrogenase (SAD). Meanwhile, others have attempted to reduce lignin content by individually introducing copies of these genes into plant genomes. See e.g. WO 00/58489 (Scald); WO 99/24561 (4CL). Practitioners also have employed these genes in antisense strategies to modulate lignin biosynthesis. See e.g. WO 99/24561. While some of these methods successfully down-regulated lignin synthesis, the down-regulation of lignin can be detrimental to plant phenotype. Anterola et al., *Phytochemistry*, 61:221-294 (2002). Thus, improved methods for modulating lignin expression are needed.

A recent method of silencing gene expression at the mRNA level has emerged as a powerful alternative to prior technologies. RNA interference (RNAi) is a post-transcriptional process triggered by the introduction of double-stranded RNA (dsRNA) which leads to gene silencing in a sequence-specific manner. The initial discovery of RNA interference in *C. elegans* (Fire et al., *Nature*, 391:806-811 (1998) and U.S. Pat. No. 6,506,559) has been followed by numerous examples of organisms where introduction of dsRNA can induce the sequence-specific silencing effect. For example, RNAi has been reported to occur naturally in organisms as diverse as nematodes, trypanosmes, plants, fungi and animals. In nature, RNAi most likely serves to protect organisms from viruses, modulate transposon activity and eliminate aberrant transcription products.

Studies in the fruit fly *Drosophila melanogaster* suggest that RNAi is a two-step mechanism (Elbashir et al., *Genes Dev.*, 15(2): 188-200 (2001)). First, long dsRNAs are cleaved by an enzyme known as Dicer into 21-23 ribonucleotide (nt) fragments, called small interfering RNAs (siRNAs). Then, siRNAs associate with a ribonuclease complex (termed RISC for RNA Induced Silencing Complex) which target this complex to complementary mRNAs. RISC then cleaves the targeted mRNAs opposite the complementary siRNA, which makes the mRNA susceptible to other RNA degradation pathways.

RNAi may offer an alternative to prior methods of controlling lignin synthesis. Before the potential can be realized, however, DNA constructs that can initiate RNAi processes in the context of lignin synthesis must be developed.

SUMMARY

In one embodiment, DNA constructs useful for modulating the expression of lignin-related genes are provided. In another embodiment, methods of modulating the expression lignin in plants are provided. In addition, recombinant plants are produced that comprise DNA constructs useful for modulating the expression of lignin-related genes.

In one embodiment, a DNA construct comprises a promoter operably linked to a first DNA segment that corresponds to at least a portion of a gene in the monolignol biosynthetic pathway, a spacer DNA segment, and a second DNA segment that is complementary to the first DNA segment, wherein the first and second DNA segments are arranged in a 5' to 3' direction, respectively, in the DNA construct. In some embodiments, a gene in the monolignol biosynthetic pathway is selected from the group consisting of 4CL, C3H, CCR, C4H and CCoAOMT.

In another embodiment, a DNA construct comprises a promoter operably linked to a first DNA segment that corresponds to at least a portion of a 4-coumarate co-enzyme A ligase (4CL) gene, a spacer DNA segment, and a second DNA segment that is complementary to the first DNA segment, wherein the first and second DNA segments are arranged in a 5' to 3' direction, respectively, in the DNA construct. Methods of modulating, inhibiting and/or reducing the expression of lignin in a plant comprising the use of such constructs also are provided.

In yet another embodiment, a method of inhibiting the expression of lignin in a plant cell comprises integrating into said plant cell's genome a construct comprising, in a 5' to 3' direction, a promoter, a first DNA segment that corresponds to at least a portion of a 4CL gene, a spacer DNA segment and a second DNA segment that is complementary to the first DNA segment and growing said plant cell. Plants and plant cells produced by such processes also are provided, as are paper and wood products derived there from. Pulp and pulp-derived products derived from such transgenic plants also are provided. In another aspect, solid wood products derived from such transgenic plants are provided. The wood products include, for example, timber, lumber and composite.

In still another embodiment, plant cells are produced that comprise in a 5' to 3' direction, a promoter, a first DNA segment that corresponds to at least a portion of a 4CL gene, a spacer DNA segment and a second DNA segment that is complementary to the first DNA segment. The promoter, which is operably linked to the first DNA segment, can be endogenous or exogenous to the plant cell's genome. In other embodiments, plant cells are produced wherein the first DNA segment corresponds to at least a portion of a C3H, C4H, CCR or CCoAOMT gene.

In plants, a LIM protein has been demonstrated to control a number of genes in the lignin biosynthesis pathway, critically important for developing wood (Kawaoka A, Ebinuma H 2001 Transcriptional control of lignin biosynthesis by tobacco LIM protein. *Phytochemistry* 57:1149-1157, Kawaoka et al. *Plant J.* 22: 289-301 (2000). Thus, in still another embodiment, plant cells are produced that comprise in a 5' to 3' direction, a promoter, a first DNA segment that corresponds to at least a portion of a LIM gene, a spacer DNA segment and a second DNA segment that is complementary to the first DNA segment.

In another embodiment, a method of making wood involves integrating into a plant cell's genome a DNA construct comprising, in a 5' to 3' direction, a promoter, a first DNA segment that corresponds to at least a portion of a gene in the monolignol biosynthetic pathway, a spacer DNA segment and a second DNA segment that is complementary to the first DNA segment, growing said plant cell and obtaining said wood.

In another aspect, a method of making wood pulp involves integrating into a plant cell's genome a DNA construct comprising, in a 5' to 3' direction, a promoter, a first DNA segment that corresponds to at least a portion of a gene in the monolignol biosynthetic pathway, a spacer DNA segment and a second DNA segment that is complementary to the first DNA segment, growing said plant cell and obtaining said wood pulp.

In yet another embodiment, a method of making paper involves integrating into a plant cell's genome a DNA construct comprising, in a 5' to 3' direction, a promoter, a first DNA segment that corresponds to at least a portion of a gene in the monolignol biosynthetic pathway, a spacer DNA segment and a second DNA segment that is complementary to the first DNA segment, growing said plant cell and obtaining said paper.

Other objects, features and advantages of the present invention will become apparent from the following detailed description. The detailed description and specific examples, while indicating preferred embodiments, are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

BRIEF DESCRIPTION OF THE DRAWINGS

FIG. 2A provides a bar chart showing the resulting heights of transgenic *Eucalyptus* trees, while

FIG. 3 provides two diagrams of the inventive DNA constructs. The upper diagram shows the general design for an inverted repeat of the gene of interest driven by the SuperUbiq promoter. The inverter repeat comprises a from the yabby gene (SEQ ID NO: 64) and the same segment of the gene of interest in the opposite orientation (back arrow). A transcrip-tional terminator completes the construct. The lower diagram shows the general design for an inverted repeat of the gene of interest driven by the Pine 4CL promoter. The inverter repeat comprises a segment of the gene of interest (forward arrow), an intron from the yabby gene (SEQ ID NO: 64) and the same segment of the gene of interest in the opposite orientation (back arrow). A transcriptional terminator completes the construct.

FIG. 10 provides mass spectra of loblolly pine samples. 2000c=control; 1268b=transgenic tree comprising the DNA construct pARB585.

DETAILED DESCRIPTION

Figure 1:
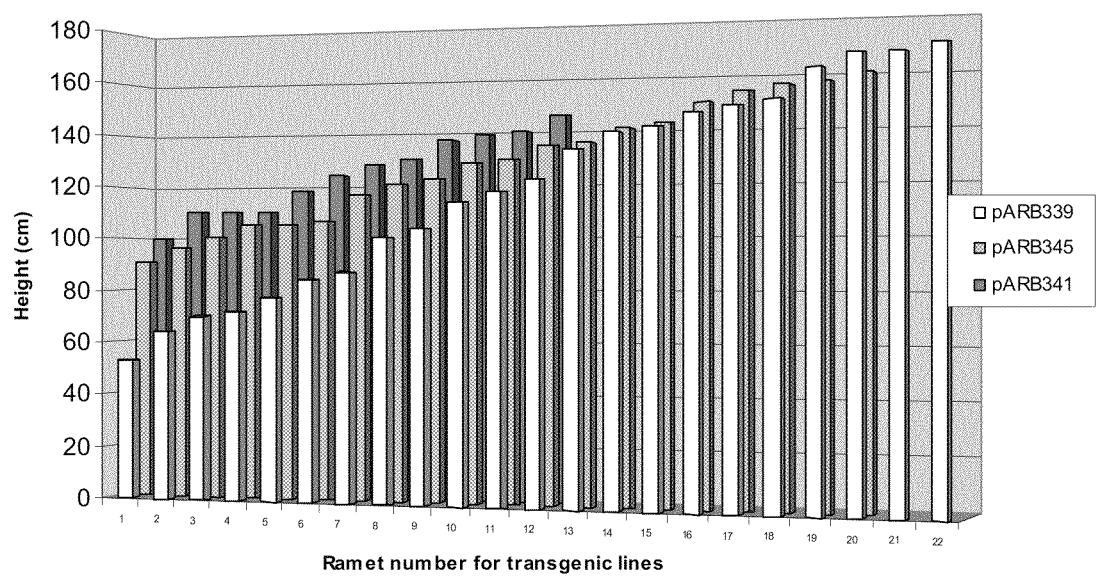
FIG. 1 provides a bar chart showing the resulting heights of transgenic *Eucalyptus* trees.

In one embodiment, DNA constructs can be used for suppressing the expression of targeted genes. The constructs and methods described herein can be used in individual cells in vitro or in vivo. In general, the constructs selectively suppress target genes by encoding double-stranded RNA (dsRNA) and initiating RNA interference (RNAi). In a preferred embodiment, the DNA constructs are used to reduce the lignin content in plants.

In one aspect, a DNA construct useful for modulating the lignin content of plants is provided. In one embodiment, a DNA construct comprises a promoter operably linked to a first DNA segment that corresponds to at least a portion of a 4-coumarate co-enzyme A ligase (4CL) gene, a spacer DNA segment, and a second DNA segment that is complementary to the first DNA segment, wherein the first and second DNA segments are arranged in a 5' to 3' direction, respectively, in the DNA construct. Thus, when transcribed, the DNA constructs yield a RNA molecule comprising a first RNA segment corresponding to at least a portion of a 4CL gene, a spacer RNA segment and a second RNA segment that is complementary to the first RNA segment. Constructs comprising DNA segments for C3H, C4H, CCoAOMT and CCR operate in similar fashion.

While the mechanism by which the invention operates is not fully understood, and the inventors do not wish to limit their invention to any particular theory, it is believed that the first and second RNA segments of the resulting RNA molecule form a stem-loop. The dsRNA of the stem loop likely is degraded into small interfering RNA (siRNA) of about 21-23 nucleotides in length. Then, siRNAs associate with a ribonuclease complex (termed RISC for RNA Induced Silencing Complex) which target this complex to complementary mRNAs. RISC then cleaves the targeted mRNAs opposite the complementary siRNA, making the mRNA susceptible to other RNA degradation pathways.

DEFINITIONS

The phrases "target gene" and "gene of interest" are used interchangeably herein. Target gene, as understood in the current context, is used to mean the gene that is pinpointed for modulation or suppression. The targeted gene may or may not contain regulatory elements such as, for example, a transcription factor binding site or enhancer. Genes that can be chosen for suppression include those that code for structural proteins, such as cell wall proteins, or for regulatory proteins such as transcription factors and receptors, as well as other functional genes. Furthermore, the term is meant to include not only the coding region of a polypeptide but also introns present in the DNA, regulatory elements, the promoter and the transcription terminator. Thus, "at least a portion of the target gene" is meant to include at least a portion of the transcribed sequence and/or at least a portion of the promoter and/or at least a portion of the terminator of the gene of interest.

DNA constructs described herein, at their most basic level, comprise a promoter, one or more DNA segments and a transcription terminator. As used herein, "DNA segment" is meant to refer to a deoxyribonucleic acid molecule comprised of at least several contiguous bases. The DNA segment that corresponds to the target gene may be 30 base pairs (bp) or greater in length, preferably at least 50 bp and less than 2000 bp, and more preferably at least 100 bp and less than 750 bp. The DNA segment can be single- or double-stranded. A DNA segment, within the context of the present invention, can include a gene or cDNA or a portion thereof, or it can include a promoter or a regulatory element or a portion thereof.

The term "RNA segment" refers to a ribonucleic acid molecule comprised of at least several contiguous bases. The RNA segment may be a transcript, i.e. an mRNA molecule that codes for an entire polypeptide, or it may be a portion thereof. Furthermore, the RNA segment need not code for a polypeptide or any portion thereof, as long as the segment meets the qualities of an RNA segment defined herein. For example, an RNA segment may comprise an intron, a 5'-UTR, or a 3'-UTR, which do not encode peptides. An RNA segment also is produced when a DNA segment comprising a promoter, a regulatory element, or a non-gene sequence is transcribed.

The term "spacer" refers to a series of contiguous nucleotides that separates two DNA or RNA segments. In one example, a "spacer DNA segment" codes for a "spacer RNA segment" that separates two RNA segments. The length of a spacer may vary over a wide range, from 10 base pairs (bp) to 2000 bp or more. When very long complementary segments of DNA are separated by a short spacer, the construct may be unstable. Therefore, the spacer preferably should be between ¼ to 2 times the length of the segments it is separating. For example, if complementary DNA segments of 160 bp are present, the spacer segment between them would preferably be between 40 to 320 bp. The spacer may encode an intron that is spliced out of the transcript so that the resulting spacer RNA is much shorter than the complementary DNA segments of the transcript.

"Complementary" RNA or DNA segments are segments that will specifically bind to each other. Preferably, the sequence of two complementary segments should be at least 80% complementary to each other. More preferably, the complementarity should be at least 85%, 90%, 95%, 96%, 97%, 98%, 99% or even 100%. The DNA segments that are complementary to each other may be 30 base pairs (bp) or greater in length, preferably at least 50 bp and less than 2000 bp, and more preferably at least 100 bp and less than 750 bp.

By 95% complementarity, for example, it is meant that nucleotides of the complementary RNA or DNA segments will bind to each other in an exact base-to-base manner, except that one RNA or DNA segment may contain up to 5 point mutations per 100 bases of the other complementary strand of the RNA or DNA segment. The point mutations may be in the form of a deleted base or a substituted base. Furthermore, these mutations of the reference sequence may occur at the 5' or 3' terminal positions of one of the complementary nucleotide sequences or anywhere between the terminal positions, interspersed either individually among nucleotides in the reference sequence or in one or more contiguous groups within the reference sequence.

As a practical matter, percent complementarity, as well as identity, can be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps. Alternatively, percent complementarity can be assessed using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Two DNA segments that have similar or identical sequences on opposite DNA strands are referred to as "inverted repeats." Transcription through a region with inverted DNA repeats produces RNA segments that are "complementary" to each other. A transcript that comprises two complementary segments of RNA can form a single RNA molecule with double-stranded regions. Such double-stranded regions are sometimes called "stem-loops" or "hairpins."

By "transcription terminator" is meant a segment of DNA that encodes the 3'-end of an RNA transcript that causes RNA polymerase to halt or retard transcription. Because most eukaryotic mRNAs have poly(A) segments added to their 3'-ends, most transcription terminators specify a base or bases to which adenosyl residues are added. Thus, a transcription terminator can comprise DNA encoding at least a portion of the 3'-UTR of an mRNA immediately adjacent to and including the nucleotide(s) to which a poly(A) tail is added. A transcription terminator additionally can comprise at least a portion of the DNA sequence immediately after the site(s) of polyadenylation to provide a more complete DNA context for the transcription stop site. Transcription terminators also include segments that halt transcription other than terminators for polyadenylation such as transcription terminators for histone genes or ribosomal RNA genes.

DNA constructs, as used herein, also encompass vectors. The term "vector" refers to a DNA molecule capable of autonomous replication in a host cell. As known to those skilled in the art, a vector includes, but is not limited to, a plasmid, cosmid, phagemid, viral vectors, phage vectors, yeast vectors, mammalian vectors and the like. Typically, vectors will include a gene coding for a drug resistance marker, a thymidine kinase gene or a gene that complements an auxotroph. Various antibiotic resistance genes have been incorporated into vectors for the purpose of aiding selection of host cell clones containing such vectors. For example, antibiotic resistance genes incorporated into vectors intended for introduction into bacterial host cells include, but are not limited to, a gene that confers resistance to an antibiotic selected from the group consisting of ampicillin, kanamycin, tetracycline, neomycin, G418, blastocidin S and chloramphenicol. Genes for complementing an auxotroph are genes encoding enzymes or proteins which facilitate usage of nutritional or functional components by the host such as a purine, pyrimidine, amino acid (e.g., lysine, tryptophan, histidine, leucine, cysteine), or sphingolipid.

Additionally, vectors will include an origin of replication (replicons) for a particular host cell. For example, various prokaryotic replicons are known to those skilled in the art, and function to direct autonomous replication and maintenance of a recombinant molecule in a prokaryotic host cell.

The term "operably linked" refers to the chemical fusion, ligation, or synthesis of DNA such that a promoter-DNA sequence combination is formed in a proper orientation for the DNA sequence to be transcribed into an RNA segment. Transcription from the promoter-DNA sequence can be regulated by the promoter, possibly in combination with other regulatory elements. Alternatively, transcription from the promoter-DNA segment may not be regulated by the promoter. In the construction of the promoter-DNA sequence combination, it is generally preferred to position the promoter at a distance upstream from the initial codon of the DNA segment that is approximately the same as the distance between the promoter and the segment it controls in its natural setting. However, as known in the art, substantial variation in the distance can be accommodated without loss of promoter function.

The term "promoter" denotes a nucleotide sequence, natural or synthetic, capable of binding RNA polymerase to initiate transcription. Such promoters are known to those skilled in the art and may include bacterial, viral, fungal, plant, mammalian, or other eukaryotic promoters, the selection of which depends on the host cell or organism being transformed. It is expected that silencing of the target gene will be most effective when the suppressing construct is transcribed in the same tissue as the target gene. Although there is evidence that the silencing signal can be translocated to distant parts of a plant (e.g., Palauqui and Vaucheret, 1998, PNAS 95: 9675-9680.), some cells may not be able to receive such a signal. For example, GFP expression at the very tip of the growing shoot was not silenced by a viral suppression construct (Dalmay et al., 2000, Plant Cell 12: 369-379.). To achieve silencing of a gene expressed in many types of cells, a constitutive promoter of at least moderate strength is preferred. Examples of constitutive promoters that act in plants are viral promoters such as CaMV 35S or FiMV (Sanger et al., 1990. Plant Mol. Biol. 14: 433-443), bacterial promoters such as nopaline synthase (nos) or mannopine synthase (mas), or plant promoters such as those from the *Arabidopsis* ACTIN2 or UBIQUITIN10 genes (An et al., 1996, Plant J. 10: 107-121; Norris et al., 1993, Plant Mol. Biol. 21: 895-906). Target genes with limited expression patterns also can be silenced using a constitutive promoter to drive the suppression construct. However, it may be desirable to avoid expression of the suppression construct beyond what is necessary for the silenced phenotype. A promoter for the suppression construct could be used that has a pattern of expression similar to that of the target gene. For example, if silencing of a xylem-expressed target is planned, the promoter from the parsley 4CL gene (Hauffe et al., 1993, Plant J. 4: 235-253) could be used, or if a meristem-specific gene is targeted, the *Arabidopsis* PROLIFERA promoter (Springer et al., 1995, Science 268: 877-880) could be used. In one embodiment, the promoter is derived from a different species than the species being transformed, to avoid interactions between identical promoter sequences. Various other promoters for expression in eukaryotic cells are known in the art, including, but not limited to, viral or viral-like basal promoters like the SV40 late promoter and the RSV promoter, and fungal or mammalian cellular promoters (see, e.g., Larsen et al., 1995, Nucleic Acids Res. 23:1223-1230; Donis et al., 1993, BioTechniques 15:786-787; Donda et al., 1993, Mol. Cell. Endocrinol. 90:R23-26; and Huper et al., 1992, In Vitro Cell Dev. Biol. 28A:730-734). Various replicons are known to those skilled in the art that function in eukaryotic cells to direct replication and maintenance of a recombinant molecule, of which it is part of, in a eukaryotic host cell.

The term "regulatory element" refers to nucleic acid sequences that affect the specificity or efficiency of DNA transcription or mRNA translation including, but not limited to, binding sites for transcription factors, enhancers, and transcription or translation initiation and termination signals. Enhancer sequences are DNA elements that appear to increase transcriptional efficiency in a manner relatively independent of their position and orientation with respect to a nearby DNA segment. Thus, depending on the DNA construct, an enhancer may be placed either upstream or downstream from a particular DNA segment to increase transcriptional efficiency. Such regulatory elements may be inserted into construct DNA sequences using recombinant DNA methods known in the art. Other regulatory elements include, but are not limited to, a 5' untranslated region (5'UTR) on the RNA segment as well as a 3'UTR (i.e., comprising the poly (A) tail) on the RNA segment, which are necessary for stability and efficient translation of the RNA segment or transcript.

As used herein, a "cassette" is a type of DNA construct comprising a promoter, a transcription terminator, and the DNA segments inserted between them. A cassette can be used to drive the expression of DNA or RNA segments in host cells or organisms in which the promoter is active.

The term "substantial sequence identity" describes the relatedness of two or more nucleotide sequences. Preferably, the sequences are at least 80% identical to each other, as calculated above. More preferably, the identity should be at least 85%, 90%, 95%, 96%, 97%, 98%, 99% or even 100%.

"About" will be understood by persons of ordinary skill in the art and will vary to some extent on the context in which the term is used. If there are uses of the term which are not clear to persons of ordinary skill in the art given the context in which it is used, "about" will mean up to plus or minus 10% of the particular term.

Discussion

In one aspect of the invention, DNA constructs are provided that are useful for modulating the lignin content in plants. In one embodiment, a DNA construct comprises a promoter operably linked to a first DNA segment that corresponds to at least a portion of a 4-coumarate co-enzyme A ligase (4CL) gene, a spacer DNA segment, and a second DNA segment that is complementary to the first DNA segment, wherein the first and second DNA segments are arranged in a 5' to 3' direction, respectively, in the DNA construct.

A constitutive promoter, such as superubiquitin from *P. radiata* (U.S. Pat. No. 6,380,459, which is hereby incorporated by reference), can be used to drive the expression of the target 4CL or other lignin biosynthesis gene. In another embodiment, a DNA construct of the present invention comprises a promoter that directs expression specifically to the xylem. A promoter fragment isolated from the region upstream of the 4CL gene in *P. taeda* (U.S. Pat. No. 6,252, 135, which is hereby incorporated by reference.) is one example of a promoter that shows strong xylem-preferred expression. Experimental evidence described herein demonstrates that the use of a 4CL promoter in the inventive DNA constructs effectively reduces the lignin content while not adversely impacting plant height.

The first and second DNA segments of the inventive constructs can be derived from any 4CL gene. In a preferred embodiment, when modifying the lignin content in pine or eucalyptus trees, the first and second DNA segments are derived from the 4CL gene from *Pinus radiata* (pine) (U.S. Patent Application Publication 20030131373) or the 4CL gene from *E. grandis* (U.S. Pat. No. 6,410,718). Similarly, the first and second DNA segments of the inventive constructs can be derived from any portion of a 4CL gene. For example, fragments of about 50 bp, 100 bp, 200 bp, 400 bp, 600 bp or 1000 bp can be used. Other exemplary lengths shown herein include 189 bp, 327 bp, 334 bp, 373 bp, 389 bp and 668 bp. In preferred embodiments, the first DNA segment comprises a fragment selected from the sequences depicted in SEQ ID NOS. 18, 19, 20, 21, 22, 23, 24, 33 and 48.

The first DNA segment can be derived from either the sense strand or the antisense strand of a 4CL gene. As the second DNA segment is complementary to the first DNA segment and therefore derived from the opposing strand, the strand selection for the first DNA segment necessarily affects the source of the second DNA segment.

As noted above, a spacer DNA segment codes for a spacer RNA segment which serves to separate other RNA segments. A spacer RNA segment functions in the present invention as the loop in the stem-loop resulting from transcription of the DNA cassette of the inventive constructs. A spacer DNA segment can be completely synthetic or derived from a natural DNA sequence. In one embodiment, the spacer DNA segment is derived from an intron. Exemplary spacer DNA segments are shown in SEQ ID NOS: 9, 15, 64.

Previously identified genes of interest, or portions or promoters thereof can be isolated using methods and techniques designed for the manipulation of nucleic acid molecules, which are well known in the art. For example, methods for the isolation, purification and cloning of nucleic acid molecules, as well as methods and techniques describing the use of eukaryotic and prokaryotic host cells and nucleic acid and protein expression therein, are described by Sambrook, et al., Molecular Cloning: A Laboratory Manual, Second Edition, Cold Spring Harbor, N.Y., 1989, and Current Protocols in Molecular Biology, Frederick M. Ausubel et al. Eds., John Wiley & Sons, Inc., 1987, the disclosure of which is hereby incorporated by reference.

The DNA constructs, including at least a portion of the gene or promoter of interest, can be introduced into host cells, which as stated previously, can be individual cells, cells in culture, cells as part of a host organism, a fertilized oocyte or gametophyte or an embryonic cell. The term "introduced" refers to standard procedures known in the art for delivering recombinant vector DNA into a target host cell. Such procedures include, but are not limited to, transfection, infection, transformation, natural uptake, electroporation, biolistics and *Agrobacterium*. *Agrobacterium* has been used successfully in a variety of species including poplars (Leple, J. C. et al. 1992. Plant Cell Rep. 11: 137-141.), eucalyptus (Tournier, V. et al. 2003. Transgenic Res. 12: 403-411.) and pine (U.S. Pat. No. 6,518,485 (biolistics) and US published patent application 20020100083). *Agrobacterium* are the only published methods for successfully getting regenerated plants of transgenic loblolly pine), Norway spruce (Wenck, A. R. et al. 1999. Plant Mol. Biol. 39: 407-416.), rice (Hiei, Y. et al. 1997. Plant Mol. Biol. 35: 205-218.; Cheng, X. et al. 1998. Proc. Natl. Acad. Sci. USA. 95: 2767-2772.), wheat (Cheng, M. et al. 1997. Plant Physiol. 115: 971-980.) and maize (Ishida, Y. et al. 1996. Nat. Biotechnol. 14: 745-750.). Transformation has been utilized in species such as barley (Tingay, S. et al. 1997. Plant J. 11: 1369-1376.), sugarcane (Arencibia, A. D. et al. 1998. Transgenic Research 7: 1-10; Enriquez-Obregon, G. A. et al. 1998. Plant 206: 20-27.), banana (May, G. D. et al. 1995. Bio/Technology 13: 486-492.), *Asparagus officinalis* (Delbreil, B. et al. 1993. Plant Cell Rep. 12: 129-132.) and *Agapanthus praecox* (Suzuki, S. et al. 2001. Plant Sci. 161: 89-97.).

The efficacy of DNA constructs in modulating lignin content can be measured in a variety of ways. For example, acetyl bromide lignin determinations can be carried out on extractive free ground samples following the procedure used at the US Dairy Forage Research Center, Madison, Wis. (Fukushima, R. S. and Hatfield, R. D., *J. Ag. Food Chem.*, 49(7): 3133 (2001)). Pyrolysis molecular beam mass spectroscopy also can be used. The method consists of rapidly heating samples (0.1 g) in an inert, helium atmosphere at 500° C. The generated pyrolysis products are sampled directly in real time by expanding through a sampling orifice with subsequent formation of the molecular beam, which provides rapid sample quenching and inhibits sample condensation. The mass spectrometer provides universal detection of all sampled products and the molecular beam sampling ensures that representative products from the original molecules are detected (Magrini et al., *Environmental Pollution*, 116: 255-268 (2002)). In an another example, nuclear magnetic resonance (NMR) can be used to analyze lignin structure. NMR is an analytical method that can detect subatomic and structural information of molecules by measuring the adsorption of radio-frequency electromagnetic radiation by nuclei under the influence of a magnetic field. Typically, 1H and 13C are the two main nuclei used to characterize underivatized lignin, following the method of Li, S. and K. Lundquist (*Nordic Pulp and Paper Research J.*, 3. 191-195)).

The reduction in lignin levels and the possible associated increase in CHO levels of trees can be both an economic an environmental advantage for the pulp industry. The reduction of lignin in tress should lead to the reduction of chemicals required to make pulp and possibly even a reduction in the amount of chemicals required to bleach the pulp.

The following examples serve to illustrate various embodiments of the present invention and should not be construed, in any way, to limit the scope of the invention.

EXAMPLES

Example 1

Construction of cDNA Libraries

To identify monolignol synthesis, monolignol transport, and lignin polymerization gene candidates in *P. radiata* and *E. grandis* databases, cDNA sequences were compared to public domain sequences (by SWISS-PROT/TrEMBL ID's) to search against the pine and eucalyptus databases (non-redundant by contig, expect <1.0e-2).

The contig consensus DNA and protein sequences were then obtained for these hits, and duplicate sequences were identified. A multiple alignment was then carried out with the protein sequences. The protein alignment was created using the remaining pine and eucalyptus sequences along with the *Arabidopsis* members. From the protein alignment, a dendogram was created. These sequences were analyzed by primer walking to provide a full length sequence (best HT pick from the contig analyzed for full length sequence).

The public domain monolignol synthesis, monolignol transport, and lignin polymerization gene sequences from maize, cotton, rice, and poplar were also extracted and blasted against the pine and eucalyptus databases. The completed primer walked pine and eucalyptus sequences were also blasted against ownseq and the top 500 hits were taken. This was done so that the sequences could be used to search further and ensure that nothing in the pine and eucalyptus databases had been missed by using the *Arabidopsis* superfamily. This search resulted in an additional 4 sequences which were not found in the previous searches. These sequences were then also sent for primer walked full length sequence.

After removing a small number of additional duplicates after primer walking, pine and eucalyptus primer walked monolignol synthesis, monolignol transport, and lignin polymerization superfamily members were identified. The classification of these sequences was confirmed by alignment with ClustalX, the corresponding dendogram, and MEME/MAST analysis.

To identify additional sequence 5' or 3' of a partial cDNA sequence in a cDNA library, 5' and 3' rapid amplification of cDNA ends (RACE) was performed. using the SMART RACE cDNA amplification kit (Clontech Laboratories, Palo Alto, Calif.). Generally, the method entailed first isolating poly(A) mRNA, performing first and second strand cDNA synthesis to generate double stranded cDNA, blunting cDNA ends, and then ligating of the SMART RACE. Adaptor to the cDNA to form a library of adaptor-ligated ds cDNA. Gene-specific primers were designed to be used along with adaptor specific primers for both 5' and 3' RACE reactions. Using 5' and 3' RACE reactions, 5' and 3' RACE fragments were obtained, sequenced, and cloned. The process may be repeated until 5' and 3' ends of the full-length gene were identified. A full-length cDNA may generated by PCR using primers specific to 5' and 3' ends of the gene by end-to-end PCR.

For example, to amplify the missing 5' region of a gene from first-strand cDNA, a primer was designed 5'→3' from the opposite strand of the template sequence, and from the region between ~100-200 bp of the template sequence. A successful amplification should give an overlap of ~100 bp of DNA sequence between the 5' end of the template and PCR product.

RNA was extracted from four pine tissues, namely seedling, xylem, phloem and structural root using the Concert Reagent Protocol (Invitrogen, Carlsbad, Calif.) and standard isolation and extraction procedures. The resulting RNA was then treated with DNase, using 10 U/µl DNase I (Roche Diagnostics, Basel, Switzerland). For 100 µg of RNA, 9 µl 10× DNase buffer (Invitrogen, Carlsbad, Calif.), 10 µl of Roche DNase 1 and 90 µl of Rnase-free water was used. The RNA was then incubated at room temperature for 15 minutes and 1/10 volume 25 mM EDTA is added. A RNeasy mini kit (Qiagen, Venlo, The Netherlands) was used for RNA purification according to manufacturer's protocol.

To synthesize cDNA, the extracted RNA from xylem, phloem, seedling and root was used and the SMART RACE cDNA amplification kit (Clontech Laboratories Inc, Palo Alto, Calif.) was followed according to manufacturer's protocol. For the RACE PCR, the cDNA from the four tissue types was combined. The master mix for PCR was created by combining equal volumes of cDNA from xylem, phloem, root and seedling tissues. PCR reactions were performed in 96 well PCR plates, with 1 ml of primer from primer dilution plate (10 mM) to corresponding well positions. 49 ml of master mix is aliquoted into the PCR plate with primers. Thermal cycling commenced on a GeneAmp 9700 (Applied Biosystems, Foster City, Calif.) at the following parameters:

94° C. (5 sec),
72° C. (3 min), 5 cycles;
94° C. (5 sec),
70° C. (10 sec),
72° C. (3 min), 5 cycles;
94° C. (5 sec),
68° C. (10 sec),
72° C. (3 min), 25 cycles.

cDNA was separated on an agarose gel following standard procedures. Gel fragments were excised and eluted from the gel by using the Qiagen 96-well Gel Elution kit, following the manufacturer's instructions.

PCR products were ligated into pGEMTeasy (Promega, Madison, Wis.) in a 96 well plate overnight according to the following specifications: 60-80 ng of DNA, 5 µl 2× rapid ligation buffer, 0.5 µl pGEMT easy vector, 0.1 µl DNA ligase, filled to 10 µl with water, and incubated overnight.

Each clone was transformed into *E. coli* following standard procedures and DNA was extracted from 12 clones picked by following standard protocols. DNA extraction and the DNA quality was verified on an 1% agarose gel. The presence of the correct size insert in each of the clones was determined by restriction digests, using the restriction endonuclease EcoRI, and gel electrophoresis, following standard laboratory procedures.

Example 2

Construction of Pine 4CL Expression Vectors

Figure 4:
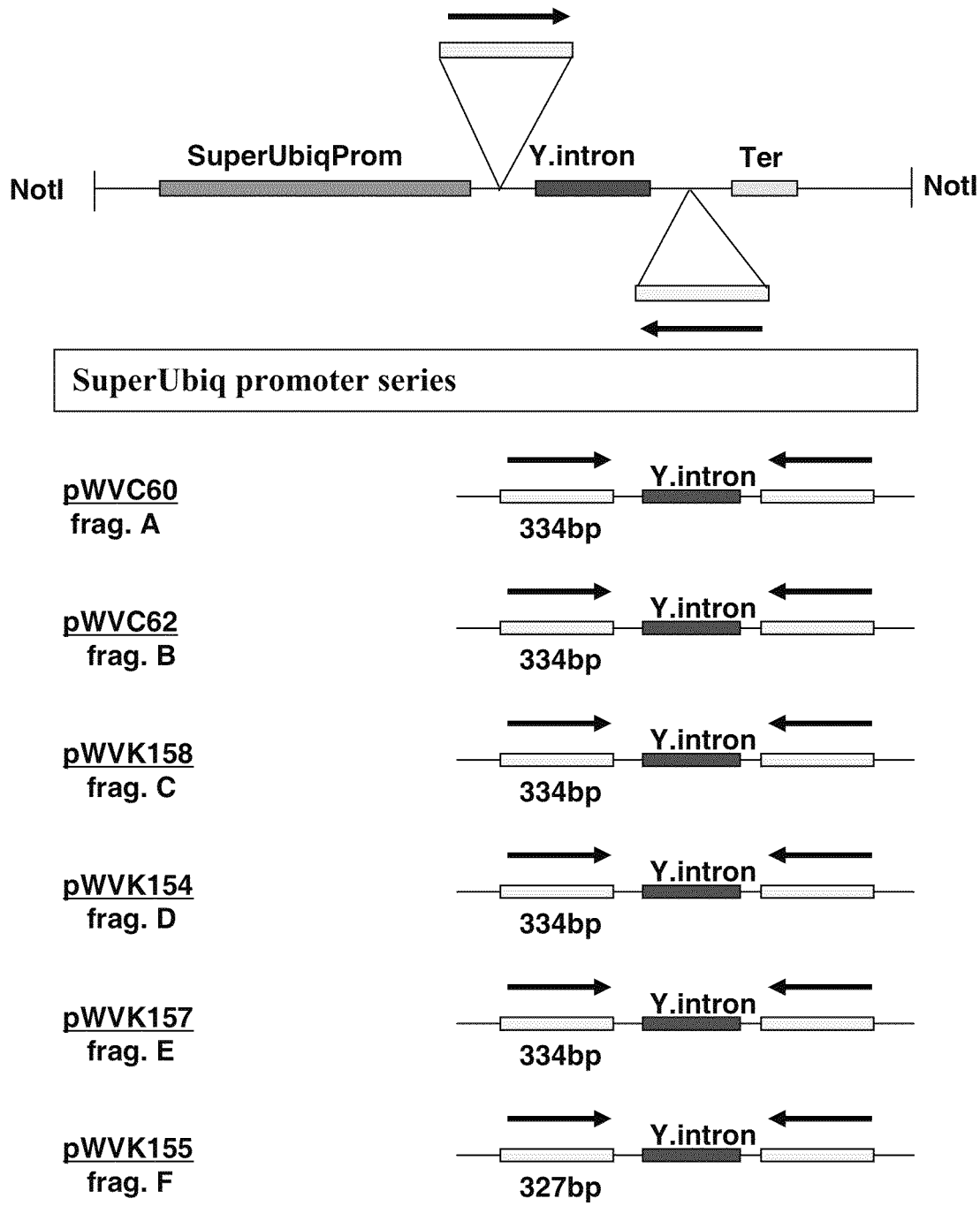
FIG. 4 provides a schematic of several 4CL DNA constructs for use in modulating lignin in pine trees. The constructs use the general design as described in FIG. 7. The figure shows a series of constructs that use the SuperUbiq promoter and a selection of segments from the pine 4CL gene (SEQ ID NO: 66). pWVC60 comprises fragment A (SEQ ID NO: 18), pWVC62 comprises fragment B (SEQ ID NO: 19), pWVK158 comprises of fragment C (SEQ ID NO: 20), pWVK154 comprises of fragment D (SEQ ID NO: 21), pWVK157 comprises of fragment E (SEQ ID NO: 22) and pWVK155 comprises of fragment F (SEQ ID NO: 23).
Figure 5:
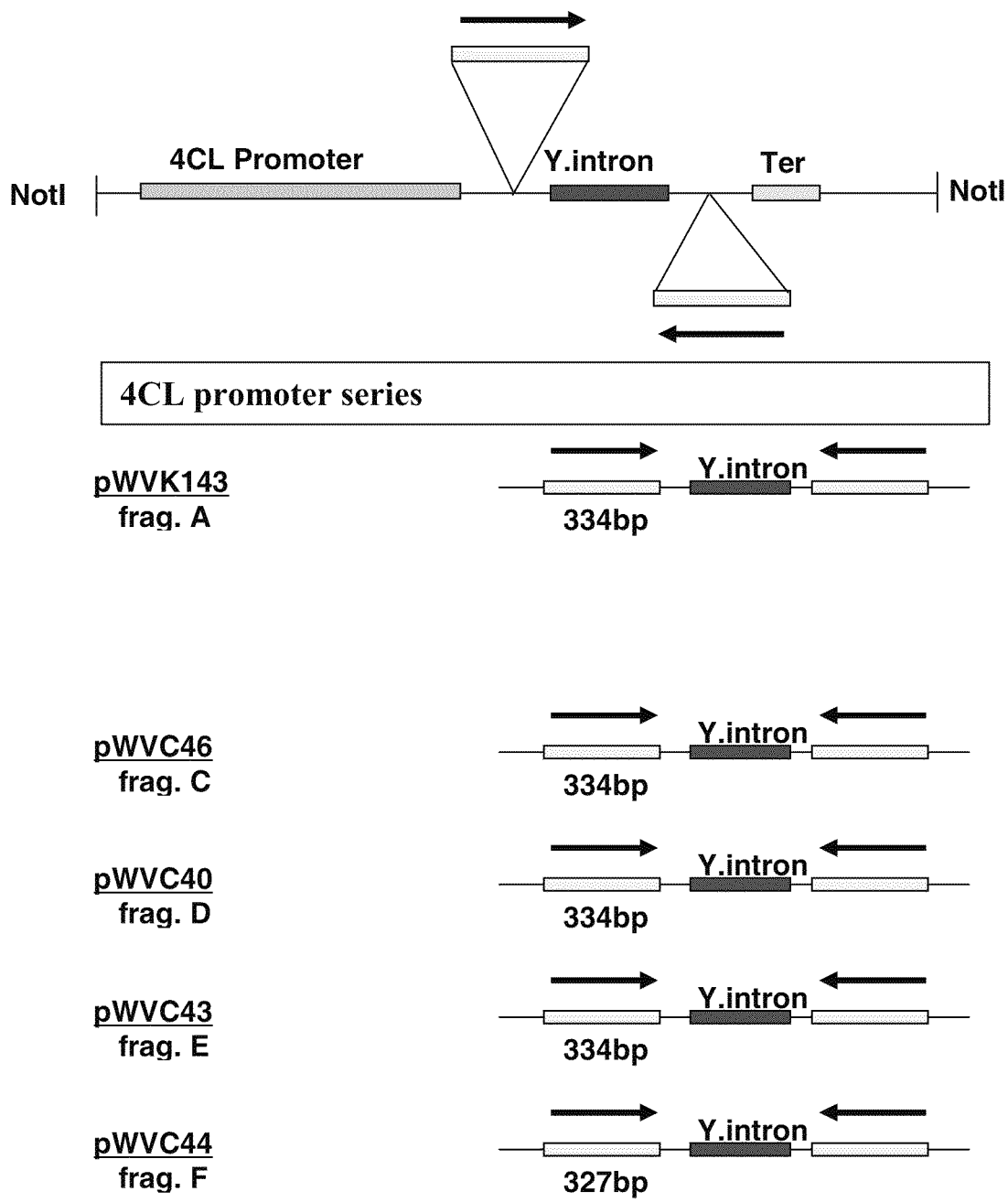
FIG. 5 provides a schematic of several 4CL DNA constructs for use in modulating lignin in pine trees. The constructs use the general design as described in FIG. 7. The figure shows a series of constructs that use the 4CL promoter and a selection of segments from the pine 4CL gene (SEQ ID NO: 66).). pWVK143 comprises fragment A (SEQ ID NO: 18), pWVC46 comprises fragment C (SEQ ID NO: 20), pWVC40 comprises fragment D (SEQ ID NO: 21), pWVC43 comprises fragment E (SEQ ID NO: 22) and pWVC44 comprises fragment F (SEQ ID NO: 23).

A series of recombinant constructs comprising at least a portion of a 4CL gene from loblolly pine were prepared and evaluated for their ability to reduce the lignin content in plants. In general, each DNA construct comprises a promoter operably linked to a first DNA segment that corresponds to at least a portion of a 4CL gene, a spacer DNA segment, and a second DNA segment that is complementary to the first DNA segment, wherein the first and second DNA segments are arranged in a 5' to 3' direction, respectively, in the DNA construct. Eleven constructs were designed and prepared using different fragments of the 4CL gene *Pinus radiata* (SEQ ID NO: 66) and different promoters. The general designs for the constructs are depicted in FIGS. 3 to 5. The superubiquitin promoter (U.S. Pat. No. 6,380,459, Ranjan J Perera et al., Plant & Animal Genome VIII Conference (2000)) was used as a constitutive promoter, while a 4CL promoter from *P. taeda* (U.S. Pat. No. 6,252,135) was used as a vascular-preferred promoter. An intron from the YABBY gene (SEQ ID NO:64) from *Arabidopsis thaliana* (Foster T M et al., *Plant Cell*, 14 (7): 1497-1508 (2002)) was used as a spacer DNA segment. The constructs utilized portions of the 4CL gene from *P. radiata* depicted in SEQ ID NO: 66. The nucleic acid sequences of the 4CL RNAi fragments (A to H) (SEQ ID NOS: 18-24, respectively) utilized in the constructs were as follows:

Fragments for the Pine 4CL RNAi constructs
Pine 4CL 334 nt. Fragment A=1-334 5'UTR, ATG and coding seq.
   334 nt. Fragment B=335-668
   334 nt. Fragment C=669-1002
   334 nt. Fragment D=1003-1336
   334 nt. Fragment E=1337-1670
   327 nt. Fragment F=1671-1997 coding seq., STOP, 3'UTR
   373 nt. Fragment G=1121-1493
   668 nt. Fragment H=frag. A+B=1-668 5'UTR, ATG and coding seq.

A backbone vector was prepared by adding additional restriction endonuclease sites to the multiple cloning site of the plasmid pBluescript (BRL Gibco Life Technologies, Gaithersburg Md.). The NotI and SstI sites in the original pBluescript vector were destroyed by digestion of the plasmid with NotI and SstI and filling in the ends using Klenow and T4 Polymerase (Invitrogen Corp., Carlsbad Calif.). The plasmid was circularized by blunt-end ligation and then digested with the restriction endonucleases EcoRI and HindIII to enable cloning of linkers. Linkers (phosphorylated at the 5' end) containing additional restriction sites (given in SEQ ID NOS: 1 and 2) were annealed together and ligated into the EcoRI/HindIII-digested pBluescript vector.

The 3' UTR from the *P. radiata* superubiquitin gene (U.S. Pat. No. 6,380,459) was cloned into the plasmid pBI-121 (Jefferson et al., *EMBO J.* 6:3901-3907, 1987). First, a fragment of the 3' UTR of the gene was amplified using standard PCR techniques and the primers given in SEQ ID NOS: 3 and 4. These primers contained additional nucleotides to provide an SstI restriction site for cloning into SstI-digested plasmid pBI-121. Then, the 3' UTR fragment, containing the nos terminator, was transferred to the pBluescript plasmid. The 3' UTR and nos terminator fragment of pBI-121 was amplified with PCR using primers given in SEQ ID NOS: 5 and 6, cleaved with KpnI and ClaI and cloned into the modified pBluescript digested with KpnI and ClaI.

To this construct, the *P. radiata* superubiquitin promoter sequence with intron was added. The promoter/intron sequence was first amplified from the *P. radiata* superubiquitin sequence identified in U.S. Pat. No. 6,380,459 using standard PCR techniques and the primers of SEQ ID NOS: 7 and 8. The amplified fragment was then ligated into the base vector using XbaI and PstI restriction digestion.

The *P. radiata* 4 CL intron sequence (SEQ ID NO: 9) from the *P. radiata* cDNA was amplified using standard PCR techniques and the primers of SEQ ID NOS: 10 and 11, then cloned into XcmI-digested vector backbone using T-tailed ligation.

To isolate and characterize monolignol synthesis, monolignol transport, and lignin polymerization and monolignol synthesis, monolignol transport, and lignin polymerization-like genes from *E. grandis* and *P. radiata*, total RNA was extracted from plant tissue (using the protocol of Chang et al., Plant Mol. Biol. Rep. 11:113-116 (1993). Plant tissue samples were obtained from phloem (P), cambium (C), expanding xylem (X1), and differentiating and lignifying xylem (X2).

mRNA was isolated from the total RNA preparation using either a Poly(A) Quik mRNA Isolation Kit (Stratagene, La Jolla, Calif.) or Dynal Beads Oligo $(dT)_{25}$ (Dynal, Skogen, Norway). cDNA expression libraries were constructed from the purified mRNA by reverse transcriptase synthesis followed by insertion of the resulting cDNA clones in Lambda ZAP using a ZAP Express cDNA Synthesis Kit (Stratagene), according to the using the manufacturer's protocol. The resulting cDNAs were packaged using a Gigapack II Packaging Extract (Stratagene) using an aliquot (1-5 µL) from the 5 mL ligation reaction dependent upon the library. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and selected for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequence for positive clones was obtained using a Perkin Elmer/Applied Biosystems Division Prism 377 sequencer. cDNA clones were sequenced first from the 5' end and, in some cases, also from the 3' end. For some clones, internal sequence was obtained using either Exonuclease III deletion analysis, yielding a library of differentially sized subclones in pBK-CMV, or by direct sequencing using gene-specific primers designed to identified regions of the gene of interest.

Using the methods described in Example 1, a *Pinus radiata* cDNA expression library was constructed from xylem and screened. DNA sequences for positive clones were obtained using forward and reverse primers on a Perkin Elmer/Applied Biosystems Prism 377 sequencer and the determined sequences were compared to known sequences in the EMBL database as described above. Based on similarity to known sequences from other plant species, the isolated DNA sequences were identified as encoding 4CL (SEQ ID NOS: 18 24) and caffeoyl CoA methyl transferase (SEQ ID NO:44).

A fragment from a *P. radiata* 4CL cDNA clone was amplified using standard PCR techniques and primers SEQ ID NOS: 12 and 13. The primers were designed to add PstI and ClaI restriction sites to both ends of the amplified fragments. The nucleotide sequence of the amplified fragment is provided as SEQ ID NO: 24. To clone the *P. radiata* 4CL fragment in the sense orientation, the amplified fragment was cut with the restriction enzyme PstI, blunt ended using Klenow and cloned into the backbone vector in a blunt-ended ClaI site. To clone the *P. radiata* 4CL fragment in the antisense orientation, the amplified fragment was digested with PstI and cloned into the PstI-digested backbone vector.

The yabby intron sequence (Foster et al. 2002, Plant Cell. 14 (7): 1497-1508) was amplified using primers similarly designed to those above for the Pr4CL and PDK intron sequences and cloned into the vector backbone as described above. Six additional fragments (SEQ ID NOS: 18-23) were amplified with primers similarly designed to those used for SEQ ID NO 24, except that primers for SEQ ID NO 18 were designed to add a SmaI restriction sites to both ends of the amplified fragment, primers for SEQ ID NO 19 were designed to add EcoRI and HindIII restriction sites at both ends of the amplified fragment, the primers for SEQ ID NO 22 were designed to add PstI restriction sites at both ends of the amplified fragment. The primers for SEQ ID NO 23 were designed to add a SmaI restriction site to the one end and EcoRI and HindIII restriction sites to the other end of the amplified fragment. All seven fragments were cloned in the sense and antisense directions into the backbone vector as described above or by using the listed restriction enzymes. The complete RNAi cassette containing the promoter::sense fragment::intron::antisense fragment::3'UTR::nos terminator construct, was removed from the pBluescript plasmid as described above, and cloned into the binary vector pART27 or pART29 (digested with NotI) using standard cloning techniques. The binary vector pART29 is a modified pART27 vector (Gleave, *Plant Mol. Biol.* 20:1203-1207, 1992) that contains the *Arabidopsis thaliana* ubiquitin 3 (UBQ3) promoter instead of the nos5' promoter and no lacZ sequences.

The complete RNAi cassette (SEQ ID NO: 14) containing the promoter::sense fragment::intron::antisense fragment::3'UTR::nos terminator construct, was removed from the pBluescript plasmid by a NotI restriction digestion, and cloned into the binary vector pART29 (digested with NotI) using standard cloning techniques to produce the final vector pARB513.

The constructs were re-engineered for use in pine by removing the NotI fragments and inserting these into a base vector that had a NotI site as well as a constitutive promoter expression GUS, to allow verification of transformation without PCR, and a selectable marker cassette comprising nptII driven by the *Arabidopsis* Ubq 10 promoter. The promoter::4CL RNAi cassette was removed from each of the vectors listed in Table 1 in the "Engineered from" column using the restriction enzyme NotI. The vector pWVR31 was linearized using the restriction enzyme NotI and treated with SAP to prevent it from reannealing to itself. Each fragment was ligated into pWVR31 at the NotI site to produce the vectors listed in Table 1.

TABLE 1

| Re-engineered Construct number | Engineered from |
|---|---|
| pWVC60 | pARB318 |
| pWVC62 | pARB319 |
| pWVK158 | pARB320 |
| pWVK154 | pARB321 |
| pWVK157 | pARB322 |
| pWVK155 | pARB323 |
| pWVK143 | pARB332 |
| pWVC42 | pARB333 |
| pWVC46 | pARB334 |
| pWVC40 | pARB335 |
| pWVC43 | pARB336 |
| pWVC44 | pARB337 |
| pWVC45 | pARB338 |

Constructs pWVK154, pWVK143, pWVC46 and pWVC40 were deposited with the American Type Culture Collection, P.O. Box 1549, Manassas, Va., USA, 20108 on Sep. 21, 2004, and accorded ATCC Accession Nos. PTA-6229, PTA-6228, PTA-6227, and PTA-6226, respectively.

The control vectors pWVC41 and pWVK159 were developed by cloning the 4CL promoter from *P. taeda* (U.S. Pat. No. 6,252,135) and the superubiquitin gene from *P. radiata* (U.S. Pat. No. 6,380,459) respectively, together with the GUS (intron) gene (reference) into the vector pWVR31. The backbone vector pWVR5 is a pBI121 vector (Clontech laboratories, Palo Alto Calif.) with the 35S promoter GUS sequence removed and the NOS promoter replaced with the UBQ10 promoter from *Arabidopsis* (Sun, C. W & Callis, J (1997) Plant J., 11:101-111). To make the vector pWVR8 the ActinII promoter (MEAGHER, *Int. Rev. Cytol.*, 125:139-163 (1991)) was amplified and cloned into the pWVR5 vector together with the GUS plus intron gene (Ohta et al., *Plant Cell Physiol*, 31:805-813 (1990)).

The backbone vector pWVR31 was engineered from the vector pWVR8 (*Arabidopsis* ActinII::GUSINT, UBQ10::NPTII). The UBQ11 promoter from *Arabidopsis* (Norris S R, et al. (1993) *Plant Mol. Biol.* 21(5):895-906) was amplified by PCR using primers, and this was used to replace the ActinII promoter from pWVR8 to make the vector pWVR31.

In addition, the vectors listed in Table 2 were constructed as described above but with modifications in at least one of the following sequences: the promoter and/or the binary vector. To clone a different promoter as listed in Table 2 into the final vector, the *P. radiata* superubiquitin promoter intron vector was digested with SmaI and SstI restriction enzymes and using standard techniques this fragment was cloned into Bluescript vectors containing either a 4CL promoter from *P. taeda*, an COMT promoter from *Eucalyptus grandis*, or a LIM promoter from *P. radiata*, using standard techniques. The *P. taeda* 4CL promoter (U.S. Pat. No. 6,252,135), the *E. grandis* COMT promoter (U.S. patent Ser. No. 10/703,091), and the *P. radiata* LIM promoter (U.S. patent application Ser. No. 10/717,897) were all amplified using primers similarly designed to those used to amplify the *P. radiata* superubiquitin promoter sequence with intron described above and then ligated into the base Bluescript vector as described above. The complete RNAi cassette containing the promoter::sense fragment::intron::antisense fragment::3'UTR::nos terminator construct, was removed from the pBluescript plasmid by a NotI restriction digestion and cloned into the binary vector pART29 or pWVK147 (digested with NotI) using standard cloning techniques. The pWVK147 vector is a pBI121 vector (Clontech laboratories, Palo Alto Calif.) with the 35S promoter GUS sequence removed and the NOS promoter replaced with the UBQ10 promoter from *Arabidopsis* (Sun, C. W & Callis, J (1997) *Plant J.,* 11:101-111) to drive the nptII gene. A unique HpaI restriction site was added to the vector by the addition of an adapter ligated at the ApaI and KpnI sites.

TABLE 2

| Final Vector | Base Binary Vector into which final cassette was inserted | Promoter driving the 4CL RNAi cassette containing the *P. radiata* 4CL intron as spacer |
| --- | --- | --- |
| pARB553 | pWVK147 | *Pinus radiata* SuperUbiq + Intron (SEQ ID NO: 76) |
| pARB555 | pWVK147 | *Pinus taeda* 4CL (SEQ ID NO: 77) |
| pARB561 | pWVK147 | *Eucalyptus grandis* COMT 485 bp fragment of U.S. Patent Publication No. 20040146904 |
| pARB562 | pWVK147 | *Pinus radiata* LIM 1607 bp fragment of U.S. Patent publication No. 20040163146 |
| pARB515 | pART29 | *Pinus taeda* 4CL (SEQ ID NO: 77) |
| pARB534 | pART29 | *Pinus radiata* LIM 1607 bp fragment of U.S. Patent publication No. 20040163146 |

The vectors listed in Table 3 were constructed using the same methods as those described above, except that the primers SEQ ID NOS: 16 and 17 were used to amplify the PDK intron sequence (Wesley et al., *Plant J.* 27:581-590, 2001) (SEQ ID NO: 15) using standard PCR techniques.

TABLE 3

| Final Vector | Base Binary Vector into which final cassette was inserted | Promoter driving the 4CL RNAi cassette containing the PDK intron as spacer |
| --- | --- | --- |
| pARB554 | pWVK147 | *Pinus radiata* SuperUbiq + Intron (SEQ ID NO: 76) |
| pARB556 | pWVK147 | *Pinus taeda* 4CL (SEQ ID NO: 77) |
| pARB557 | pWVK147 | *Eucalyptus grandis* COMT 485 bp fragment of U.S. Patent Publication No. 20040146904 |
| pARB558 | pWVK147 | *Pinus radiata* LIM 1607 bp fragment of U.S. Patent publication No. 20040163146 |
| pARB514 | pART29 | *Pinus radiata* SuperUbiq + Intron (SEQ ID NO: 76) |
| pARB516 | pART29 | *Pinus taeda* 4CL (SEQ ID NO: 77) |
| pARB518 | pART29 | *Pinus radiata* LIM 1607 bp fragment of U.S. Patent publication No. 20040163146 |

Example 3

Construction of *Eucalyptus* 4CL Expression Vectors

A series of recombinant constructs comprising at least a portion of a 4CL gene were prepared as described above and evaluated for their ability to reduce the lignin content in plants. In general, each DNA construct comprises a promoter operably linked to a first DNA segment (SEQ ID NO: 21) that corresponds to at least a portion of a 4CL gene from *Eucalyptus grandis* (U.S. Pat. No. 6,410,718) a spacer DNA segment, and a second DNA segment that is complementary to the first DNA segment, wherein the first and second DNA segments are arranged in a 5' to 3' direction, respectively, in the DNA construct. Initially, three constructs were prepared using different fragment lengths of the 4CL gene and different promoters. See Table 11. The general design for the constructs is depicted in FIG. 3. The superubiquitin promoter (U.S. Pat. No. 6,380,459; Ranjan J Perera et al., Plant & Animal Genome VIII Conference (2000)) was used as a constitutive promoter, while the promoter from 4CL gene in *P. taeda* SEQ ID NO: 77 was used as a vascular-preferred promoter. An intron from the YABBY gene from *Arabidopsis thaliana* (Foster T M et al., *Plant Cell,* 14 (7): 1497-1508 (Plant Cell)) was used as a spacer DNA segment. The nucleic acid sequences of the 4CL RNAi 200 bp fragment and 4CL RNAi 600 bp fragment are provided as SEQ ID NOS: 33 and 34, respectively.

The construction of the backbone vector was as described in Example 2. A fragment from *E. grandis* 4CL cDNA clone (U.S. Pat. No. 6,410,718) was amplified using standard PCR techniques and primers given in SEQ ID NOS: 25 and 26. The primers were designed to add PstI and ClaI restriction sites to both ends of the amplified fragments. The nucleotide sequence of the amplified fragment is given in SEQ ID NO: 27. To clone the 4CL fragment in the sense orientation, the amplified fragment was cut with the restriction enzyme PstI, and cloned into the backbone vector. To clone the 4CL fragment in the antisense orientation, the amplified fragment was digested with ClaI and cloned into the backbone vector.

The complete RNAi cassette (SEQ ID NO: 32) containing the promoter::sense fragment::intron::antisense fragment::3'UTR::nos terminator construct, was removed from the pBluescript plasmid by a NotI restriction digestion, and cloned into the binary vector pART29 (digested with NotI) as described in Example 2 to produce the final vector pAB583.

The final vectors listed in Table 4 were constructed by amplifying four additional fragments (Seq ID NOS 28-31) with primers similarly designed to those used for the fragment in the example above. All five fragments were cloned in the sense and antisense directions into the backbone vector as described above before the complete RNAi cassettes were cloned into pART29 as described above.

TABLE 4

| Final Vector | Fragment cloned in forward and reverse orientation for RNAi | Intron used as spacer |
| --- | --- | --- |
| pARB584 | SEQ ID NO: 28 | SEQ ID NO: 9 |
| pARB585 | SEQ ID NO: 29 | SEQ ID NO: 9 |
| pARB586 | SEQ ID NO: 30 | SEQ ID NO: 9 |
| pARB587 | SEQ ID NO: 31 | SEQ ID NO: 9 |

The vectors listed in Table 5 were constructed using the same methods as those described above, except that the primers SEQ ID NOS: 16 and 17 were used to amplify the PDK intron sequence (Wesley et al., *Plant J.* 27:581-590, 2001) (SEQ ID NO: 15) using standard PCR techniques.

TABLE 5

| Final Vector | Fragment cloned in forward and reverse orientation for RNAi | Intron used as spacer |
| --- | --- | --- |
| pARB578 | SEQ ID NO: 27 | SEQ ID NO: 15 |
| pARB579 | SEQ ID NO: 28 | SEQ ID NO: 15 |
| pARB580 | SEQ ID NO: 29 | SEQ ID NO: 15 |
| pARB581 | SEQ ID NO: 30 | SEQ ID NO: 15 |
| pARB582 | SEQ ID NO: 31 | SEQ ID NO: 15 |

The vectors listed in Table 6 were constructed as described in Example 2 together with the following changes. The yabby intron sequence (Foster et al. 2002, Plant Cell. 14 (7): 1497-

1508) was amplified using primers similarly designed to those for the Pr4CL and PDK intron sequences and cloned into the vector backbone as described in Example 2. The fragment inserts SEQ ID NOS:33 and 34 were amplified with primers similarly designed to those used for the fragments SEQ ID NOS 27-31 in the example above. Substitutions of the promoter from the *Pinus radiata* Superubiquitin promoter plus intron for the *P. taeda* 4CL promoter were done as described in Example 2 where so designated in Table 6 below. The listed fragment insert and promoter were cloned into the final vector as described above in Example 2 before the complete RNAi cassettes were cloned into pART27

TABLE 6

| Final Vector | Promoter driving RNAi cassette | Fragment cloned in forward and reverse orientation around yabby intron spacer for RNAi |
|---|---|---|
| pARB339 | *Pinus radiata* SuperUbiq + Intron (SEQ ID NO: 76) | SEQ ID NO: 33 |
| pARB341 | *Pinus radiata* SuperUbiq + Intron (SEQ ID NO: 76) | SEQ ID NO: 34 |
| pARB345 | *Pinus taeda* 4CL (SEQ ID NO: 77) | SEQ ID NO: 33 |
| pARB347 | *Pinus taeda* 4CL (SEQ ID NO: 77) | SEQ ID NO: 34 |

The final vectors listed in Table 7 were constructed by removing the complete RNAi cassette containing the promoter::sense fragment::intron::antisense fragment::3'UTR::nos terminator construct from the pARB345 final vector listed above by a NotI restriction digestion, and cloning it into either the binary vector pARB1002 or pARB1005 (digested with NotI) using standard cloning techniques.

TABLE 7

| Final Vector | Base Binary Vector into which RNAi cassette was inserted |
|---|---|
| pARB599 | pARB1002 (SEQ ID NO: 61) |
| pARB639 | pARB1005 (SEQ ID NO: 63) |

To modulate the lignin content in *Eucalyptus* plants, constructs comprising various combinations of promoters, first DNA segments and introns can be used. With a selection of constructs from which to choose, a practitioner can obtain plants with the desired amounts of lignin content and growth. Table 8 provides a variety of constructs useful in this regard.

TABLE 8

| Promoter | Fragment | Intron |
|---|---|---|
| *Eucalyptus grandis* COMT 485 bp U.S. Patent Publication No. 20040146904 | Euc 4CL 200 bp fragment (1-200) (SEQ ID NO: 27) | PDK |
| *Eucalyptus grandis* COMT 485 bp U.S. Patent Publication No. 20040146904 | Euc 4CL 223 bp fragment (201-423) (SEQ ID NO: 28) | PDK |
| *Eucalyptus grandis* COMT 485 bp U.S. Patent Publication No. 20040146904 | Euc 4CL 300 bp fragment (551-850) (SEQ ID NO: 29) | PDK |
| *Eucalyptus grandis* COMT 485 bp U.S. Patent Publication No. 20040146904 | Euc 4CL 336 bp fragment (1031-1378) (SEQ ID NO: 30) | PDK |
| *Eucalyptus grandis* COMT 485 bp U.S. Patent Publication No. 20040146904 | Euc 4CL 500 bp fragment (1521-2020) (SEQ ID NO: 31) | PDK |
| *Eucalyptus grandis* COMT 306 bp of U.S. Patent Publication No. 20040146904 | Euc 4CL 200 bp fragment (1-200) (SEQ ID NO: 27) | PDK |
| *Eucalyptus grandis* COMT 306 bp of U.S. Patent Publication No. 20040146904 | Euc 4CL 223 bp fragment (201-423) (SEQ ID NO: 28) | PDK |
| *Eucalyptus grandis* COMT 306 bp of U.S. Patent Publication No. 20040146904 | Euc 4CL 300 bp fragment (551-850) (SEQ ID NO: 29) | PDK |
| *Eucalyptus grandis* COMT 306 bp of U.S. Patent Publication No. 20040146904 | Euc 4CL 336 bp fragment (1031-1378) (SEQ ID NO: 30) | PDK |
| *Eucalyptus grandis* COMT 306 bp of U.S. Patent Publication No. 20040146904 | Euc 4CL 500 bp fragment (1521-2020) (SEQ ID NO: 31) | PDK |
| *Pinus radiata* LIM 1607 bp of U.S. Patent publication No. 20040163146 | Euc 4CL 200 bp fragment (1-200) (SEQ ID NO: 27) | PDK |
| *Pinus radiata* LIM 1607 bp of U.S. Patent publication No. 20040163146 | Euc 4CL 223 bp fragment (201-423) (SEQ ID NO: 28) | PDK |
| *Pinus radiata* LIM 1607 bp of U.S. Patent publication No. 20040163146 | Euc 4CL 300 bp fragment (551-850) (SEQ ID NO: 29) | PDK |
| *Pinus radiata* LIM 1607 bp of U.S. Patent publication No. 20040163146 | Euc 4CL 336 bp fragment (1031-1378) (SEQ ID NO: 30) | PDK |
| *Pinus radiata* LIM 1607 bp of U.S. Patent publication No. 20040163146 | Euc 4CL 500 bp fragment (1521-2020) (SEQ ID NO" 31) | PDK |
| *P. taeda* 4CL (SEQ ID NO: 77) | Euc 4CL 200 bp fragment (1-200) (SEQ ID NO" 27) | PDK |
| *P. taeda* 4CL (SEQ ID NO: 77) | Euc 4CL 223 bp fragment (201-423) (SEQ ID NO" 28) | PDK |
| *P. taeda* 4CL (SEQ ID NO: 77) | Euc 4CL 300 bp fragment (551-850) (SEQ ID NO" 29) | PDK |
| *P. taeda* 4CL (SEQ ID NO: 77) | Euc 4CL 336 bp fragment (1031-1378) (SEQ ID NO" 30) | PDK |
| *P. taeda* 4CL (SEQ ID NO: 77) | Euc 4CL 500 bp fragment (1521-2020) (SEQ ID NO" 31) | PDK |
| *Eucalyptus grandis* COMT 485 bp U.S. Patent Publication No. 20040146904 | Euc 4CL 200 bp fragment (1-200) (SEQ ID NO" 27) | Pr4CL |
| *Eucalyptus grandis* COMT 485 bp U.S. Patent Publication No. 20040146904 | Euc 4CL 300 bp fragment (551-850) (SEQ ID NO" 29) | Pr4CL |
| *Eucalyptus grandis* COMT 485 bp U.S. Patent Publication No. 20040146904 | Euc 4CL 500 bp fragment (1521-2020) (SEQ ID NO" 31) | Pr4CL |
| *Eucalyptus grandis* COMT 306 bp of U.S. Patent Publication No. 20040146904 | Euc 4CL 200 bp fragment (1-200) (SEQ ID NO: 27) | Pr4CL |
| *Eucalyptus grandis* COMT 306 bp of U.S. Patent Publication No. 20040146904 | Euc 4CL 300 bp fragment (551-850) (SEQ ID NO: 29) | Pr4CL |
| *Eucalyptus grandis* COMT 306 bp of U.S. Patent Publication No. 20040146904 | Euc 4CL 500 bp fragment (1521-2020) (SEQ ID NO: 31) | Pr4CL |
| *Pinus radiata* LIM 1607 bp of U.S. Patent publication No. 20040163146 | Euc 4CL 200 bp fragment (1-200) (SEQ ID NO: 27) | Pr4CL |
| *Pinus radiata* LIM 1607 bp of U.S. Patent publication No. 20040163146 | Euc 4CL 300 bp fragment (551-850) (SEQ ID NO: 29) | Pr4CL |
| *Pinus radiata* LIM 1607 bp of U.S. Patent publication No. 20040163146 | Euc 4CL 500 bp fragment (1521-2020) (SEQ ID NO: 29) | Pr4CL |
| Euc LIM of U.S. Patent publication No. 20040163146 | Euc 4CL 200 bp fragment (1-200) (SEQ ID NO: 27) | Pr4CL |
| Euc LIM of U.S. Patent publication No. 20040163146 | Euc 4CL 300 bp fragment (551-850) (SEQ ID NO: 29) | Pr4CL |

TABLE 8-continued

| Promoter | Fragment | Intron |
|---|---|---|
| Euc LIM of U.S. Patent publication No. 20040163146 | Euc 4CL 500 bp fragment (1521-2020) (SEQ ID NO: 31) | Pr4CL |
| P. taeda 4CL (SEQ ID NO: 77) | Euc 4CL 200 bp fragment (1-200) (SEQ ID NO: 27) | Pr4CL |
| P. taeda 4CL (SEQ ID NO: 77) | Euc 4CL 300 bp fragment (551-850) (SEQ ID NO: 29) | Pr4CL |
| P. taeda 4CL (SEQ ID NO: 77) | Euc 4CL 500 bp fragment (1521-2020) (SEQ ID NO: 31) | Pr4CL |

Example 4

Isolation of cDNAs of E. Grandis CCoAOMT, C3H, C4H and CCR

Two Eucalyptus grandis cDNA expression libraries (one from a mixture of various tissues from a single tree and one from leaves of a single tree) were constructed and screened as follows.

mRNA was extracted from the plant tissue using the protocol of Chang et al. (Plant Molecular Biology Reporter 11:113-116, 1993) with minor modifications. Specifically, samples were dissolved in CPC-RNAXB (100 mM Tris-C1, pH 8.0; 25 mM EDTA; 2.0 M NaCl; 2% CTAB; 2% PVP and 0.05% Spermidine*3HCl) and extracted with chloroform: isoamyl alcohol, 24:1. mRNA was precipitated with ethanol and the total RNA preparation was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequences for positive clones were obtained using a Perkin Elmer/Applied Biosystems Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

The determined cDNA sequences were compared to known sequences in the EMBL database (release 46, March 1996) using the FASTA algorithm of February 1996 (Version 2.0.4) or the BLAST algorithm Version 2.0.4 [Feb. 24, 1998], or Version 2.0.6 [Sep. 16, 1998]. Multiple alignments of redundant sequences were used to build up reliable consensus sequences. Based on similarity to known sequences from other plant species, the isolated polynucleotides of the present invention were identified as encoding a specified enzyme.

Using the procedures described above, cDNA sequences derived from the Eucalyptus grandis library encoding the following polypeptides were isolated: caffeoyl CoA methyl transferase (U.S. Pat. No. 6,410,718); cinnamate-4-hydroxylase (C4H) (U.S. Pat. No. 6,410,718); p-coumarate-3-hydroxylase (C3H) (U.S. Pat. No. 5,981,837) and CCR (U.S. Pat. No. 6,410,718).

Example 5

Construction of Pinus radiata LIM Expression Vectors

The final vectors listed in Table 9 were constructed as described in Example 2 with the following modifications; the use of different fragments, promoters and/or introns. Two fragments SEQ ID NOS: 38 &39) from the P. radiata LIM cDNA clone (patent application WO 00/53724) were amplified using standard PCR techniques and primers similarly designed to those used in Example 2. The P. radiata LIM fragments were cloned into the backbone vector in both the sense and antisense orientations as described in Example 2. Final vectors in Table 9 containing a different promoter to that contained in the backbone vector were constructed by making changes to the promoter similarly to that described in Example 2. The yabby intron was inserted into the final vectors using the method described in Example 2. The complete RNAi cassettes were cloned into pART27 or pART29 as described in examples 1 and 2.

TABLE 9

| Final Vector | Binary Vector into which the RNAi cassette was inserted | Promoter driving the RNAi cassette | Fragment cloned in forward and reverse orientation in RNAi cassette |
|---|---|---|---|
| pARB348 | pART27 | Pinus radiata SuperUbiq + Intron (SEQ ID NO: 76) | SEQ ID NO: 38 |
| pARB352 | pART27 | Pinus taeda 4CL (SEQ ID NO: 77) | SEQ ID NO: 38 |
| pARB349 | pART27 | Pinus radiata SuperUbiq + Intron (SEQ ID NO: 76) | SEQ ID NO: 39 |
| pARB353 | pART27 | Pinus taeda 4CL (SEQ ID NO: 77) | SEQ ID NO: 39 |
| pARB235 | pART29 | Pinus radiata SuperUbiq + Intron (SEQ ID NO: 76) | SEQ ID NO: 38 |
| pARB236 | pART29 | Pinus radiata SuperUbiq + Intron (SEQ ID NO: 76) | SEQ ID NO: 39 |
| pARB243 | pART29 | Pinus taeda 4CL (SEQ ID NO: 77) | SEQ ID NO: 38 |
| pARB244 | pART29 | Pinus taeda 4CL (SEQ ID NO: 77) | SEQ ID NO: 39 |

To utilize vectors based on pART27 in pine, the constructs must be re-engineered to remove the selection cassette nos:: nptII. As described in Example 2, NotI fragments can be removed and inserted into a base vector that has a NotI site as well as a constitutive promoter expression GUS, to allow verification of transformation without PCR, and a selectable marker cassette comprising nptII driven by the Arabidopsis Ubq 10 promoter. The vector pWVR31 can be used as a new base vector.

Example 6

Construction of *Eucalyptus Grandis* LIM Expression Vectors

The construction of the backbone plasmid was as described in Example 2. Two fragments (SEQ ID NOS: 40 & 41) from *E. grandis* LIM cDNA clone (patent application WO00/53724) were amplified using standard PCR techniques and primers designed to add EcoRI and XbaI restriction sites to both ends of the amplified fragments. To clone the LIM fragments in the sense orientation, the amplified fragments were cut with the restriction enzymes EcoRI and XbaI, blunt ended using Klenow and cloned into the backbone vector containing the yabby intron and *P. radiata* superubiquitin promoter sequence (described in Example 2) in a blunt-ended ClaI site. To clone the LIM fragments in the antisense orientation, the amplified fragments were cut with the restriction enzymes EcoRI and XbaI, blunt ended using Klenow and cloned into the same backbone vector in a blunt-ended PstI site using standard cloning techniques.

The complete RNAi cassette containing the promoter::sense fragment::intron::antisense fragment::3'UTR::nos terminator construct, was removed from the backbone vector by a NotI restriction digestion, and cloned into the binary vector pART29 (digested with NotI) using standard cloning techniques. For final vectors containing a different promoter as listed in Table 10, the promoter sequence was substituted using the method described in Example 2. The vectors listed in Table 10 were constructed using this method.

TABLE 10

| Final Vector | Promoter driving the RNAi cassette | Fragment cloned in forward and reverse orientation in RNAi cassette |
| --- | --- | --- |
| pARB489 | *Pinus radiata* SuperUbiq + Intron (SEQ ID NO: 76) | SEQ ID NO: 40 |
| pARB490 | *Pinus radiata* SuperUbiq + Intron (SEQ ID NO: 76) | SEQ ID NO: 41 |
| pARB491 | *Pinus taeda* 4CL (SEQ ID NO: 77) | SEQ ID NO: 40 |
| pARB492 | *Pinus taeda* 4CL (SEQ ID NO: 77) | SEQ ID NO: 41 |

Example 7

Construction of Pine CCoAOMT Expression Vector

The following vector was cloned as described in Example 2, with the modification that a fragment from the Pine CCoOMT (caffeoyl-coenzyme O-Methyltransferase) (SEQ ID NO: 42) clone was amplified with primers similarly designed to those used in Example 2 and used in a method in accordance to that described in Example 2. The final vector was also modified by the addition of the yabby intron and the use of the pART27 binary vector using the methods described in Example 2.

TABLE 11

| Final Vector | Promoter | Fragment |
| --- | --- | --- |
| pARB357 | *Pinus radiata* SuperUbiq + Intron (SEQ ID NO: 76) | SEQ ID NO: 42 |

To utilize the vector in pine, the construct must be re-engineered to remove the selection cassette nos::nptII. As described in Example 2, NotI fragments can be removed and inserted into a base vector that has a NotI site as well as a constitutive promoter expression GUS, to allow verification of transformation without PCR, and a selectable marker cassette comprising nptII driven by the *Arabidopsis* Ubq10 promoter. The vector pWVR31 can be used as a new base vector.

Example 8

Construction of Additional Pine CCoAOMT Expression Vectors

The following vectors were cloned as described in Example 3, with the modifications that a fragment from the Pine CCoAOMT (Caffeoyl-coenzyme A O-Methyltransferase) (SEQ ID NO: 43) clone (isolated in Example 4) was amplified with primers similarly designed to those used in Example 4 and used in a method in accordance to that described in Example 4. The final vectors were also modified by means of the addition of the PDK intron, the use of either the *P. radiata* Superubiquitin promoter with intron or the *P. taeda* 4CL promoter and the use of the pWVK147 binary vector using the methods described above.

TABLE 12

| Final Vector | Promoter | Fragment |
| --- | --- | --- |
| pARB559 | *Pinus radiata* SuperUbiq + Intron (SEQ ID NO: 76) | SEQ ID NO: 43 |
| pARB560 | *Pinus taeda* 4CL (SEQ ID NO: 77) | SEQ ID NO: 43 |

Example 9

Construction of *E. Grandis* CCoAOMT Expression Vectors

The following vectors were cloned as described in Example 3, with the modifications that a fragment from the *E. grandis* CCoAOMT (Caffeoyl-coenzyme A O-Methyltransferase) (SEQ ID NO: 44) clone (isolated in Example 4 filed as partial sequence in WO98/11205) was amplified with primers similarly designed to those used in Example 3 and used in a method in accordance to that described in Example 3. The final vectors were also modified by the addition of the PDK intron or the *Eucalyptus* xylem intron, the *E. grandis* COMT promoter and the use of the pART29 binary vector using the methods described in Example 3.

TABLE 13

| Final Vector | Fragment | Intron |
| --- | --- | --- |
| pARB523 | SEQ ID NO: 44 | SEQ ID NO: 15 |
| pARB524 | SEQ ID NO: 44 | *Eucalyptus* Xylem intron |

Example 10

Construction of *E. Grandis* CCR Expression Vectors

The following vectors were cloned as described in Example 3, with the modifications that a fragment from the *E.*

*grandis* CCR (cinnamoyl CoA reductase) clone (SEQ ID NO: 45) (isolated in Example 4) was amplified with primers similarly designed to those used in Example 3 and used in a method in accordance to that described in Example 3. The final vectors were also modified by the addition of the PDK intron or the *Eucalyptus* xylem intron, the *E. grandis* COMT promoter 485 bp fragment of U.S. patent application Ser. No. 10/703,091 and the use of the pART29 binary vector using the methods described in Example 3.

TABLE 14

| Final Vector | Fragment | Intron |
|---|---|---|
| pARB525 | SEQ ID NO: 45 | SEQ ID NO: 15 |
| pARB526 | SEQ ID NO: 45 | *Eucalyptus* Xylem intron from patent WO00/22092 |

Example 11

Construction of *E. Grandis* C3H and C4H Expression Vectors

The following vectors were cloned as described in Example 3, with the modifications that the fragments from the *E. grandis* C3H clones (isolated in Example 4) (SEQ ID NO: 46) or *E. grandis* C4H (SEQ ID NO: 47) clones (isolated in Example 4; filed as partial sequence in WO00/22099) amplified with primers similarly designed to those used in example 2 and used in a method in accordance to that described in Example 3. Either the Arabinogalactan promoter from *E. grandis* (SEQ ID NO: 35) or the 4CL promoter from *P. taeda* (U.S. Pat. No. 6,252,135) was used in these vectors. The *P. radiata* superubiquitin promoter intron vector was digested with the BamHI restriction enzyme and, using standard techniques, cloned into Bluescript vectors containing either a 4CL promoter from *P. taeda* (digested with BamHI), or the Arabinogalactan promoter from *E. grandis* (digested with ClaI). The *P. taeda* 4CL promoter and the *E. grandis* Arabinogalactan promoter were both amplified using primers similarly designed to those used to amplify the *P. radiata* superubiquitin promoter sequence with intron and then ligated into the base Bluescript vector as described in Example 3. The final vector was also modified by the addition of the Pr4CL intron, and the use of the pARB1002 binary vector, using the methods described in Example 3.

TABLE 15

| Final Vector | Promoter | Fragment |
|---|---|---|
| pARB669 | *Eucalyptus grandis* Arabinogalactan 2446 bp (SEQ ID NO: 35) | SEQ ID NO: 46 |
| pARB670 | *Eucalyptus grandis* Arabinogalactan 2446 bp (SEQ ID NO: 35) | SEQ ID NO: 47 |
| pARB672 | *Pinus taeda* 4CL (SEQ ID NO: 77) | SEQ ID NO: 47 |

Example 12

Evaluation of 4CL constructs in *Eucalyptus*

Three different constructs containing RNAi fragments of two different lengths, pARB339, pARB341 and pARB345 (see Table 16) were transformed into *Eucalyptus* grandis using the following procedure.

TABLE 16

| DNA Construct Name | Construct description |
|---|---|
| pARB339 | constitutive promoter driving 4CL RNAi 200 bp fragment |
| pARB341 | constitutive promoter driving 4CL RNAi 600 bp fragment |
| pARB345 | vascular-preferred promoter driving 4CL RNA1 200 bp fragment |

Clonal *Eucalyptus grandis* leaf explants micropropagated in culture on elongation media—(MS with 1 µM BAP, 20 g/L sucrose and 7 g/L agar) were used for transformation. Transformation was carried out as described in Burrel et. al. International publication number WO00/12715, which is hereby incorporated by reference.

Transgenic explants were selected as described in WO00/12715 except that NAA was omitted, and media contained 50 mg/L kanamycin and 250 mg/L timentin. Explants remained on this medium for two weeks, and were then transferred to media containing 100 mg/L kanamycin and 250 mg/L timentin after 2 weeks, and media containing 150 mg/L kanamycin and 250 mg/L timentin after another two weeks. Cultures were then transferred on a monthly basis to fresh media containing 150 mg/L kanamycin and 250 mg/L timentin until healthy single shoots could be collected. Single shoots were placed onto elongation media to proliferate the putative transgenic tissue. When approximately 200 mg of tissue could be collected from the proliferating tissue, this was removed from the primary explant for PCR analysis. PCR analysis for both the presence of the promoter and selection gene was carried out using the PuRe Taq Ready-To-Go™ PCR beads (Amersham Biosciences), according to the manufacturer's instructions.

Tissues with positive PCR results were then proliferated further on elongation medium containing 150 mg/L kanamycin and 250 mg/L Timentin, and maintained as stock cultures.

To generate transgenic plants for further testing, some shoots were placed onto an elongation medium. Shoots were maintained on this medium until they were approximately 2-3 cm tall. If this took more than 1 month shoots were placed onto fresh medium at monthly intervals. Once shoots were 2-3 cm tall, single shoots were removed and placed into a rooting medium. After 10 days in rooting medium plants were transferred to the greenhouse. Those skilled in the art of plant transformation and plant tissue culture will recognize that many different culture media and intervals may be suited to regenerating plants of the instant invention.

Plants were grown in the greenhouse for six months in potting mixture, using an appropriate humidity regime and fungicides to control fungal growth. Plants were grown in a meshed compartment at ambient temperature with capillary watering. Plants were potted into 5 L poly-bags in s soil-less peat based compost supplemented with a slow release fertilizer.

Plants at approximately six months of age were destructively sampled for total lignin analysis.

Height Measurements

Table 17 lists the percentage of micropropagated plants selected with the use of kanamycin that survived in soil after six months, the percentage of dwarfed plants observed at 20 weeks after being planted in soil and average height of plants at 22 weeks after being planted in soil of *Eucalyptus* plants transformed with pARB339, pARB341 or pARB345.

Survival data of plants transformed with pARB341 was much lower than that of plants transformed with pARB339 or pARB345. Of all the plants transformed with pARB341 that survived, 82% were dwarfed suggesting that the DNA vector pARB341 affected the height and survival rate of the plants, to a greater extent than the other two vectors (pARB339 and pARB345).

TABLE 17

| Construct | % Survived after 6 months | % plants dwarfed at 20 weeks | Mean height of plants analyzed for lignin content at 22 weeks (cm) |
|---|---|---|---|
| pARB339 | 95 | 2.8 | 117 |
| pARB341 | 38 | 82 | 13 |
| pARB345 | 83 | 2.9 | 127 |

Figure 2A:
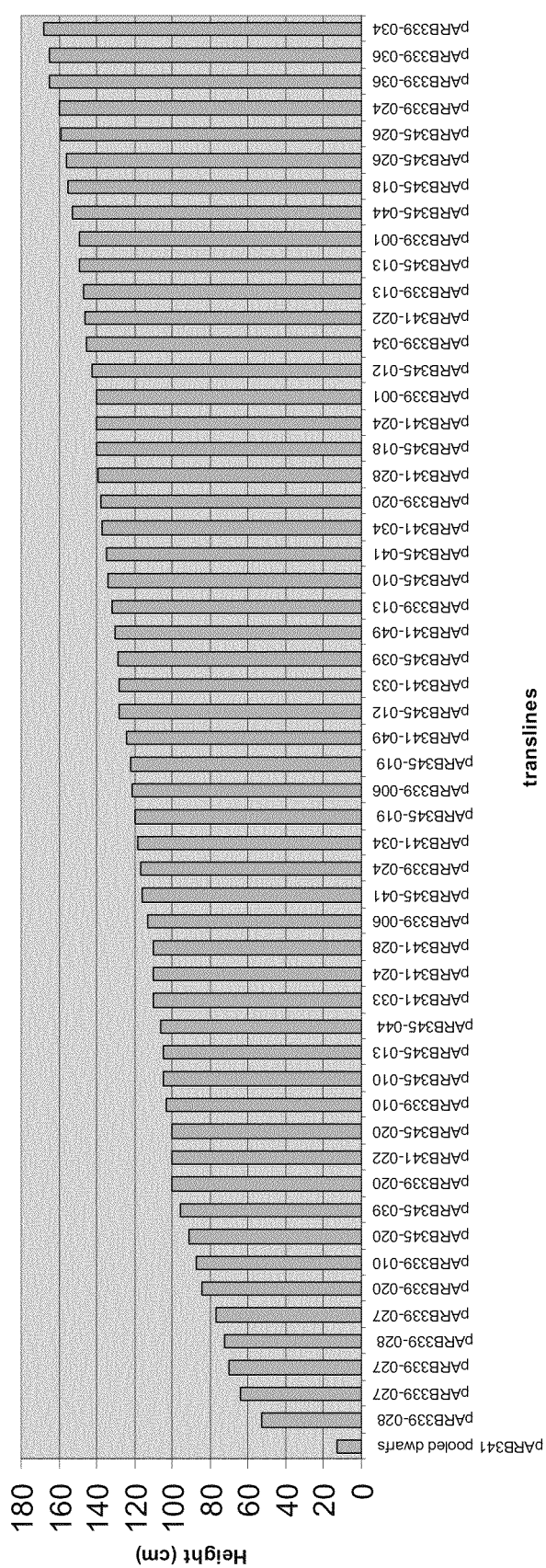

The data presented in FIGS. 1 and 2A demonstrate the apparent effect of each construct on plant height. While the tallest individual plants in each set of plants transformed with pARB345 and pARB339 are close (159 and 168 cm, respectively) the shortest pARB339 plants (53 cm, 64 cm) are much shorter than the shortest pARB345 plants (91 cm, 96 cm). This figure does not include the average height of the dwarf pARB341 samples that were pooled for analysis. The average height of the dwarf pARB341 plants was 13 cm.

Lignin Analysis

Figure 2B:
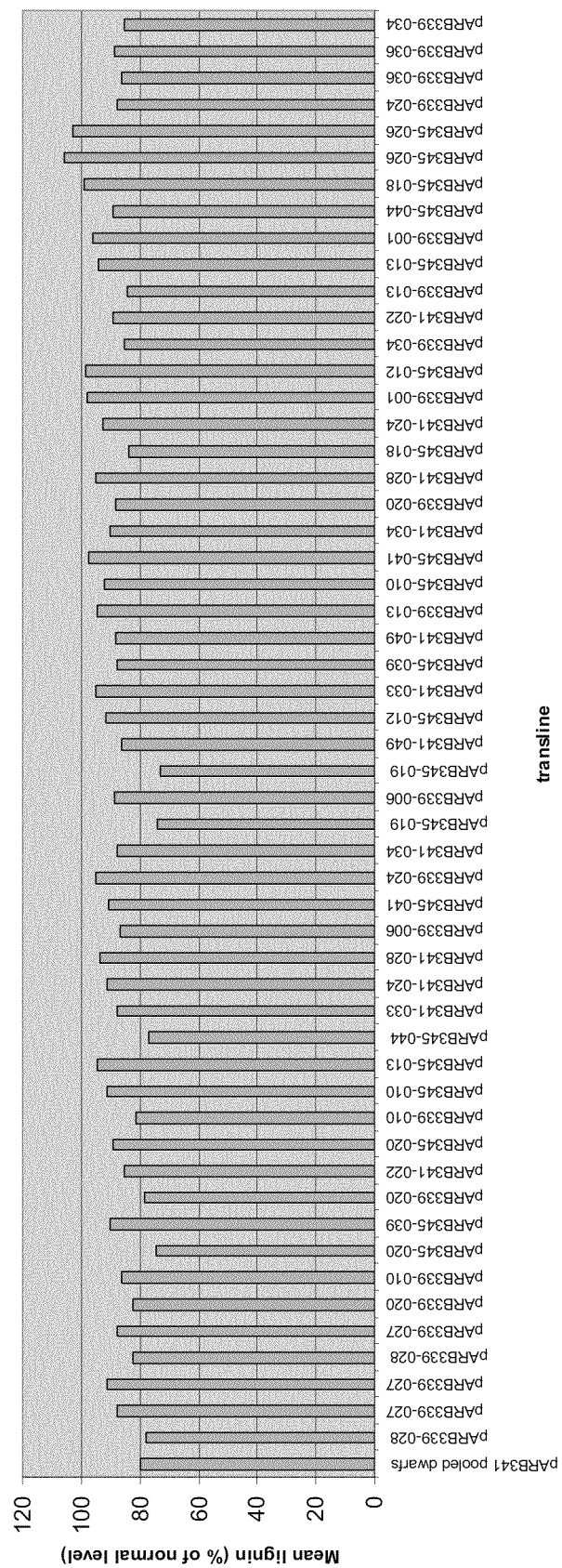
FIG. 2B depicts the mean lignin content of the transgenic trees.

Transgenic *Eucalyptus* trees generated as described in the previous example were sampled for lignin analysis at approximately six months of age. The bottom 20 cm of the stem was collected from all the samples to be analyzed. The bark, phloem and the primary cortex was removed from the stem by peeling, and the stem samples were then flash frozen in liquid nitrogen. Frozen samples were freeze-dried in a Flexi-Dry Microprocessor control—corrosion resistant freeze-drier (Stone Ridge, N.Y., USA) according to the manufacturer's instructions. Samples were ground in a Wiley Mill (Arthur H. Thomas Co,; Philadelphia, U.S.A.) and then re-ground in a ring mill. Ground samples were then dried for a minimum of 1 day at 55° C. and stored at this temperature until used. Cell wall material was isolated from the samples in a series of stages by suspending the ground material in the solvent or solution, extracting with an ultrasonic cleaner, centrifuging and then decanting off the supernatant. The following sequence of extractions was used: NaCl at two concentrations, aqueous ethanol; $CHCl_3$:MeOH; and acetone. To remove the starch, the extracted cell wall materials were washed, heated in tris-acetate buffer to gelatinize the starch and then treated with α-amylase. Following enzyme treatment the suspension was centrifuged and the resulting precipitate washed with ethanol and acetone, allowed to stand overnight, and then dried at 55° C. The isolated cell material was used for small scale lignin determinations carried out using the procedure described in Fukushima, R. S. and Hatfield, R. D. (2001) *J. Ag. Food Chem.* 49(7):3133-9. Results are shown in FIGS. 2A and 2B The RNAi cassette in pARB341 resulted in 82% of all transformed plants to be dwarfed. A pooled sample of these plants showed that they had reduced lignin levels, to approximately 80% of normal levels. This vector had the greatest effect on plant height when compared to the other two vectors tested and also a large effect on reducing lignin levels. While the extreme end of the lignin-reduction ranking features dwarf phenotypes, the lowest-lignin transline of all identified in this study, a pARB345 transline, has reasonably normal height. Hence the dwarfism seen in many of the pARB341 transformants may be a separate phenomenon caused by suppression of genes other than the 4CL gene expressed in lignifying secondary xylem, for example 4CL genes expressed in other parts of the plant or genes with partial homology to 4CL.

The RNAi cassette in pARB345 was found to be more effective than that in pARB339 at producing phenotypes with significantly reduced lignin. The 200 bp RNAi cassette in pARB345 is capable of inducing lignin reductions up to −25% without also triggering the dwarfing effect induced in many transformants by the 600 bp RNAi cassette driven by the same promoter in pARB341.

Nine plants transformed with pARB345 were selected from the lignin analysis above and a second 20 cm stem sample harvested from above the first were submitted for lignin content determination using pyrolysis molecular beam mass spectrometry and by solid-state $^{13}C$ NMR for comparison of methods. All three methods gave approximately the same values for lignin reduction.

For pyrolysis molecular beam mass spectrometry, each sample was weighed in a quartz boat, and pyrolyzed in a reactor consisting of a quartz tube (2.5 cm inside diameter) with helium flowing through at 5 L/min (at STP). The reactor tube was placed such that the sampling orifice of the molecular-beam mass spectrometer was inside the end of the quartz reactor. A molecular-beam mass spectrometer using a Extrel™ Model TQMS C50 mass spectrometer was used for pyrolysis vapor analysis as described in Evans & Milne (1987) (Energy & Fuels, 1: 123-37). The reactor was electrically heated and its temperature maintained at 550° C. Total pyrolysis time was 90 seconds although the pyrolysis reaction was completed in less than 50 seconds. The residence time of the pyrolysis vapors in the reactor pyrolysis zone has been estimated to be ~75 ms and is short enough that secondary cracking reactions in the quartz reactor are minimal. Mass spectral data from 20-450 Da were acquired on a Teknivent Vector 2™ data acquisition system using 22 eV electron impact ionization. Using this system, both light gases and heavy tars were sampled simultaneously and in real time. The mass spectrum of the pyrolysis vapor provides a rapid, semi-quantitative depiction of the molecular fragments.

Principal component analysis of the pyMBMS spectra using a mass range between m/z 50 and 200 highlighted pyrolysis products from lignin and carbohydrates while minimizing small pyrolysis and electron impact fragments (below m/z 50) and extractives (above m/z 200).

For NMR determination of lignin content, high-resolution, solid-state $^{13}C$ NMR spectra were collected at 4.7 T with cross-polarization (CP) and magic angle spinning (MAS) in a Bruker Avance 200 MHz spectrometer. Variable amplitude cross-polarization (1 db linear ramp over cross polarization period) was used to minimize variations of the nonprotonated aromatic carbons that are sensitive to Hartmann-Hahn mismatch at higher MAS rotation rates (S. O Smith, I. Kustanovich, X. Wu, O. B. Peersen, Journal of Magenetic Resonance (1994) 104: 334-339). $^1H$ and $^{13}C$ fields were matched at 53.6 kHz and a 1 dB ramp was applied to the proton r.f. during the matching period. Acquisition time was 0.033 seconds and sweepwidth was 31.3 kHz. Magic-angle spinning was performed at a rate of 7000 Hz. 2000-4000 scans were averaged using a 2 ms contact time and a pulse repetition rate of 1.0 sec. Differences observed in relative peak intensities and integrated areas can be used to identify differences between similar samples. Weight % lignin values were calculated from the integrated areas of the aromatic (110 ppm-160 ppm) and carbohydrate (40 ppm-100 ppm) region using the method of Haw et at 1984 (J. F. Haw., G. E. Maciel., H. A. Schroder, Analytical Chemistry 56: 1323).

Data analysis was performed using the Unscrambler version 7.8 software program (CAMO A/S, Trondheim, Norway). The Projection to Latent Structure (PLS-1) algorithm, which handles only one Y-variable at a time, was used to construct the model for predicting the lignin contents of the pine samples. The lignin content predictive model was developed using the pyMBMS spectra as the X-matrix (310 variables (m/z values between 50 and 360)) and the lignin values measured by solid-state NMR as the Y-matrix. The mass spectra were normalized to the total ion current before analysis. Model validation was performed using full cross validation which systematically removes one sample from the data, establishes a model with the remaining samples and then uses that model to predict the value of the Y-variable of the samples that was removed from the data set. The process continues until all samples have been removed and predicted from the Y-matrix. The goodness-of-fit (i.e., a high correlation coefficient) and minimal residual error were the criteria used for choosing the best model.

A PLS 1 model to predict lignin content was constructed from the NMR lignin values and the pyMBMS spectra. In cases where more than one tree from the same line was sampled for the NMR analysis, the corresponding mass spectra from the trees were averaged and used to build the model. A PLS model was constructed using a range of m/z values from 50 to 360. This range was determined empirically to provide the best model based on the correlation coefficient of the fully cross-validated model. The final fully cross-validated model shown in FIG. 4, had a RMSEP of 0.9 and an $r^2$ value of 0.94.

Table 18 shows a comparison of the NMR results for the nine selected samples. Comparison of the NMR wt % lignin values with the PC1 scores for the selected samples show that the PC1 scores accurately reflect the amount of lignin in the loblolly pine samples and the PC1 scores can be used to rank the lignin content of the different constructs. There is also excellent correlation between the NMR-determined lignin content and the content as determined by acetyl bromide as described above.

Histochemical tests for lignin, which detects coniferaldehyde units using phloroglucinol/HCl, were applied to hand sections taken from side branches from transgenic plants containing the DNA constructs of the instant invention. Phloroglucinol, also known as the Weisner reagent, is a stain for lignin (Pomar et al., *Protoplasma,* 220(1-2):17-28 (2002), and Maule stain is used to detect specifically syringyl lignin subunits (Lewis et al., *Annu Rev Plant Physiol Plant Mol Biol,* 41:455-496 (1990). Transgenic plants transformed with pARB339 and pARB345 showed no observable difference to control untransformed plants. Normal height pARB341 plants also had no observable difference to control plants, whereas dwarf pARB341 plants had a reduced amount of phloroglucinol staining, suggesting that lignin levels were greatly reduced in these samples. Examination of stained sections of the dwarf pARB341 translines showed that there was transline-to-transline variation. Two ramets of one dwarf transline with a particularly extreme anatomical phenotype were highly consistent in their appearance, suggesting the observed perturbations in lignin deposition and anatomy have a (trans)genetic basis. Hand cut sections of dwarf and normal sized pARB341 plants were also stained with Maule stain This stain is specific for subunits of syringyl lignin (Strivastava LM. 1966. Histochemical studies on lignin. Tappi Journal 49:173-183).

As with sections stained with phloroglucinol, there was dramatically less lignin observed in the dwarf plants than the "normal" plants and a lack of vascular differentiation in the stems of the dwarf plants was evident.

Dwarf pARB341 plants were also phenotypically different to their tall counterparts because they had wood that was a pink colour. This was observed once the stems were peeled. The stems of these plants were also soft and rubbery compared to the tall plants. Interestingly a few pARB345 plants with a tall/"normal" phenotype also had pink wood when the bark, phloem and primary cortex were peeled off.

Two wild-type samples and 10 transgenic samples were examined by confocal microscopy. The 10 transgenic samples examined included 5 pARB339 plants, one with pink wood, 2 dwarf pARB341 plants, both with pink wood, and 3 pARB345 plants, 2 of which had pink wood. Stem segments 2-3 cm long were fixed in formalin aceto-alcohol (FAA). Samples were washed in water and sectioned at a thickness of

TABLE 18

| *Eucalyptus grandis* clone, construct and event number | Pyrolysis molecular beam mass spectrometry data analysis | | | | NMR lignin values | Average Lignin (%) determined by Acetyl Bromide method |
|---|---|---|---|---|---|---|
| | Average PC1 | Deviation | Average PC2 | Deviation | | |
| 824.019 pARB345-002-3 | 2.8335 | 0.287792 | −0.567 | 0.100409 | 14.1 | 15.83 |
| 824.019 pARB345-014-1 | −3.4605 | 1.069853 | −0.7475 | 0.245366 | 19.5 | 20.05 |
| 824.019 pARB345-015-2 | −0.568 | 1.52028 | 0.11718 | 0.115711 | 17 | 16.22 |
| 824.019 pARB345-026-1 | −2.5165 | 2.181424 | 0.5005 | 2.085258 | 19.1 | 20.6 |
| 824.019 pARB345-033-1 | −4.819 | 0.254558 | −1.0015 | 0.939745 | 20.1 | 19.24 |
| 824.019 pARB345-034-3 | 2.395 | 0.588313 | 0.5765 | 0.420729 | 14.4 | 15.86 |
| 824.019 pARB345-039-2 | −0.435 | 1.200667 | 0.65 | 0.767918 | 15.7 | 18.1 |
| 824.019 pARB345-041-5 | −1.43831 | 1.897436 | −0.259 | 0.690136 | 19.9 | 19.5 |
| 824.019 pARB345-044-1 | 1.4815 | 1.8109 | 3.008 | 0.95318 | 14.9 | 15.4 |

30-60 mm using a sledge microtome. Sections were stained using safranin and phloroglucinol/HCl for anatomical analysis using the confocal microscope. Some samples were examined with toluidine blue stain.

All of the samples contained large and varying amounts of tension wood, present in patches often only on one side of the stem. This was characterized by extremely thick walled fibres with a more or less unlignified secondary wall. In tension wood in all samples, reduction in lignification was confirmed by a reduction in red coloration by phloroglucinol/HCl, and increase in green fluorescence with safranin staining, and by a pink staining with toluidine blue. To distinguish a transgenic phenotype from the tension wood effect, in all samples the areas of stem that were normal wood, that did not show the staining pattern typical of tension wood were examined using confocal microscopy with safranin staining, and also using phloroglucinol/HCl staining. There were no obvious indications of altered cell wall composition in normal fibres or vessels in most of the samples. Two samples from pARB341 transgenic trees showed an anatomical phenotype indicative of altered cell wall composition: a significant reduction in vessel diameter and a wavy appearance of the vessel cell walls. At least one of these samples also showed changes outside of the xylem (lignified tissues in the pith). However, it is notable that samples from the non-dwarf, low-lignin samples identified above did not show anatomical abnormalities detectable by confocal microscopy. The results demonstrate that the constructs of the instant invention can give rise to a variety of combinations of height growth, reduced lignin content, and altered anatomical phenotype. Thus, the disclosed methods enable the generation and selection of transgenic trees that exhibit the most desirable combinations of phenotypes for pulp production or other wood-derived products.

Example 13

Evaluation of 4CL Constructs in Loblolly Pine

Lignin Evaluation using PyMBMS

Loblolly pine (*Pinus taeda*) and hybrid pine (*P. taeda*×*P. rigida*) embryogenic cell lines were initiated from zygotic embryos of individual immature megagametophytes using the procedures described in U.S. Pat. No. 5,856,191, and maintained using the procedures described in U.S. Pat. No. 5,506,136.

After one to three months of culture on maintenance medium, the tissue cultures were cryopreserved, stored for periods of up to several years, and then retrieved using the methods of U.S. Pat. No. 6,682,931. Those skilled in the art of plant tissue culture will recognize that other cryopreservation and recovery protocols would be applicable to the present method and that the detail in this example may not be construed to limit the application of the method.

Uniform suspension cultures from each of the genetically different tissue culture lines were established by inoculating a 250 ml Nephelo sidearm flask (Kontes Chemistry and Life Sciences Products) with 1 g of tissue each according to the method of U.S. Pat. No. 5,491,090. The flasks containing the cells in liquid medium were placed on a gyrotory shaker at 100 rpm in a dark culture room at a temperature of $23°$ C.$\pm 2°$ C. One week later, the liquid in each flask was brought to 35 ml by pouring 15 ml fresh medium into the culture flask and swirling to evenly distribute the cells. Cell growth was measured in the sidearm by decanting cells and medium into the sidearm portion of the flasks, allowing the cells to settle for 30 minutes and then measuring the settled cell volume (SCV). When the SCV was greater than or equal to half the maximal SCV (50% of the volume of the flask was occupied by plant cells), each culture was transferred to a 500 ml sidearm flask containing a total of 80 ml cells and medium and the transferred culture was maintained under the same conditions.

To prepare for gene transfer, polyester membrane supports were sterilized by autoclaving and placed in separate sterile Buchner funnels, and for each of six replicate plates per cell line, one to three milliliters of pine embryogenic suspension was pipetted onto each support such that the embryogenic tissue was evenly distributed. The liquid medium was suctioned from the tissues and each support bearing the embryogenic tissue was placed on gelled preparation medium for *Agrobacterium* inoculation according to the methods described in U.S. Patent Publication No. 20020100083. Specifically, the binary constructs pWVC60, pWVC62, pWVK158, pWVK154, pWVK157, pWVK155, pWVK143, pWVC46, pWVC40, pWVC43, and pWVC44 were each introduced into different isolates *Agrobacterium tumefaciens* by techniques well known to those skilled in the art, and virulence was induced with administration of acetosyringone by commonly used techniques whereupon each of the induced *Agrobacterium* isolates was co-mingled with separate replicates of the plant material. The cells were co-cultivated in the dark at $22°\pm 2°$ C. for approximately 72 hours.

Following co-cultivation, *Agrobacterium* was eradicated from the cultures according to the methods described in U.S. Patent Publication No. 20020100083. Cells borne on polyester membrane supports were then transferred onto fresh selection media at intervals of 2 weeks. Active growth on the selection medium occurred in a number of isolated sectors on many of the petri dishes. Such active growth in the presence of selection agent is normally an indication that the growing tissues have integrated the selection gene into their chromosomes and are stably transformed. These areas of active growth are treated as independent transformation events and are henceforth referred to as putative transgenic sublines. The putatively transgenic embryogenic tissue was multiplied by transferring growing transgenic sectors to fresh semi-solid maintenance medium supplemented with the respective selection agent.

Putatively transformed sublines, after reaching approximately 2 g, were chosen for polymerase chain reaction (PCR) amplification for verification of the presence of transgenes using standard techniques.

TABLE 19

Primer Pairs for PCR (SEQ ID NOS 68-75 respectively in order of appearance)

| | | |
|---|---|---|
| virD2 | GAA GAA AGC CGA AAT AAA GAG G | Product |
| virD2 | TTG AAC GTA TAG TCG CCG ATA G | size |
| | These primers were used to check contamination by *Agrobacterium* | 560 |
| NptII | AAG GAG ATA TAA CAA TGA TTG AAC AAG ATG GAT TGC | |
| NptII | TCA GAA GAA CTC GTC AAG AAG G | 800 |
| | | 800 |

TABLE 19-continued

Primer Pairs for PCR (SEQ ID NOS 68-75 respectively in order of appearance)

| | | |
|---|---|---|
| uid(gus) | CGA AAA CGG CAA GAA AAA GCA G | |
| uid(gus) | ACG ACC AAA GCC AGT AAA GTA G | |
| | | 450 |
| Pal | AAT GGG AAG CCT GAG TTT ACA | |
| Pal | GGC CAG CAT GTT TTC CTC CAG | |
| | These primers, for the PAL gene, were used as a positive control | 700 |

Material from each subline also was sacrificed for GUS staining and microscopic examination. For GUS staining, an inserted uidA gene, encoding a β-glucuronidase enzyme expressing in tissue culture cells, was detected by deep blue staining of cells from each of the transgenic lines upon exposure to a colorigenic glucuronidase enzyme substrate, "X-gluc," commercially available from Inalco, according to techniques well known in the art of plant transformation. Microscopic examination demonstrates that cell division has resumed and that transient expression of the uidA transgene displays the normal frequency for these bombardments.

Germinable embryos were produced as follows. After the cell masses that had been cultured on selection medium proliferated to at least one gram, each was separately resuspended in liquid medium again. When the cell suspensions were brought to uniform (half-maximal) SCV, equivalent amounts of suspension culture cells were pipetted onto sterile membrane supports for placement on development/maturation medium as described in U.S. Pat. No. 5,506,136 to develop high quality harvestable stage 3 (cotyledonary) embryos. Dishes were incubated in a dark growth chamber at 23±2° C. The membrane supports were transferred to new petri dishes containing fresh medium every 3 weeks. At week 9, stage 3 (cotyledonary) embryos were visually analyzed for germination quality and harvested onto fabric supports on medium as described in U.S. Pat. No. 5,506,136, and incubated for about four weeks in the dark at a temperature of 4° C.±2° C. Next, embryos on their fabric supports were incubated above water in sealed containers for about three weeks in the dark at a temperature of 25° C.±2° C. Following the above two treatments, embryos on their fabric supports were transferred to medium germination medium and incubated for about three days in the dark at a temperature of 25° C.±2° C. Embryos were then removed from their fabric supports and placed onto the surface of fresh germination medium. Germination was conducted in the light at a temperature of 25° C.±2° C. Germination plates were examined weekly, over a period of about four weeks, and germinating embryos were transferred to MAGENTA® boxes containing 100 ml of germination medium for conversion to plantlets. MAGENTA® boxes containing developing plantlets were incubated in the light at 25° C.±2° C. for about eight to twelve weeks.

When the plantlets formed epicotyls (newly formed shoots of approximately two to four cm), they were transferred to containers filled with a potting mix [2:1:2 peat:perlite:vermiculite, containing 602 g/m³ OSMOCOTE fertilizer (18-6-12), 340 g/m³ dolomitic lime and 78 g/m³ MICRO-MAX micronutrient mixture (Sierra Chemical Co.)]. The plantlets were grown in a shaded greenhouse and misted infrequently for a period of about two weeks. They were removed from mist for acclimatization in the greenhouse for about four weeks. Plantlets were then transferred to outdoor shade for about six weeks for final acclimatization before moving to full-sun conditions. They were then grown in containers until conditions were ready for field planting.

Heights of five month loblolly pine trees transformed with the RNAi vectors as noted above were measured and the results recorded (Table 20). A Duncan Multiple Range test was done on the height data and found that plants transformed with vectors containing the RNAi cassettes of pWVK157, pWVK155, pWVC40, pWVC43 and pWVC44 did not have any significant difference in height compared to GUS control plants (pWVC41), whereas all other transformed lines did have a significant difference in height to the controls. A single untransformed control also was measured to be 21.1 cm tall but statistic analysis was not done with this sample as it was a single result and not an average of multiple samples. Root dry weights also were measured for all the transformed and control trees at 5 months but no significant difference was observed between controls and transgenics.

At seven months of age approximately 200 samples were collected from the above transformed trees or control untransformed trees by cutting approximately 20 mg of tissue from each stem. Each sample was weighed in a quartz boat, and pyrolyzed in a reactor consisting of a quartz tube (2.5 cm inside diameter) with helium flowing through at 5 L/min (at STP). The reactor tube was placed such that the sampling orifice of the molecular-beam mass spectrometer was inside the end of the quartz reactor. A molecular-beam mass spectrometer using a Extrel™ Model TQMS C50 mass spectrometer was used for pyrolysis vapor analysis as described in Evans & Milne (1987) (Energy & Fuels, 1: 123-37). The reactor was electrically heated and its temperature maintained at 550° C. Total pyrolysis time was 90 seconds although the pyrolysis reaction was completed in less than 50 seconds. The residence time of the pyrolysis vapors in the reactor pyrolysis zone has been estimated to be ~75 ms and is short enough that secondary cracking reactions in the quartz reactor are minimal. Mass spectral data from 20-450 Da were acquired on a Teknivent Vector 2™ data acquisition system using 22 eV electron impact ionization. Using this system, both light gases and heavy tars are sampled simultaneously and in real time. The mass spectrum of the pyrolysis vapor provides a rapid, semiquantitative depiction of the molecular fragments.

Duplicate mass spectra of the loblolly pine sample set and standards were collected on two successive days in a block fashion so as to mitigate problems associated with data analysis that could arise from day to day spectrometer drift. A combined analysis of the mass spectra collected on both days indicated that minimal spectrometer drift occurred.

Examination of the spectra determined that mass spectra of the transgenic samples are different from the controls. An example of the pyMBMS spectra of the pyrolysis products from a transgenic and control loblolly pine sample are shown in FIG. 10.

Figure 11A:
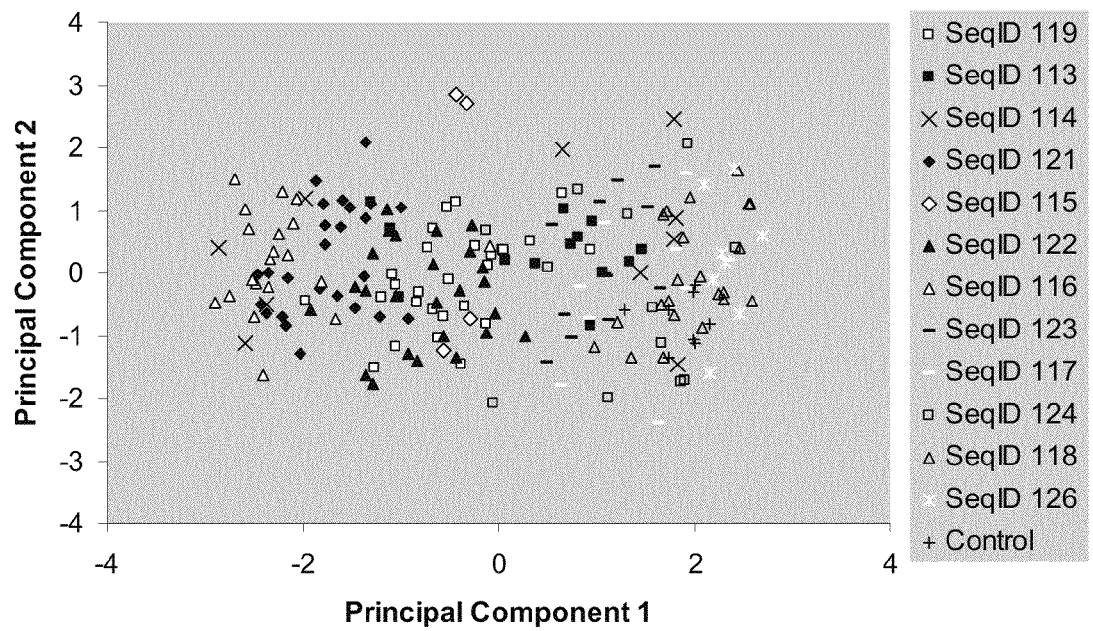
FIG. 11A is a scatter plots of PC1 scores versus PC2 scores of mass spectra collected using a mass range of m/z 50-200 for transgenic loblolly pine samples.
Figure 11B:
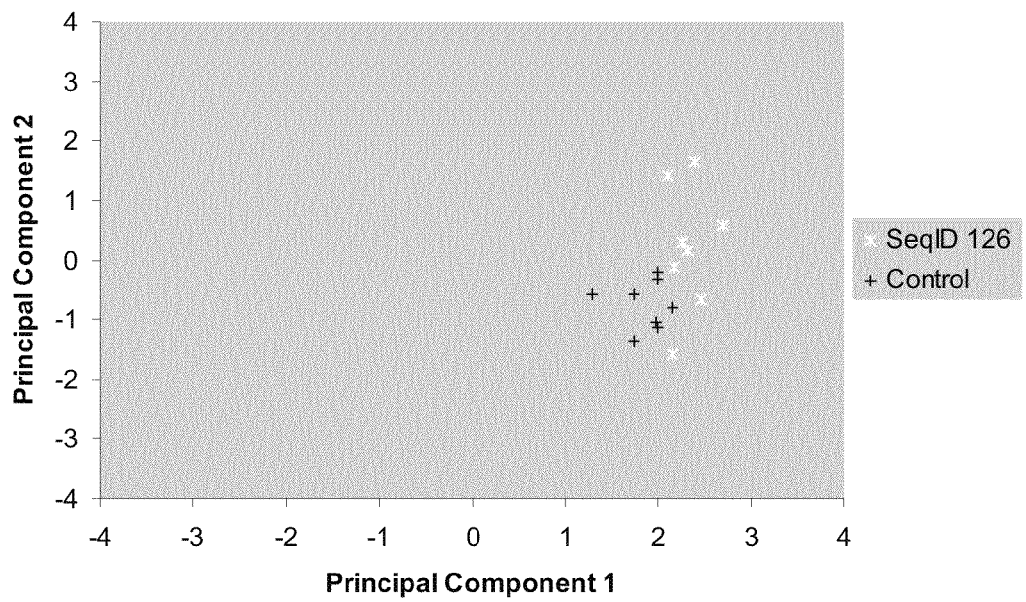
FIG. 11B is a scatter plot highlighting the clustering of constructs pWVC41 and control.
Figure 12A:
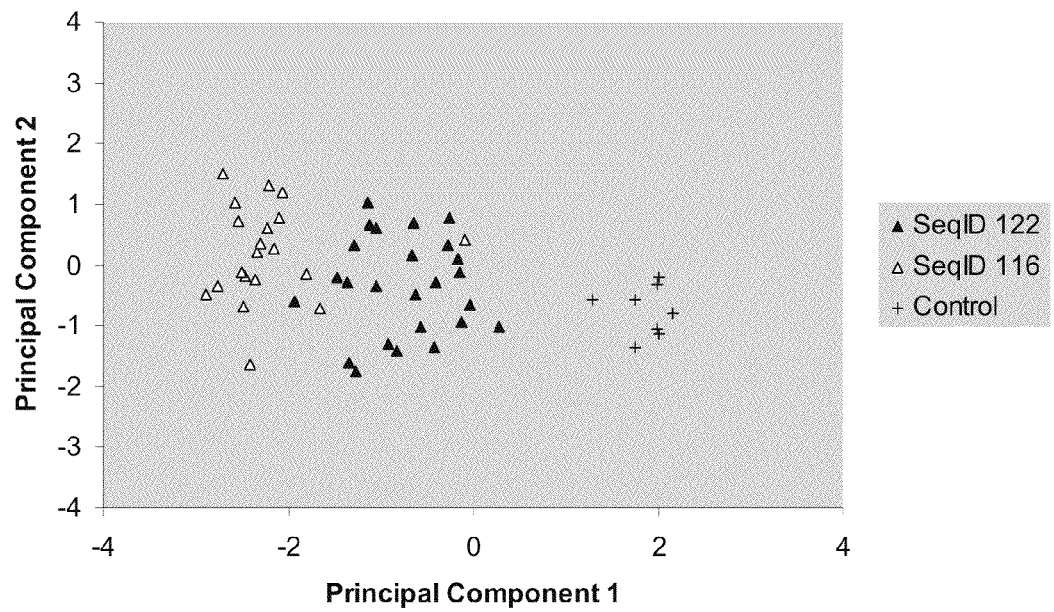
FIG. 12A is a scatter plot highlighting the clustering of constructs pWVK154, pWVC40 and controls.
Figure 12B:
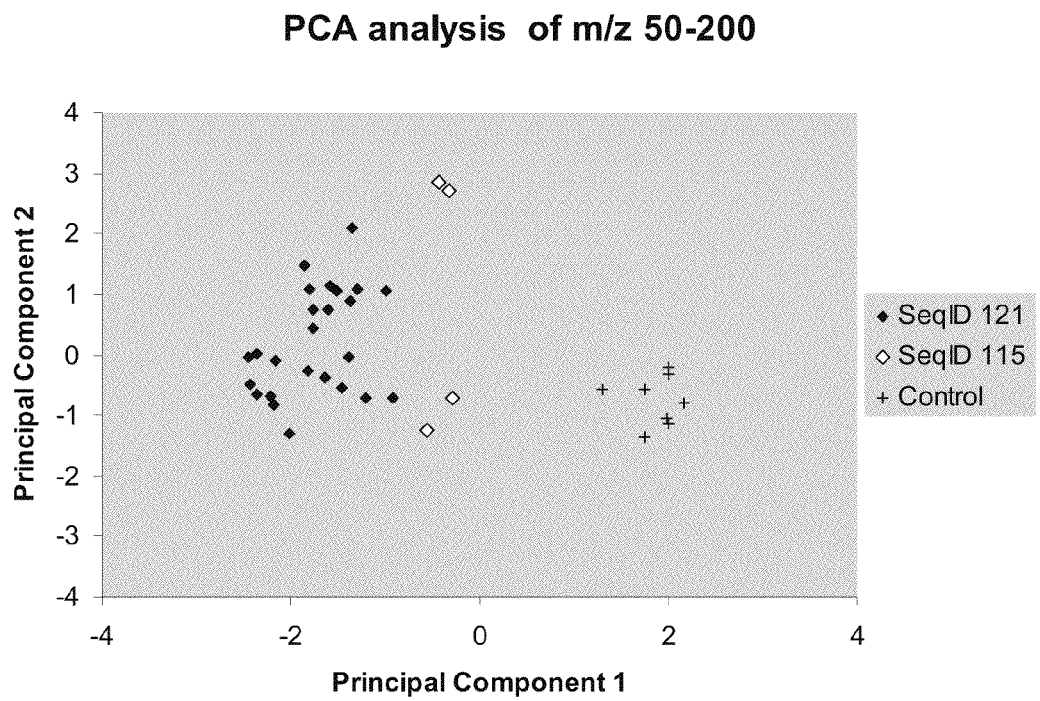
FIG. 12B is a scatter plot highlighting the clustering of constructs pWVK158, pWVC46 and controls.

Principal component analysis of loblolly pine pyMBMS spectra using a mass range between m/z 50 and 200 highlighted pyrolysis products from lignin and carbohydrates while minimizing small pyrolysis and electron impact fragments (below m/z 50) and extractives (above m/z 200). By selecting a mass range that contained more information about lignin and less about the extractives, it became clear that there were significant differences between the constructs. FIG. 11A shows a scatter plot of PC1 scores versus PC2 scores of mass spectra collected using a mass range of m/z 50-200 for all the transgenics analyzed. From this scatter plot we can conclude that plants transformed with some vectors show clear separations to control untransformed plants due to differences in the amount of lignin as determined from the analysis of mass spectra and PC loadings, while others do not. FIGS. 11B, 12A and 12B provide additional insights. Trees transformed with pWVC41 were GUS control transgenics and showed no difference from the control untransformed trees. Trees transformed with pWVC40 and pWVK154 both contained the pine 4CL fragment D coding sequence (SEQ ID NO: 21) and trees transformed with pWVC46 and pWVK158 both contained the pine 4CL fragment C (SEQ ID NO: 20) coding sequence. Each of these transformants separated from the control samples on the scatter plots, indicating a difference in the amount of lignin between the transgenics and controls.

Figure 13:
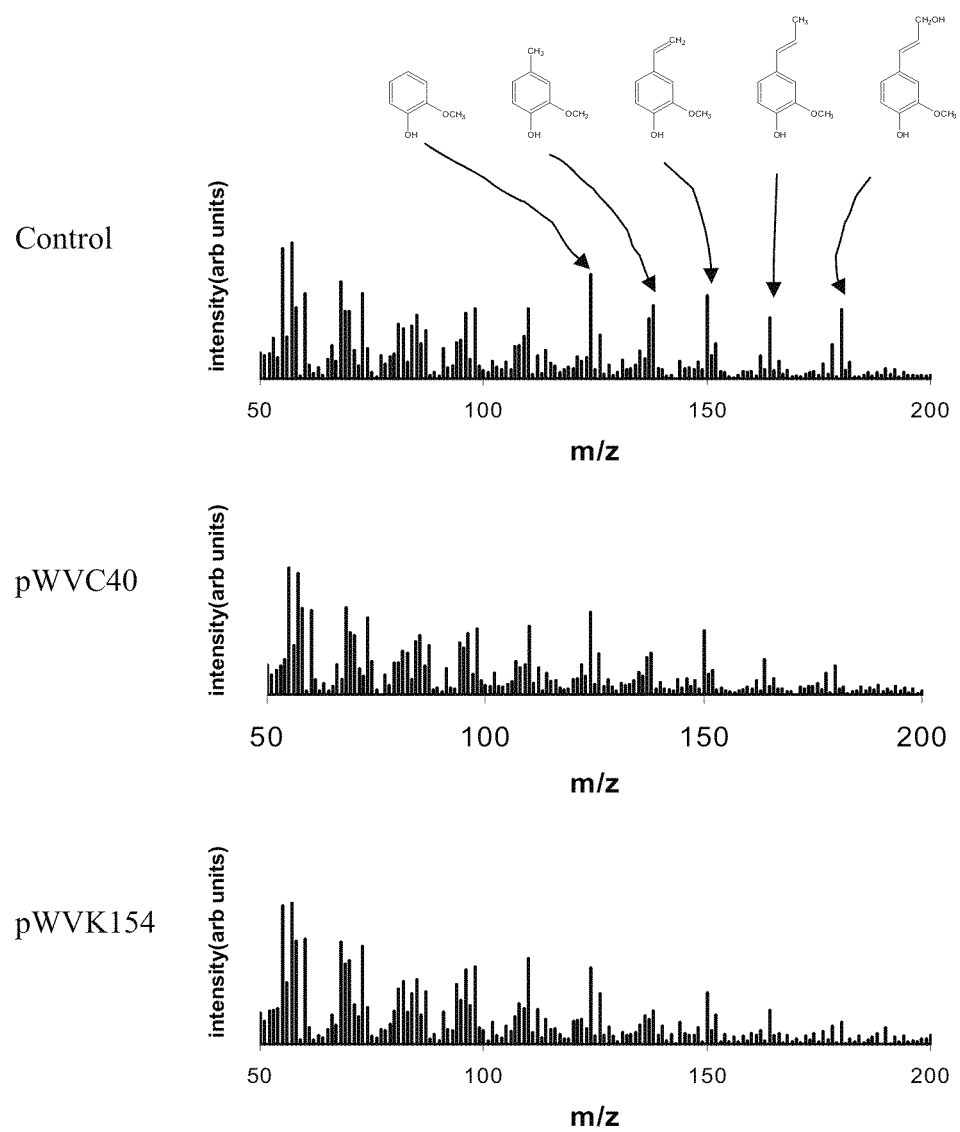
FIG. 13 is a mass spectra of loblolly pine samples from the constructs selected in FIG. 12A. The pyrolysis fragments assigned to the lignin peaks are shown above the control spectrum. The m/z value on the x-axis represents the ratio between the mass of a given ion and the number of elementary charges that it carries.

FIG. 13 shows expanded mass spectrum region of samples selected in FIG. 12A, the control, the transgenics pWVC40 and pWVK154. It is clear that the peaks arising from the pyrolysis of lignin are decreasing with respect to other peaks that can be assigned to carbohydrates and extractives (see Table 21). Similar analysis of the mass spectra of the other constructs indicates that PC1 reflects the concentration of lignin in each sample. Samples to the right in FIGS. 11-12 have the highest lignin content and samples to the left have much lower lignin content.

Seven month old loblolly pine trees transformed with pWVK158, pWVK154, pWVC46 and pWVC40 showed the greatest reduction in lignin content when compared to untransformed controls and GUS transformed controls. Trees transformed with pWVK158, pWVK154 and pWVC42 were significantly shorter than untransformed and GUS transformed trees, where as trees transformed with pWVC40 had a significant lignin reduction but no significant height reduction.

Lignin Evaluation using Nuclear Magnetic Resonance Spectroscopy

High-resolution, solid-state $^{13}C$ NMR spectra were collected at 4.7 T with cross-polarization (CP) and magic angle spinning (MAS) in a Bruker Avance 200 MHz spectrometer. Variable amplitude cross-polarization (1 db linear ramp over cross polarization period) was used to minimize variations of the nonprotonated aromatic carbons that are sensitive to Hartmann-Hahn mismatch at higher MAS rotation rates (S, O Smith, I. Kustanovich, X. Wu, O. B. Peersen, Journal of Magenetic Resonance (1994) 104: 334-339). $^{1}H$ and $^{13}C$ fields were matched at 53.6 kHz and a 1 dB ramp was applied to the proton r.f. during the matching period. Acquisition time was 0.033 seconds and sweepwidth was 31.3 kHz. Magic-angle spinning was performed at a rate of 7000 Hz. 2000-4000 scans were averaged using a 2 ms contact time and a pulse repetition rate of 1.0 sec. Differences observed in relative peak intensities and integrated areas can be used to identify differences between similar samples. Weight % lignin values were calculated from the integrated areas of the aromatic (110 ppm-160 ppm) and carbohydrate (40 ppm-100 ppm) region using the method of Haw et al 1984 (J. F. Haw., G. E. Maciel., H. A. Schroder, Analytical Chemistry 56: 1323).

Figure 14:
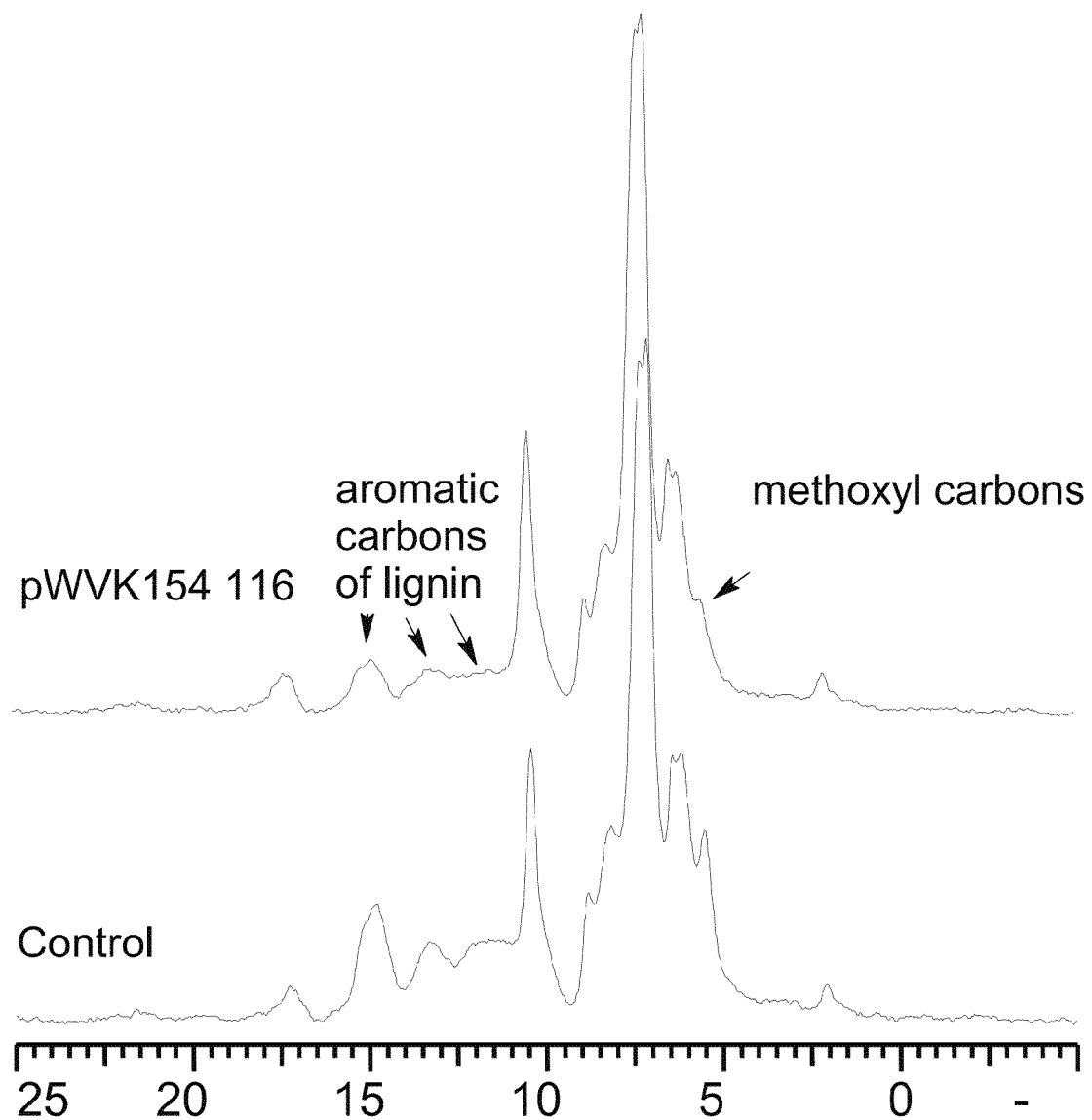
FIG. 14 is a $^{13}C$ CP/MAS spectra of a line of transgenic loblolly pine transformed with pWVK154 and an untransformed control. The spectra demonstrate a decrease in the aromatic and methoxylcarbons relative to the carbohydrate region (~60-110 ppm) in the transgenic line relative to the control line.

Twelve samples were selected based on their PC1 scores and the lignin content was determined using solid-state $^{13}C$ NMR. In some cases, several samples from the same line were combined in order to get a sample that was large enough for the NMR analysis. FIG. 14 shows a comparison of the NMR spectra of a control line (two samples combined) and a transformed line pWVK154 (four samples—combined). The NMR spectra confirmed the results of the pyMBMS analysis that pWVK154 transgenics had a much lower lignin content than the control line. The weight % lignin was determined by integration of the aromatic and carbohydrate regions combined with some assumptions of the lignin and carbohydrate structures (see Haw et al., (1984) *Analytical Chemistry*, 56: 1323). The results for the 12 selected samples are given in Table 22. Comparison of the NMR wt % lignin values with the PC1 scores for the selected samples show that the PC1 scores accurately reflect the amount of lignin in the loblolly pine samples and the PC 1 scores can be used to rank the lignin content of the different constructs.

Lignin Evaluation Using Multivariate Data Analysis

Data analysis was performed using the Unscrambler version 7.8 software program (CAMO A/S, Trondheim, Norway). The Projection to Latent Structure (PLS-1) algorithm, which handles only one Y-variable at a time, was used to construct the model for predicting the lignin contents of the pine samples. The lignin content predictive model was developed using the pyMBMS spectra as the X-matrix (310 variables (m/z values between 50 and 360)) and the lignin values measured by solid-state NMR as the Y-matrix. The mass spectra were normalized to the total ion current before analysis. Model validation was performed using full cross validation which systematically removes one sample from the data, establishes a model with the remaining samples and then uses that model to predict the value of the Y-variable of the samples that was removed from the data set. The process continues until all samples have been removed and predicted from the Y-matrix. The goodness-of-fit (i.e., a high correlation coefficient) and minimal residual error were the criteria used for choosing the best model.

Figure 15:
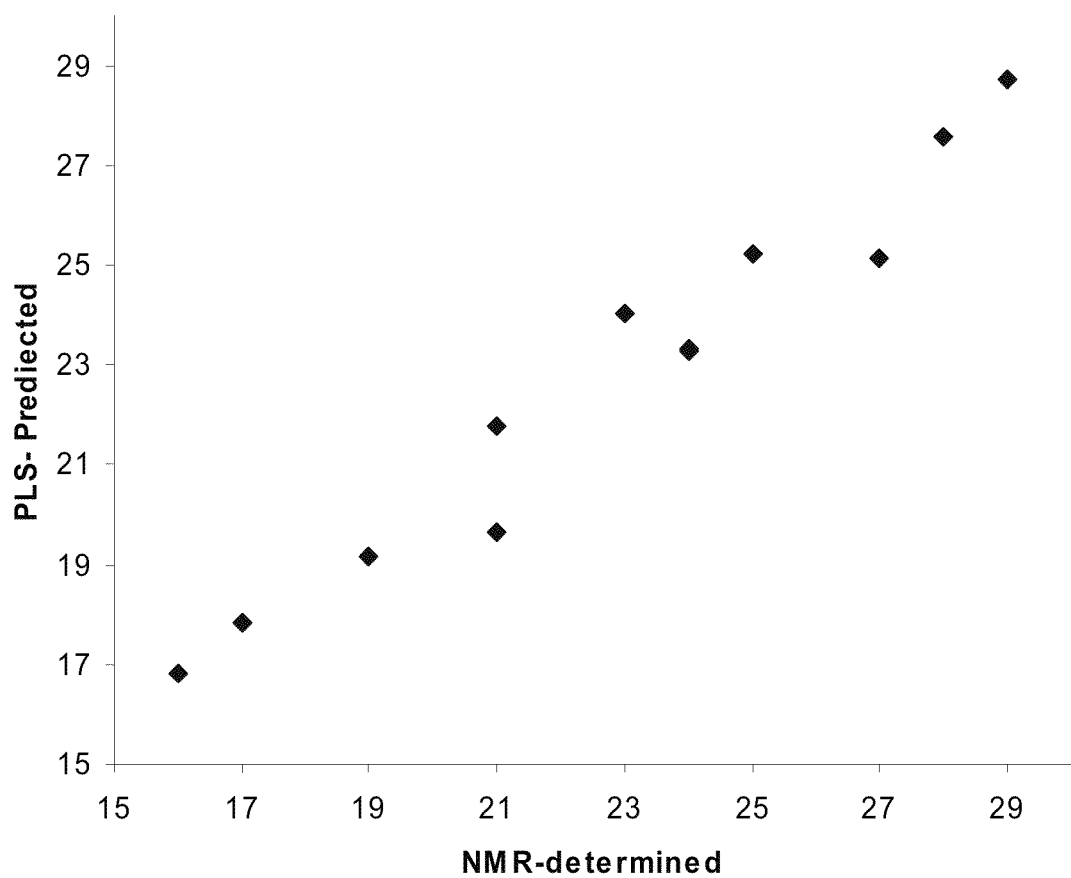
FIG. 15 is a scatter plot of NMR-determined lignin values and PLS-predicted lignin values determined by full cross validation of the PLS model using 2 principal components.

A PLS 1 model to predict lignin content was constructed from the NMR lignin values and the pyMBMS spectra. In cases where more than on tree from the same line was sampled for the NMR analysis, the corresponding mass spectra from the trees were averaged and used to build the model. A PLS model was constructed using a range of m/z values from 50 to 360. This range was determined empirically to provide the best model based on the correlation coefficient of the fully cross-validated model. The final fully cross-validated model shown in FIG. 15, had a RMSEP of 0.9 and an $r^2$ value of 0.94.

The lignin level was determined for each of the transformed lines using an NMR-based model developed by the National Renewable Energy Laboratory (Golden, Colo.). Table 20 shows the percentage of lignin compared to non-transformed controls for each of the RNAi constructs. All of the transformants showed reduced lignin relative to control plants, though different lines possessed different amounts of lignin. Transformants comprising constructs with fragments C or D showed the most lignin reduction.

TABLE 20

Effect of RNAi constructs on lignin level

| RNAi fragment | Percentage of lignin relative to non-transformed controls | | | | | |
|---|---|---|---|---|---|---|
| | A | B | C | D | E | F |
| 4CL promoter | 78.4 | Na | 66.4 | 76.3 | 91.5 | 91.2 |
| SUBQ promoter | 85.5 | 79.2 | 74.2 | 62.5 | 94.0 | 98.6 |

Figure 6:
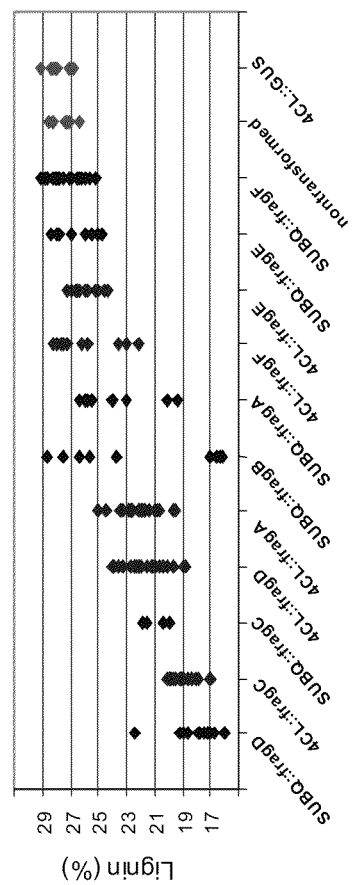
FIG. 6 graphically demonstrates the modulation of lignin levels by 4CL RNAi constructs. Lignin values are the percent of lignin in the cell wall material as measured by NMR.
Figure 7:
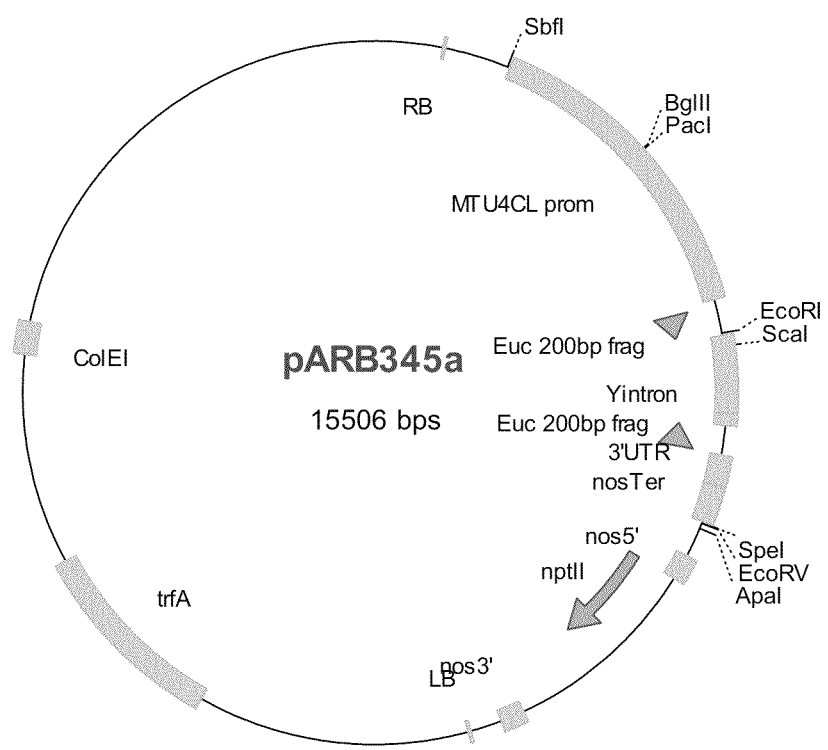
FIG. 7 is plasmid map of the *Eucalyptus* 4CL construct pARB345.
Figure 8:
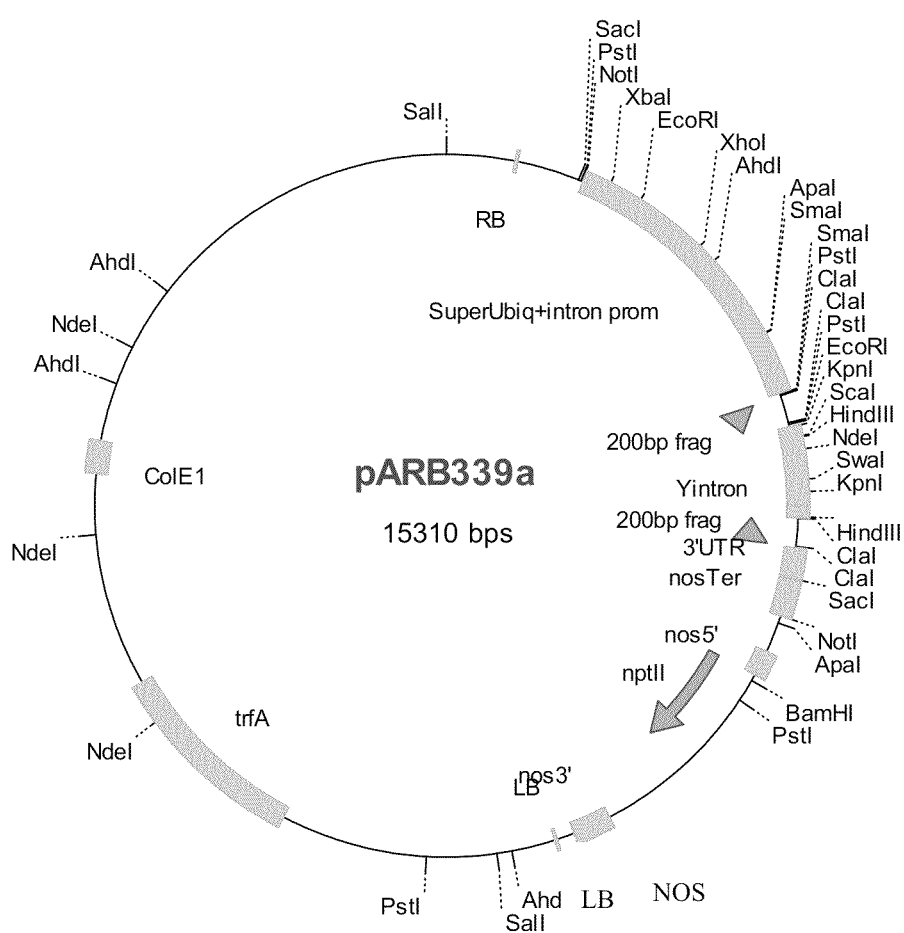
FIG. 8 is plasmid map of the *Eucalyptus* 4CL construct pARB339.
Figure 9:
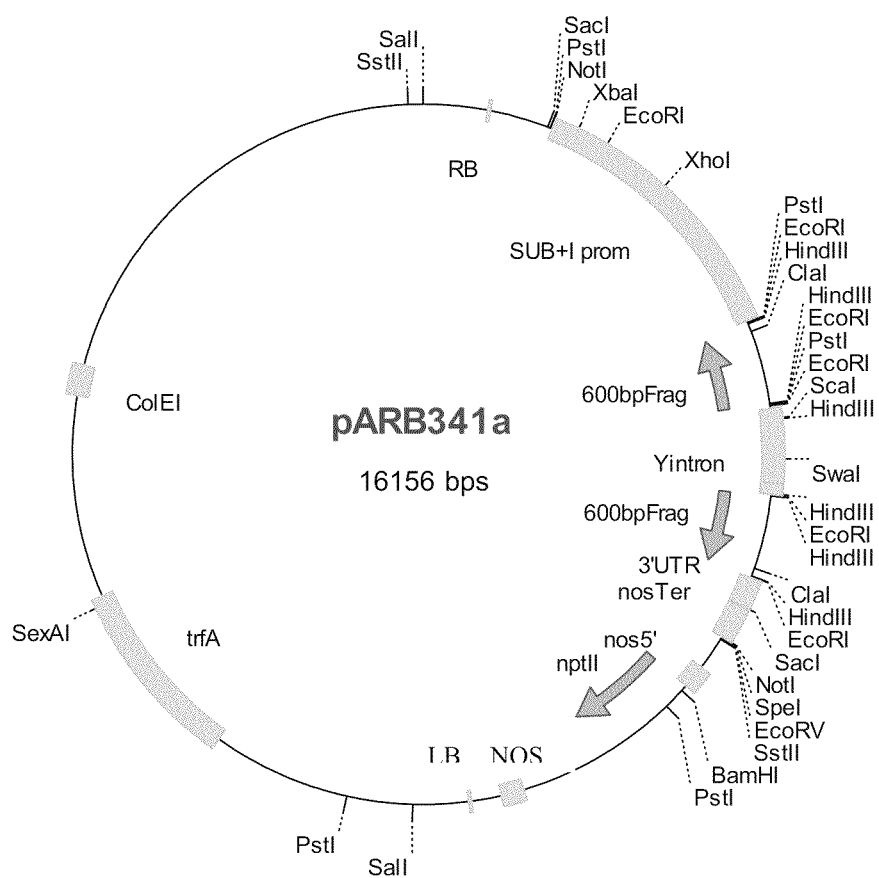
FIG. 9 is plasmid map of the *Eucalyptus* 4CL construct pARB341.

FIG. 6 provides a graph showing the lignin values obtained for each transformant. The constructs are listed in order of average height in the x-axis. Accordingly, the results show that in pine, fragments C and D were associated with an average reduction in growth as well as lignin. Fragment E did not reduce growth, but also did not reduce lignin much. The best lignin reduction that was unaccompanied by an average growth reduction was seen with Fragment A (driven by either promoter) or with Fragment F (driven by 4CL promoter). These constructs constitute the appropriate phenotype for forestry applications.

Table 21 provides mass spectrum peak assignments associated with pyrolysis molecular beam mass spectroscopy of loblolly pine wood samples (Evans et al, *Energy & Fuels*, 1:123-137 (1987)).

TABLE 21

| m/z | Assignment |
|---|---|
| 57, 73, 85, 96, 114, 96 | C5 sugars |
| 57, 60, 73, 98, 126, 144 | C6 sugars |
| 94 | Phenol |
| 110 | catechol, resorcinol |
| 120 | Vinylphenol |
| 122 | Ethylphenol |
| 124 | Guaiacol |
| 137[1] | ethylguaiacol, homovanillin, coniferyl alcohol |
| 138 | Methylguaiacol |
| 150 | Vinylguaiacol |
| 164 | allyl-+propenyl guaiacol |
| 178 | coniferyl aldehyde |
| 180 | coniferyl alcohol, syringylethene |
| 272 | G-G lignin dimer |
| 285[1] | Dehydroabietic acid |
| 300 | Dehydroabietic acid |
| 302 | abietic acid |

[1] fragment ion.

TABLE 22

Weight % lignin values determined by NMR.

| Line transformed with which construct | NMR-determined weight % lignin |
|---|---|
| pWVK154 | 16 |
| pWVC46 | 17 |
| pWVC46 | 19 |
| pWVK143 | 21 |
| pWVC60 | 21 |
| pWVC44 | 23 |
| pWVC60 | 24 |
| pWVC40 | 24 |
| pWVK157 | 25 |
| pWVC43 | 27 |
| pWVC44 | 28 |
| Untransformed Control | 29 |

Example 14

Field Test of Pine Transformants

Four to eight genetically identical propagules (ramets) were rooted from each of 122 lines for field planting, comprising approximately equal numbers of lines for each of the 16 constructs, for a total of approximately 1000 treestocks planted in a randomized block design. Lines transformed with 4CL promoter-driven constructs and superubiquitin promoter-driven constructs were planted in separate blocks of approximately 500 treestocks each with respective controls.

Constructs identified with an asterisk in Table 23 yielded at least some dwarfed transformants. As evident from the table, transformants with superubiquitin promoter-driven constructs were more likely to show dwarfing. Meanwhile, transformants with 4CL promoter-driven constructs were more likely to show reduced lignin without significant dwarfing, as can be seen in Table 23 below, in which Duncan's multiple range test was applied to height measurements. In Table 23, it can be observed that the transformants containing constructs driven by the vascular-preferred promoter are predominantly represented in the larger height class. Accordingly, constructs with tissue-preferred promoters are preferred.

TABLE 23

4CL RNAi-transformed and control trees planted in field test. Ranked by average heights (measured at age 8 months) and root masses (measured at age 12 months, i.e. at time of planting into field sites) of transgenic trees

| Promoter | RNAi fragment of the 4CL gene | Some events showed dwarfing | Height (cm) | Duncan group height | Root mass (g dry wt) | Duncan group roots |
|---|---|---|---|---|---|---|
| 4CL | GUS | | 21.4 | a | 2.31 | ab |
| 4CL | frag E4CL | | 19.1 | ab | 2.29 | ab |
| SUBQ | frag F4CL | | 18.9 | a | 2.47 | a |
| 4CL | frag F4CL | | 17.6 | ab | 2.3 | ab |
| 4CL | frag D4CL | | 17.2 | ab | 2.16 | ab |
| SUBQ | frag E4CL | | 16.5 | ab | 1.91 | b |
| 4CL | frag A4CL | | 15.6 | bc | 2.25 | ab |
| 4CL | frag C4CL | * | 12.5 | cd | 1.93 | ab |
| SUBQ | frag A4CL | * | 12.5 | cd | 2.25 | ab |
| SUBQ | frag C4CL | * | 11.4 | d | 1.85 | b |
| SUBQ | frag D4CL | * | 10 | de | 1.84 | b |
| SUBQ | frag B4CL | * | 7.7 | e | 2.13 | ab |

Duncan's multiple range test was performed on the height and root mass statistics Example 15

Evaluation of Carbohydrate Levels

Secondary xylem (wood) is composed primarily of cellulose (a linear polymer of glucose), hemicelluloses (a linear heteropolysaccharide found in association with cellulose; in gymnosperms the principal component sugar is mannose) and lignin (a phenolic polymer that can not be depolymerized by hydrolysis). The varying levels of carbohydrates (CHOs) and lignin can affect the usefulness of the tree in processes such as pulping. Cellulose is the principal component of pulp yield, and yield may also be affected by the amount and type of hemicellulose associated with the cellulose. Additionally, the cellulose content of wood is positively correlated with strength, important both for pulp-derived and solid wood products.

Harding et. al. (1999) (*Nat. Biotechnol.* 17(8):808-12) found that transgenic aspen trees with reduced lignin levels showed elevated CHO levels. Harding. et. al. claim that the elevation of CHO levels may be responsible for the preservation of plant structural integrity of trees with reduced lignin levels, and that such trees will show enhanced utility for pulping.

Transgenic plant material tested for total lignin amounts can be tested for carbohydrates (CHOs), as a measure of the amount of cellulose and hemicellulose present. Carbohydrate analysis is carried out on extractive free, ground samples. These samples are hydrolyzed in 2 stages with 72% sulphuric acid, firstly by incubations at room temperature for ½ hour, followed by incubation at 120° C. for 1 hour, decanted and analyzed by ion chromatography. From the chromatograms the percent dry wood weight (DWW) of arabinan, galactan, glucan, xylan and mannan are determined.

Hu et al. (1999) (Nature Biotechnology 17: 808-812) demonstrated that transgenic aspen trees downregulating the 4CL gene, exhibited up to a 45% reduction in lignin content and a 15% increase in cellulose content. Assessing carbohydrate levels of transgenic trees tested for lignin in Example 15 will determine whether these constructs show a correlation between decreasing lignin content and increasing cellulose content.

The results from CHO determinations of transgenic trees demonstrate which constructs are correlated with changes to cellulose or hemicellulose content in transformed trees. These results demonstrate that these constructs are enabled to modulate the cellulose content correlated with pulp yield and with strength of pulp fibers and solid wood products.

The constructs alter the cellulose or hemicellulose content in transformed trees. The reduction in lignin levels and increase in CHO levels of transformed trees provide economic and environmental advantages to the pulp industry. In particular, the reduction of lignin content should lead to a reduction of chemicals in pulping and bleaching processes.

Example 16

Additional Methods for Analyzing Lignin Content

In this example, anatomical analysis of older samples of genetic clones of trees examined previously in Example 13 is done in order to compare cell structure and lignin content in transgenic plants between plants of 6 months of age and plants of approximately 18 months of age. Additionally, transgenic plant material tested for total lignin amounts, CHO amounts and micro-pulped in Examples 11 and 13 respectively is examined by confocal microscopy to look at the cell structure present.

Samples are fixed in formalin aceto-alcohol (FAA). Samples are washed in water and sectioned at a thickness of 30-60 mm using a sledge microtome. Sections are stained using safranin staining and examined using a confocal microscope.

A histochemical test for lignin, which detects coniferaldehyde units using phloroglucinol/HCl, also is applied to the samples. Some samples are also examined with toluidine blue stain as an additional stain for lignin. This anatomical analysis identifies the amount of reaction wood present and whether wood (xylem) cells of transgenic plants display any differences with respect to control plants.

These results demonstrate the cell structure of transgenic trees shown to have reduced lignin levels in Examples 12 and 13, but showing normal morphology, have no significant differences to non-transgenic trees with "normal"/higher lignin levels. These results further demonstrate that the cell structure observed in 6 month old trees is consistent with observations in samples from 18 month old trees.

Example 17

Processing of Trees with Reduced Lignin

To determine whether reduced lignin content translates to improvements in the pulping process, the transgenic trees of the examples can be subjected to micro-pulping. Important parameters for determining the suitability of a wood resource for kraft pulping are pulp yield, pulping rate, alkali consumption, fibre qualities and pulp bleachability. Wood samples are air dried, chipped and then oven dried at 105° C. for at least two days and until a constant weight is reached. Kraft pulping is performed in 150 mL stainless steel reactors attached to the rotating arm of a Stalsvets multi-digester pulping unit (Stålsvets, Sweden). The reactors are rotated through a polyethylene bath heated by electric heaters having a total capacity of 12.5 kW and controlled by an Omron controller (Omron Corporation, Illinois, USA) Typical pulping conditions are:

Effective alkali charge: 14% (as $Na_2O$)
Liquor sulphidity: 30%
Liquor:wood ratio: 6:1
Maximum pulping temperature: 170° C.
Time to maximum temperature: 90 minutes
H-factor: Determined by varying the time at 170° C.

Those skilled in the art of pulp manufacture will recognize that many other combinations of micropulping conditions are available to test the pulpability of the wood of the trees of the instant invention. The reactors are quenched in cold water, and the cooked chips filtered off on a Buchner funnel. The filtrate is retained for residual alkali analysis. The cooked chips are washed extensively with tap water and then blended for 15 minutes in a standard British disintegrator. The resulting pulp is filtered on a Buchner funnel and washed with water until the filtrate is clear. The pulp pad is dried overnight at 60° C., and total yield determined by weighing.

Residual alkali is determined by titration with 0.5M hydrochloric acid to the first inflection point (Milanova, E. and Dorris, G. M., *Nordic Pulp and Paper Research Jl.*, 9(1), 4-9 (1994)). Alkali consumption is the difference between the effective alkali charge on chips and residual alkali in the black liquor, expressed as a percentage of oven-dry chips (as $Na_2O$).

Pulp kappa number is determined by a half scale modification of Appita Standard 201m-86 (AS/NZS 1301.201s: 2002). The pulping rate is calculated as the kappa number reached for a given cooking time.

Pulp bleachability is determined by bleaching pulps at 10% consistency using a D-Eo-D sequence (Kibblewhite et al., *Appita*, 51(2), 1145-121 (1998)) as follows: D stage: 0.25 active chlorine multiple, 100% industrial chlorine dioxide, 50° C., 60 minutes. Eo stage: 2% NaOH, 0.25 mPa $O_2$, 70° C., 60 minutes. D stage: 1% $ClO_2$, 70° C., 180 minutes. Following bleaching, 5 g brightness pads are prepared at pH 4-5.5, and brightness is determined after equilibration at 23° C./50% RH using a L & W Elrepho (Lorentzen & Wettre, Kista, Sweden). Fiber qualities such as average fiber length, width, and lumen size and standard deviations are analyzed using a Kaman Fiberglas system (Mets Automation, Kaman, Finland).

The results are correlated to the type of construct used in the transformation and demonstrate that the constructs effectively modulate the suitability of the wood resources for kraft pulping.

Table 24 provides the nucleic acid sequences of the polynucleotides and DNA constructs described herein.

We claim:

1. A DNA construct comprising a promoter operably linked to a first DNA segment comprising at least 50 bp of a *Eucalyptus grandis* cinnamate 4-hydroxylase (C4H) gene sequence disclosed in SEQ ID NO: 47, an intron spacer DNA segment comprising SEQ ID NO: 9, and a second DNA segment comprising a *Eucalyptus grandis* cinnamate 4-hydroxylase (C4H) gene sequence disclosed in SEQ ID NO: 47 that is fully complementary to the first DNA segment, wherein the first and second DNA segments are arranged in a 5' to 3' direction with respect to each other.

2. The DNA construct of claim 1, wherein the promoter is a xylem-preferred promoter.

3. The DNA construct of claim 2, wherein the promoter is a *Eucalyptus grandis* Arabinogalactan Protein promoter.

4. The DNA construct of claim 1, wherein the promoter is a *Pinus taeda* 4CL promoter.

5. A plant cell transformed with the DNA construct of claim 1, wherein the plant cell expresses a double-stranded RNA encoded by the DNA construct.

6. A transgenic plant comprising the plant cell of claim 5, wherein expression of the double-stranded RNA in the plant results in the down-regulation of cinnamate 4-hydroxylase (C4H) gene expression involved in the monolignol biosynthetic pathway in the plant.

7. A method of reducing lignin content in a plant by inhibiting the expression of a cinnamate 4-hydroxylase (C4H) gene involved in the monolignol biosynthetic pathway in the plant, comprising transforming a plant cell with the DNA construct of claim 1, wherein the transformed plant cell expresses a double-stranded RNA encoded by the DNA construct, and culturing the transformed plant cell under conditions that promote regeneration of a transgenic plant, wherein expression of the double-stranded RNA in the plant results in the inhibition of the cinnamate 4-hydroxylase (C4H) gene expression in the plant, thereby reducing lignin content in the transformed plant.

* * * * *

SEQUENCE LISTING

<160> NUMBER OF SEQ ID NOS: 77

<210> SEQ ID NO 1
<211> LENGTH: 42
<212> TYPE: DNA

<213> ORGANISM: Artificial Sequence
<220> FEATURE:
<223> OTHER INFORMATION: Description of Artificial Sequence: Synthetic linker

<400> SEQUENCE: 1
aattcgtcca gcagttgtct ggagctccac cagaaatctg ga                42

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic linker

<400> SEQUENCE: 2
agcttccaga tttctggtgg agcgccagac aactgcttga cg                42

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
agctgagctc gggtgttatt tgtggataat aaattcggg                    39

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gttatggtaa agcaaattat atttctgaga caataggcac tcgagtcga         49

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
aaaatcgatg ggtgttattt gtggataata aattcggg                     38

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ggtaccattt aaatgcggcc gcgatctagt aacatagatg acacc             45

<210> SEQ ID NO 7
<211> LENGTH: 53
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 7
aaatctagag gtaccattta aatgcggccg caaaacccct cacaaataca taa        53

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tttctgcagc ttgaaattga aatatgacta acgaat                            36

<210> SEQ ID NO 9
<211> LENGTH: 402
<212> TYPE: DNA
<213> ORGANISM: Pinus radiata

<400> SEQUENCE: 9
caggtcagta atcttaactt cccttttgaa aactcttaag aatgaaaatt tatcttaaat   60
ttagaaactt tggctgatct ttcgaaaatc tgctaaattt tttggaacct tggccgatct  120
tttaaaaata tgcgaattct tttagcaatc tacaaatctt tttaaaatat ataattgaaa  180
atctgctaaa tttgttggaa ccttgactgt tcttttttaaa atatgcaaat tcttttagca  240
acttgcaaat tctttagcaa tctacaaatc ttttttaaaac atataaatga aaatggacca  300 attttttctag cccctaaatt ttttctagcc ccttgctttt ccttccaaat accctaccta  360
attttgcatc taacaggccc aatcatttaa ccttttcagg gc                    402

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctcgagcagg tcagtaatct taacttccct t                                 31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgaggccc tgaaaaggtt aaatgattgg g                                 31

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
gaattcctgc agaagcttat ccttgggcag ggatacggca tgac 44

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gaattcctgc agaagcttga ttagcaggat ccacctggaa gcctttatat tg 52

<210> SEQ ID NO 14
<211> LENGTH: 3799
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 14

| | |
|---|---|
| ggccgcaaaa cccctcacaa atacataaaa aaaattcttt atttaattat caaactctcc | 60 |
| actacctttc ccaccaaccg ttacaatcct gaatgttgga aaaaactaac tacattgata | 120 |
| taaaaaact acattacttc ctaaatcata tcaaaattgt ataaatatat ccactcaaag | 180 |
| gagtctagaa gatccacttg gacaaattgc ccatagttgg aaagatgttc accaagtcaa | 240 |
| caagatttat caatggaaaa atccatctac caaacttact ttcaagaaaa tccaaggatt | 300 |
| atagagtaaa aaatctatgt attattaagt caaaaagaaa accaaagtga acaaatattg | 360 |
| atgtacaagt ttgagaggat aagacattgg aatcgtctaa ccaggaggcg gaggaattcc | 420 |
| ctagacagtt aaaagtggcc ggaatcccgg taaaaaagat taaaattttt ttgtagaggg | 480 |
| agtgcttgaa tcatgttttt tatgatggaa atagattcag caccatcaaa aacattcagg | 540 |
| acacctaaaa ttttgaagtt taacaaaaat aacttggatc tacaaaaatc cgtatcggat | 600 |
| tttctctaaa tataactaga attttcataa cttccaaagc aactcctccc ctaaccgtaa | 660 |
| aacttttcct acttcaccgt taattacatt ccttaagagt agataaagaa ataaagtaaa | 720 |
| taaaagtatt cacaaaccaa caattttattt cttttattta cttaaaaaaa caaaagttt | 780 |
| atttatttta cttaaatggc ataatgacat atcggagatc cctcgaacga gaatctttta | 840 |
| tctccctggt tttgtattaa aaagtaattt attgtggggt ccacgcggag ttggaatcct | 900 |
| acagacgcgc tttacatacg tctcgagaag cgtgacggat gtgcgaccgg atgaccctgt | 960 |
| ataacccacc gacacagcca gcgcacagta tacacgtgtc atttctctat tggaaaatgt | 1020 |
| cgttgttatc cccgctggta cgcaaccacc gatggtgaca ggtcgtctgt tgtcgtgtcg | 1080 |
| cgtagcggga gaagggtctc atccaacgct attaaatact cgccttcacc gcgttacttc | 1140 |
| tcatctttc tcttgcgttg tataatcagt gcgatattct cagagagctt ttcattcaaa | 1200 |
| ggtatggagt tttgaagggc tttactctta acatttgttt ttctttgtaa attgttaatg | 1260 |
| gtggtttctg tgggggaaga atcttttgcc aggtcctttt gggttcgca tgtttatttg | 1320 |
| ggttattttt ctcgactatg gctgacatta ctagggcttt cgtgctttca tctgtgtttt | 1380 |
| cttcccttaa taggtctgtc tctctggaat atttaatttt cgtatgtaag ttatgagtag | 1440 |
| tcgctgtttg taataggctc ttgtctgtaa aggtttcagc aggtgtttgc gttttattgc | 1500 |
| gtcatgtgtt tcagaaggcc tttgcagatt attgcgttgt actttaatat tttgtctcca | 1560 |

| | |
|---|---|
| accttgttat agtttccctc ctttgatctc acaggaaccc tttcttcttt gagcattttc | 1620 |
| ttgtggcgtt ctgtagtaat attttaattt tgggcccggg ttctgagggt aggtgattat | 1680 |
| tcacagtgat gtgctttccc tataaggtcc tctatgtgta agctgttagg gtttgtgcgt | 1740 |
| tactattgac atgtcacatg tcacatattt tcttcctctt atccttcgaa ctgatggttc | 1800 |
| tttttctaat tcgtggattg ctggtgccat attttatttc tattgcaact gtattttagg | 1860 |
| gtgtctcttt cttttttgatt tcttgttaat atttgtgttc aggttgtaac tatgggttgc | 1920 |
| tagggtgtct gccctcttct tttgtgcttc tttcgcagaa tctgtccgtt ggtctgtatt | 1980 |
| tgggtgatga attatttatt ccttgaagta tctgtctaat tagcttgtga tgatgtgcag | 2040 |
| gtatattcgt tagtcatatt tcaatttcaa gcgatccccc gggctgcaga agcttatcct | 2100 |
| tgggcaggga tacggcatga cagaagcagg cccggtgctg caatgaacc tagccttcgc | 2160 |
| aaagaatcct ttccccgtca atctggctc ctgcggaaca gtcgtccgga acgctcaaat | 2220 |
| aaagatcctc gatacagaaa ctggcgagtc tctcccgcac aatcaagccg gcgaaatctg | 2280 |
| catccgcgga cccgaaataa tgaaggata tattaacgac ccggaatcca cggccgctac | 2340 |
| aatcgatgaa gaaggctggc tccacacagg cgacgtcggg tacattgacg atgacgaaga | 2400 |
| aatcttcata gtcgacagag taaaggagat tatcaatata aaggcttcca ggtggatcct | 2460 |
| gctaatcaag cttctgcagg aattcgtcca gcagtctcga gcaggtcagt aatcttaact | 2520 |
| tccctttga aaactcttaa gaatgaaaat ttatcttaaa tttagaaact ttggctgatc | 2580 |
| tttcgaaaat ctgctaaatt ttttggaacc ttggccgatc ttttaaaaat atgcgaattc | 2640 |
| ttttagcaat ctacaaatct ttttaaaata taattgaa aatctgctaa atttgttgga | 2700 |
| accttgactg ttcttttttaa aatatgcaaa ttcttttagc aacttgcaaa ttctttagca | 2760 |
| atctacaaat cttttttaaaa catataaatg aaaatggacc aattttttcta gccctaaat | 2820 |
| tttttctagc cccttgcttt tccttccaaa taccctacct aattttgcat ctaacaggcc | 2880 |
| caatcattta acctttcag ggctcgagaa tctggaagct tatcggaagc ttgattagca | 2940 |
| ggatccacct ggaagccttt tatattgataa tctcctttac tctgtcgact atgaagattt | 3000 |
| cttcgtcatc gtcaatgtac ccgacgtcgc ctgtgtggag ccagccttct tcatcgattg | 3060 |
| tagcggccgt ggattccggg tcgttaatat atcctttcat tatttcgggt ccgcggatgc | 3120 |
| agatttcgcc ggcttgattg tgcgggagag actcgccagt ttctgtatcg aggatcttta | 3180 |
| tttgagcgtt ccggacgact gttccgcagg agccagattt gacggggaaa ggattctttg | 3240 |
| cgaaggctag gttcattgcc agcaccgggc ctgcttctgt catgccgtat ccctgcccaa | 3300 |
| ggataagctt ccgatgggtg ttatttgtgg ataataaatt cgggtgatgt tcagtgtttg | 3360 |
| tcgtatttct cacgaataaa ttgtgtttat gtatgtgtta gtgttgtttg tctgtttcag | 3420 |
| accctcttat gttatatttt tcttttcgtc ggtcagttga agccaatact ggtgtcctgg | 3480 |
| ccggcactgc aataccattt cgtttaatat aaagactctg ttatccgtga gctcgaattt | 3540 |
| ccccgatcgt tcaaacattt ggcaataaag tttcttaaga ttgaatcctg ttgccggtct | 3600 |
| tgcgatgatt atcatataat ttctgttgaa ttacgttaag catgtaataa ttaacatgta | 3660 |
| atgcatgacg ttatttatga gatgggtttt tatgattaga gtcccgcaat tatacattta | 3720 |
| atacgcgata gaaaacaaaa tatagcgcgc aaactaggat aaattatcgc gcgcggtgtc | 3780 |
| atctatgtta ctagatcgc | 3799 |

<210> SEQ ID NO 15
<211> LENGTH: 785

-continued

```
<212> TYPE: DNA
<213> ORGANISM: Flaveria trinervia

<400> SEQUENCE: 15
ctcgagttgg taaggaaata attattttct tttttccttt tagtataaaa tagttaagtg      60
atgttaatta gtatgattat aataatatag ttgttataat tgtgaaaaaa taatttataa     120
atatattgtt tacataaaca acatagtaat gtaaaaaaat atgacaagtg atgtgtaaga     180
cgaagaagat aaaagttgag agtaagtata ttatttttaa tgaatttgat cgaacatgta     240
agatgatata ctagcattaa tatttgtttt aatcataata gtaattctag ctggtttgat     300
gaattaaata tcaatgataa aatactatag taaaaataag aataaataaa ttaaaataat     360
atttttttat gattaatagt ttattatata attaaatatc tataccatta ctaaatattt     420
tagtttaaaa gttaataaat attttgttag aaattccaat ctgcttgtaa tttatcaata     480
aacaaaatat taaataacaa gctaaagtaa caaataatat caaactaata gaaacagtaa     540
tctaatgtaa caaaacataa tctaatgcta atataacaaa gcgcaagatc tatcattta      600 tatagtatta ttttcaatca acattcttat taatttctaa ataatacttg tagttttatt     660
aacttctaaa tggattgact attaattaaa tgaattagtc gaacatgaat aaacaaggta     720
acatgataga tcatgtcatt gtgttatcat tgatcttaca tttggattga ttacagttgc     780
tcgag                                                                 785

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctcgagttgg taaggaaata attattttct ttttt                                 35

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcgagcaac tgtaatcaat ccaaatgtaa gatc                                  34

<210> SEQ ID NO 18
<211> LENGTH: 334
<212> TYPE: DNA
<213> ORGANISM: Pinus radiata

<400> SEQUENCE: 18
attcaattct tcccactgca ggctacattt gtcagacacg ttttccgcca tttttcgcct      60
gtttctgcgg agaatttgat caggttcgga ttgggattga atcaattgaa aggtttttat     120
tttcagtatt tcgatcgcca tggccaacgg aatcaagaag gtcgagcatc tgtacagatc     180
gaagcttccc gatatcgaga tctccgacca tctgcctctt cattcgtatt gctttgagag     240
agtagcggaa ttcgcagaca gaccctgtct gatcgatggg gcgacagaca gaacttattg     300
cttttcagag gtggaactga tttctcgcaa ggtc                                 334
```

<210> SEQ ID NO 19
<211> LENGTH: 334
<212> TYPE: DNA
<213> ORGANISM: Pinus radiata

<400> SEQUENCE: 19

```
gctgccggtc tggcgaagct cgggttgcag caggggcagg ttgtcatgct tctccttccg      60
aattgcatcg aatttgcgtt tgtgttcatg ggggcctctg tccggggcgc cattgtgacc     120
acggccaatc ctttctacaa gccgggcgag atcgccaaac aggccaaggc cgcgggcgcg     180
cgcatcatag ttaccctggc agcttatgtt gagaaactgg ccgatctgca gagccacgat     240
gtgctcgtca tcacaatcga tgatgctccc aaggaaggtt gccaacatat ttccgttctg     300
accgaagccg acgaaaccca atgcccggcc gtga                                 334
```

<210> SEQ ID NO 20
<211> LENGTH: 334
<212> TYPE: DNA
<213> ORGANISM: Pinus radiata

<400> SEQUENCE: 20

```
caatccaccc ggacgatgtc gtggcgttgc cctattcttc cggaaccacg gggctcccca      60
agggcgtgat gttaacgcac aaaggcctgg tgtccagcgt tgcccagcag gtcgatggtg     120
aaaatcccaa tctgtatttc cattccgatg acgtgatact ctgtgtcttg cctctttcc     180
acatctattc tctcaattcg gttctcctct gcgcgctcag agccggggct gcgaccctga     240
ttatgcagaa attcaacctc acgacctgtc tggagctgat tcagaaatac aaggttaccg     300
ttgccccaat tgtgcctcca attgtcctgg acat                                 334
```

<210> SEQ ID NO 21
<211> LENGTH: 334
<212> TYPE: DNA
<213> ORGANISM: Pinus radiata

<400> SEQUENCE: 21

```
cacaaagagc cccatcgttt cccagtacga tgtctcgtcc gtccggataa tcatgtccgg      60
cgctgcgcct ctcgggaagg aactcgaaga tgccctcaga gagcgttttc ccaaggccat     120
tttcgggcag ggctacggca tgacagaagc aggcccggtg ctggcaatga acctagcctt     180
cgcaaagaat cctttccccg tcaaatctgg ctcctgcgga acagtcgtcc ggaacgctca     240
aataaagatc ctcgatacag aaactggcga gtctctcccg cacaatcaag ccggcgaaat     300
ctgcatccgc ggacccgaaa taatgaaagg atat                                 334
```

<210> SEQ ID NO 22
<211> LENGTH: 334
<212> TYPE: DNA
<213> ORGANISM: Pinus radiata

<400> SEQUENCE: 22

```
attaacgacc cggaatccac ggccgctaca atcgatgaag aaggctggct ccacacaggc      60
gacgtcgggt acattgacga tgacgaagaa atcttcatag tcgacagagt aaaggagatt     120
atcaaatata agggcttcca ggtggctcct gctgagctgg aagctttact tgttgctcat     180
ccgtcaatcg ctgacgcagc agtcgttcct caaaagcacg aggaggcggg cgaggttccg     240
gtggcgttcg tggtgaagtc gtcggaaatc agcgagcagg aaatcaagga attcgtggca     300
aagcaggtga ttttctacaa gaaaatacac agag                                 334
```

<210> SEQ ID NO 23
<211> LENGTH: 327
<212> TYPE: DNA
<213> ORGANISM: Pinus radiata

<400> SEQUENCE: 23
tttactttgt ggatgcgatt cctaagtcgc cgtccggcaa gattctgaga aaggatttga       60
gaagcagact ggcagcaaaa tgaaaatgaa tttccatatg attctaagat tcctttgccg      120
ataattatag gattcctttc tgttcacttc tatttatata ataaagtggt gcagagtaag      180
cgccctataa ggagagagag agcttatcaa ttgtatcata tggattgtca acgccctaca      240
ctcttgcgat cgcttttcaat atgcatatta ctataaacga tatatgtttt ttttataaat      300
ttactgcact tctcgttcaa aaaaaaa                                          327

<210> SEQ ID NO 24
<211> LENGTH: 315
<212> TYPE: DNA
<213> ORGANISM: Pinus radiata

<400> SEQUENCE: 24
ccttcgcaaa gaatcctttc cccgtcaaat ctggctcctg cggaacagtc gtccggaacg       60
ctcaaataaa gatcctcgat acagaaactg gcgagtctct cccgcacaat caagccggcg      120
aaatctgcat ccgcggaccc gaaataatga aggatatat taacgacccg gaatccacgg       180
ccgctacaat cgatgaagaa ggctggctcc acacaggcga cgtcgggtac attgacgatg      240
acgaagaaat cttcatagtc gacagagtaa aggagattat caaatataag ggcttccagg      300
tggctcctgc tgagc                                                       315

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aatcgatact gcaggcgcca ccaccaaacg ctca                                   34

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aatcgatact gcagactcgg agatgttctc gaag                                   34

<210> SEQ ID NO 27
<211> LENGTH: 200
<212> TYPE: DNA
<213> ORGANISM: Eucalyptus grandis

<400> SEQUENCE: 27
gcgccaccac caaacgctca ccttctcatc atcagccctc tgtctctgtc tctgtctctc       60
gattctccgc ccgccacga caatggaggc gaagccgtcg gagcagcccc gcgagttcat      120

```
cttccggtcg aagctccccg acatctacat tcccgacaac ctctccctcc acgcctactg    180
cttcgagaac atctccgagt                                                200

<210> SEQ ID NO 28
<211> LENGTH: 223
<212> TYPE: DNA
<213> ORGANISM: Eucalyptus grandis

<400> SEQUENCE: 28
tcgccgaccg cccctgcgtc atcaacgggg ccaccggccg gacctacacc tatgccgagg    60
tcgagctgat ctcccgccgg gtctcagccg gcctcaacgg gctcggcgtc ggacagggcg   120
acgtgatcat gctgctcctc cagaactgcc ctgagttcgt gttcgcgttc ctcggcgcgt   180
cctaccgggg cgccatcagc acgaccgcga acccgttcta cac                     223

<210> SEQ ID NO 29
<211> LENGTH: 300
<212> TYPE: DNA
<213> ORGANISM: Eucalyptus grandis

<400> SEQUENCE: 29
gcgccggagg gctgcctgca cttctcggaa ttgatgcagg cggacgagaa cgccgccccc    60
gcggcggacg tcaagccgga cgacgtcttg gcgctcccct attcgtcggg cacgacgggg   120
cttcccaagg gagtgatgct tacgcacagg ggtcaagtga ccagcgtggc gcagcaggtc   180
gacggagaca accccaactt gtacttccac aaggaggacg tgatcctgtg cacgctcccg   240
ttgttccaca tatactccct caactcggtg atgttctgcg cgctccgtgt cggcgccgcc   300

<210> SEQ ID NO 30
<211> LENGTH: 348
<212> TYPE: DNA
<213> ORGANISM: Eucalyptus grandis

<400> SEQUENCE: 30
gagctcgagg acaccgtgcg agccaagctg cccaatgcca agctcggaca gggctatggg    60
atgacggagc cgggcccggt gctggcaatg tgcccggcat ttgcaaagga gccgttcgag   120
atcaagtcag gcgcatgcgg gaccgtcgtg aggaacgcgg agatgaagat cgtcgacccg   180
gagacagggg cctcgctccc gcggaaccag gccggcgaga tctgcatccg gggtcaccag   240
atcatgaaag gttatctgaa cgacgccgag gcgaccgcaa ataccataga caaagaaggg   300
tggctgcaca ccggcgacat cggctacata gacgatgacg acgagctc                348

<210> SEQ ID NO 31
<211> LENGTH: 500
<212> TYPE: DNA
<213> ORGANISM: Eucalyptus grandis

<400> SEQUENCE: 31
ttcctgttgc attcgtggtg aaatccaatg gttccgtaat caccgaggac gaaatcaagc    60
aatacatctc gaagcaggtc gtgttttaca agaggatcaa gcgggttttc ttcacggacg   120
caattccgaa agcccctcc ggaaaaatct tgaggaagga cctaagagca agttggcct    180 ctggtgttta caattaattt ctcatacct tttcttttc aaccctgccc ctgtacttgc    240
ttaaagaccc atgtagttga atgaatgta acctcttcgg aggggccaaa tatggaaggg   300
ggaaagaaag acatatggcg atgatttgat ttcacatgct attgtaatgt atttattgtt   360
tcaattccga attagacaaa gtgcttaaag ctctctttc ggattttttt tttcattaat    420
```

| | | |
|---|---|---|
| gtataataat tgcggacatt acaatatact gtacaacgtg atttgagctt gatgaattac | 480 | |
| aagattggaa gaacttcgaa | 500 | |

<210> SEQ ID NO 32
<211> LENGTH: 3844
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 32

| | |
|---|---|
| ggccgcaaaa cccctcacaa atacataaaa aaaattcttt atttaattat caaactctcc | 60 |
| actacctttc ccaccaaccg ttacaatcct gaatgttgga aaaaactaac tacattgata | 120 |
| taaaaaact acattacttc ctaaatcata tcaaaattgt ataaatatat ccactcaaag | 180 |
| gagtctagaa gatccacttg gacaaattgc ccatagttgg aaagatgttc accaagtcaa | 240 |
| caagatttat caatggaaaa atccatctac caaacttact ttcaagaaaa tccaaggatt | 300 |
| atagagtaaa aaatctatgt attattaagt caaaaagaaa accaaagtga acaaatattg | 360 |
| atgtacaagt ttgagaggat aagacattgg aatcgtctaa ccaggaggcg gaggaattcc | 420 |
| ctagacagtt aaaagtggcc ggaatcccgg taaaaagat taaaattttt ttgtagaggg | 480 |
| agtgcttgaa tcatgttttt tatgatggaa atagattcag caccatcaaa aacattcagg | 540 |
| acacctaaaa ttttgaagtt taacaaaaat aacttggatc tacaaaaatc cgtatcggat | 600 |
| tttctctaaa tataactaga attttcataa ctttcaaagc aactcctccc ctaaccgtaa | 660 |
| aacttttcct acttcaccgt taattacatt ccttaagagt agataaagaa ataaagtaaa | 720 |
| taaaagtatt cacaaaccaa caatttatt cttttattta cttaaaaaaa caaaaagttt | 780 |
| atttatttta cttaaatggc ataatgacat atcggagatc cctcgaacga gaatctttta | 840 |
| tctcccctggt tttgtattaa aaagtaattt attgtgggggt ccacgcggag ttggaatcct | 900 |
| acagacgcgc tttacatacg tctcgagaag cgtgacggat gtgcgaccgg atgaccctgt | 960 |
| ataacccacc gacacagcca gcgcacagta tacacgtgtc atttctctat tggaaaatgt | 1020 |
| cgttgttatc cccgctggta cgcaaccacc gatggtgaca ggtcgtctgt tgtcgtgtcg | 1080 |
| cgtagcggga gaagggtctc atccaacgct attaaatact cgccttcacc gcgttacttc | 1140 |
| tcatcttttc tcttgcgttg tataatcagt gcgatattct cagagagctt ttcattcaaa | 1200 |
| ggtatggagt tttgaagggc tttactctta acatttgttt ttcttttgtaa attgttaatg | 1260 |
| gtggttctg tgggggaaga atcttttgcc aggtcctttt gggtttcgca tgtttatttg | 1320 |
| ggttattttt ctcgactatg gctgacatta ctagggcttt cgtgctttca tctgtgtttt | 1380 |
| cttcccttaa taggtctgtc tctctggaat atttaatttt cgtatgtaag ttatgagtag | 1440 |
| tcgctgtttg taataggctc ttgtctgtaa aggtttcagc aggtgttttgc gttttattgc | 1500 |
| gtcatgtgtt tcagaaggcc tttgcagatt attgcgttgt actttaatat tttgtctcca | 1560 |
| accttgttat agtttccctc ctttgatctc acaggaaccc tttcttcttt gagcattttc | 1620 |
| ttgtggcgtt ctgtagtaat attttaattt tgggcccggg ttctgagggt aggtgattat | 1680 |
| tcacagtgat gtgctttccc tataaggtcc tctatgtgta agctgttagg gtttgtgcgt | 1740 |
| tactattgac atgtcacatg tcacatattt tcttcctctt atccttcgaa ctgatggttc | 1800 |
| tttttctaat tcgtggattg ctggtgccat attttatttc tattgcaact gtattttagg | 1860 |
| gtgtctcttt ctttttgatt tcttgttaat atttgtgttc aggttgtaac tatgggttgc | 1920 |

-continued

```
tagggtgtct gccctcttct tttgtgcttc tttcgcagaa tctgtccgtt ggtctgtatt    1980
tgggtgatga attatttatt ccttgaagta tctgtctaat tagcttgtga tgatgtgcag    2040
gtatattcgt tagtcatatt tcaatttcaa gcgatccccc gggctgcagg cgccaccacc    2100
aaacgctcac cttctcatca tcagccctct gtctctgtct ctgtctctcg attctccgcc    2160
ccgccacgac aatggaggcg aagccgtcgg agcagccccg cgagttcatc ttccggtcga    2220
agctccccga catctacatt cccgacaacc tctccctcca cgcctactgc ttcgagaaca    2280
tctccgagtc tgcaggaatt cgtccagcag taattcgatt ctcgagttgg taaggaaata    2340
attattttct tttttccttt tagtataaaa tagttaagtg atgttaatta gtatgattat    2400
aataatatag ttgttataat tgtgaaaaaa taatttataa atatattgtt tacataaaca    2460
acatagtaat gtaaaaaaat atgacaagtg atgtgtaaga cgaagaagat aaagttgag    2520 agtaagtata ttattttttaa tgaatttgat cgaacatgta agatgatata ctagcattaa    2580
tatttgtttt aatcataata gtaattctag ctggtttgat gaattaaata tcaatgataa    2640
aatactatag taaaaataag aataaataaa ttaaaataat atttttttat gattaatagt    2700
ttattatata attaaatatc tataccatta ctaaatattt tagtttaaaa gttaataaat    2760
attttgttag aaattccaat ctgcttgtaa tttatcaata aacaaaatat taaataacaa    2820
gctaaagtaa caataatat caaactaata gaaacagtaa tctaatgtaa caaaacataa    2880
tctaatgcta atataacaaa gcgcaagatc tatcatttta tatagtatta ttttcaatca    2940
acattcttat taatttctaa ataatacttg tagttttatt aacttctaaa tggattgact    3000
attaattaaa tgaattagtc gaacatgaat aaacaaggta acatgataga tcatgtcatt    3060
gtgttatcat tgatcttaca tttggattga ttacagttgc tcgagaatca ctagtgaatt    3120
aaatctggaa gcttatcgat actgcagact cggagatgtt ctcgaagcag taggcgtgga    3180
gggagaggtt gtcgggaatg tagatgtcgg ggagcttcga ccggaagatg aactcgcggg    3240
gctgctccga cggcttcgcc tccattgtcg tggcggggcg gagaatcgag agacagagac    3300
agagacagag ggctgatgat gagaaggtga gcgtttggtg gtggcgcctg cagtatcgat    3360
gggtgttatt tgtggataat aaattcgggt gatgttcagt gtttgtcgta tttctcacga    3420
ataaattgtg tttatgtatg tgttagtgtt gtttgtctgt ttcagacccct cttatgttat    3480 atttttcttt tcgtcggtca gttgaagcca atactggtgt cctggccggc actgcaaatac    3540 catttcgttt aatataaaga ctctgttatc cgtgagctcg aatttccccg atcgttcaaa    3600
catttggcaa taaagtttct taagattgaa tcctgttgcc ggtcttgcga tgattatcat    3660
ataatttctg ttgaattacg ttaagcatgt aataattaac atgtaatgca tgacgttatt    3720
tatgagatgg gttttatga ttagagtccc gcaattatac atttaatacg cgatagaaaa    3780
caaaatatag cgcgcaaact aggataaatt atcgcgcgcg gtgtcatcta tgttactaga    3840
tcgc                                                                3844
```

<210> SEQ ID NO 33
<211> LENGTH: 200
<212> TYPE: DNA
<213> ORGANISM: Eucalyptus grandis

<400> SEQUENCE: 33

```
atttgatttc acatgctatt gtaatgtatt tattgtttca attccgaatt agacaaagtg     60
cttaaagctc tcttttcgga ttttttttttt cattaatgta taataattgc ggacattaca    120
```

| atatactgta caacgtgatt tgagcttgat gaattacaag attggaagaa cttcgaagac | 180 |
| aaaaaaaaaa aaaaaaaaaa | 200 |

<210> SEQ ID NO 34
<211> LENGTH: 600
<212> TYPE: DNA
<213> ORGANISM: Eucalyptus grandis

<400> SEQUENCE: 34

| gcgccaccac caaacgctca ccttctcatc atcagccctc tgtctctgtc tctgtctctc | 60 |
| gattctccgc cccgccacga caatggaggc gaagccgtcg gagcagcccc gcgagttcat | 120 |
| cttccggtcg aagctccccg acatctacat tcccgacaac ctctcccctcc acgcctactg | 180 |
| cttcgagaac atctccgagt tcgccgaccg cccctgcgtc atcaacgggg ccaccggccg | 240 |
| gacctacacc tatgccgagg tcgagctgat ctcccgccgg gtctcagccg gcctcaacgg | 300 |
| gctcggcgtc ggacagggcg acgtgatcat gctgctcctc cagaactgcc ctgagttcgt | 360 |
| gttcgcgttc ctcggcgcgt cctaccgggg cgccatcagc acgaccgcga accgttcta | 420 |
| caccccgggc gagatcgcca agcaggcctc agctgcccgg ccaagatcg tgatcacgca | 480 |
| ggccgcgttc gccgacaagg tgaggccgtt cgcggaggaa acggggtga aggtcgtgtg | 540 |
| catcgatacc gcgccggagg gctgcctgca cttctcggaa ttgatgcagg cggacgagaa | 600 |

<210> SEQ ID NO 35
<211> LENGTH: 2435
<212> TYPE: DNA
<213> ORGANISM: Eucalyptus grandis

<400> SEQUENCE: 35

| aaatacatgc cagtgtggaa taactatgcg aagttatcat ttggtgcact tgcttgggtg | 60 |
| aacttgatgc cttactgaag ttttattttt gaccatcttt gttgtgattt aacatatttg | 120 |
| agcgctaccg tacttatgac acttaaatga tgaaagttgc tgtagggtga atttggctgt | 180 |
| ttgacgcatg gagattaggc attaaccttt cttagttatg ctgattattt cttgtgtgtc | 240 |
| ttttttttccc cctccttcag catcacttgt ttgcaagtgg aagagatatg actttctttc | 300 |
| aggtacttgt tttcataccc atattaatac atctggttaa atcatgaaat ttttgtattg | 360 |
| atcgtttgta tgtccaatga cagtatgacc tattcaatga catttggttg tgtgctagat | 420 |
| ttcgttccag agaaaatgaa agcagaagat gcattggcag agaggaaacc agaagagaca | 480 |
| tgaatatgat actaatctta ggtcaagaag ctgtaacttt cattgattga ggggcttcaa | 540 |
| tttgtatgag catcttatac tgtgatttgg ttctttttcct gctatagcag aatagagcca | 600 |
| gcaaaatggg cacttacatt tagctgcaga tgatgtctgt atgggcgaat tttttcgcat | 660 |
| gttacattgg agaagagaaa tgcttatact tctggtaatt ttttcagcaa atagtctcat | 720 |
| gccctgctaa catggatggt gggatagctt cttctgggga gtgtaattaa tctgtcatgg | 780 |
| acaagtactt tgtagttaat ctgattctcg gcctatgtta tatctgtttt gcgttatact | 840 |
| aaagatattc agatcaatct atgtcaatct attcacgaaa acccggggag tctaatgagg | 900 |
| agagttgcat cttggcaata tagttttttaa gaatggatat ccagatccct acgaactgga | 960 |
| ttcacacagt cactgctgta agctctggtt tttttttagct taggaagcag gttataatca | 1020 |
| aagatgatta aaccatcgcg tgttcgccag ccatcagaaa tggaaaggca aatgttgtta | 1080 |
| tagtgatgga cagatcatgc tgagatgatt gattatgaat cttactgatg actgtcattt | 1140 |
| atgttatcgc actctgtgtg tgtgggtgtg tgtaatgagt aatatcaaat taaccagacg | 1200 |

```
ataggtgttg aagattagct gttgggccgc cgtggcaaaa ggtgtcttat acaagccatc    1260
ggcagtgacg cagaactgta gagaaccgct gtaacaagtc ttcgaatgca ttcttttaat    1320
gtacagcacg acatgaaggg ggttcaagtg tagcgaacag ttcgtgcgag aaagatcatt    1380
ttcaatagca taaaagagtc tgctctctgc tgcaaacatg gaaagaactt acatttcaat    1440
cattgaggag aagattataa caaatcctaa atggttggga ttttagttag tccattcgaa    1500
ctaaagtggc gaagatgtca gttttttcaag tggatgatat ttctcatgta tgttccgcag    1560
aggcaatcac cttgtttgta actagacatc tagagaacct aacaaggatt gatggggtg     1620 aggtgaaatg tctgtttcct ctttaatatg gatccagcga tgccttacag agcggatgga    1680
tggcactggc aagtcttaat ccttaggtcg aatgtttgat tggtaacaga tgccttttct    1740
ttcttttcaa tcacagctga caaatgcaaa tatctaaaac cattggctgt ttggtgcttg    1800
caagtctgga ttaccccact ttatgtttca cctttcaata atgaataaca aggtactcgg    1860
gaaaaaaagg aaagggaaat tcgcacaacc aaagttgcta tgcagaagtc aactcaatcc    1920
taatcaagtt gatgagagtg ttgggcccta ttttctgcag caaacatgaa tctcgattca    1980
tctccctcgc aaaagataag gaagctgcaa aagcttcct cctaagtttg ttggcaggca    2040
aattgatttt gtaccagaaa taaatacaaa gtgaaaccca agcaatcacg catggcctga    2100
tttgtgccat gtccattga tctccctcta ccatttttcc tgctttctca agcaaactag     2160
ttgctgtaac agtgaatgat cccccggctc tctctctctc tctctctctc tccatttatt    2220
ccatccatgt ttttgctttt cgcacaacac ttatcattga ggtgctaact actgaattcc    2280
cctaactaaa aattggaacc tctcacctaa tttcatttc tcccactttg atgagcacca     2340
ctctctttcc cagatttcaa ataaattgcc actctctccc tcctctttcc tcacacaacc    2400
aaaagccttc ttcaagtacc acttcttcac tgtcc                               2435
```

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gagagaggat ccggtgtgaa ataccgcaca g                                    31

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gagagatgat cagcctcact gattaagcat tggtaactg                            39

<210> SEQ ID NO 38
<211> LENGTH: 390
<212> TYPE: DNA
<213> ORGANISM: Pinus radiata

<400> SEQUENCE: 38
gtagatttaa atgcttttt gaaatccggt tactcgcaag attatcaatc gggactgtag      60

```
ccgaagcttt gagaggttga aattcagact tttgctccga actgttctgc tgaaacaaaa    120
tccagtattg agctaggttt agaatcgggt ttgctggtca tctgggagag gcgatccatt    180
cagcttcgca ggcccccgaa gatggcgttc gccggcacaa cccagaagtg caaggcatgt    240
gaaaagacgg tctatttggt tgatcaattg acagctgata attctgtttt tcacaaatcc    300
tgtttccgct gccatcactg caatggaact ttaaagctta gcaactattc gtcgtttgag    360
ggagttctat attgcaaacc tcattttgac                                      390
```

<210> SEQ ID NO 39
<211> LENGTH: 390
<212> TYPE: DNA
<213> ORGANISM: Pinus radiata

<400> SEQUENCE: 39

```
cagctgttta agagaacagg aagtttggat aaaagttttg aagccattcc tagagcatca     60
agaaatgaca gatgcatga gaatgagaac aggacaccta gtagggtatc agcattgttt    120
tccggtacac aggataaatg tgttgcatgt gggaagacag tgtaccccat tgagaaggtt    180
gctgttgatg gtacatcata ccaccgacca tgcttcaagt gctgtcatgg tggttgtgtc    240
atcagcccct caaattatgt tgctcatgaa ggcaggctat attgtaggca tcatagctct    300 caactttta gggagaaagg taacttcagc cagctttcaa aggcaacacc tacaaaaggg    360
gtgactgaga actcagacac agacgacaag                                      390
```

<210> SEQ ID NO 40
<211> LENGTH: 164
<212> TYPE: DNA
<213> ORGANISM: Eucalyptus grandis

<400> SEQUENCE: 40

```
ggcttcccctt tcttatcctc cattctcctc tctccttctc cttacactca cagacacaat     60
cacagagaga gagagagaga gagagagaga gagagagaga gaatggcatt cgcaggaaca    120
acccagaagt gcatggcctg tgagaagaca gtctatctgg tgga                     164
```

<210> SEQ ID NO 41
<211> LENGTH: 455
<212> TYPE: DNA
<213> ORGANISM: Eucalyptus grandis

<400> SEQUENCE: 41

```
ggcttcccctt tcttatcctc cattctcctc tctccttctc cttacactca cagacacaat     60
cacagagaga gagagagaga gagagagaga gagagagaga gaatggcatt cgcaggaaca    120
acccagaagt gcatggcctg tgagaagaca gtctatctgg tggacaagct cacagctgac    180
aatagaatct accacaaggc ctgcttcaga tgccaccatt gcaagggac tctcaagctt    240 gggaactata attcatttga aggagtcttg tactgccggc cgcatttcga tcagctcttc    300
aagagaactg gcagcctcga aaaaagcttt gaaggaaccc ccaagattgc aaagccagag    360
aaacccgtcg atggagagag acctgcagcg accaaagcct ccagtatgtt cggggggaacg    420 cgagacaaat gtgtaggctg taagagcacc gtcta                                455
```

<210> SEQ ID NO 42
<211> LENGTH: 551
<212> TYPE: DNA
<213> ORGANISM: Pinus radiata

<400> SEQUENCE: 42

```
aggtttaagg aaatggcagg cacaagtgtt gctgcagcag aggtgaaggc tcagacaacc      60
caagcagagg agccggttaa ggttgtccgc catcaagaag tgggacacaa aagtcttttg     120
cagagcgatg ccctctatca gtatatattg gaaacgagcg tgtaccctcg tgagcccgag     180
ccaatgaagg agctccgcga agtgactgcc aagcatccct ggaacctcat gactacttct     240
gccgatgagg gtcaatttct gggcctcctg ctgaagctca ttaacgccaa gaacaccatg     300
gagattgggg tgtacactgg ttactcgctt ctcagcacag cccttgcatt gcccgatgat     360
ggaaagattc tagccatgga catcaacaga gagaactatg atatcggatt gcctattatt     420
gagaaagcag gagttgccca caagattgac ttcagagagg ccctgctct gccagttctg      480 gacgaactgc ttaagaatga ggacatgcat ggatcgttcg attttgtgtt cgtggatgcg     540
gacaaagaca a                                                          551
```

<210> SEQ ID NO 43
<211> LENGTH: 225
<212> TYPE: DNA
<213> ORGANISM: Pinus radiata

<400> SEQUENCE: 43

```
gaaggaattt ggtaggcaac tatgtatatc actatattat atgcattttc tcgagatgtc      60
taatctcatt tgtgtcccac ctccctggac cggctaatga tttgactatc tttgttttaa     120
aggaagcaaa cttggtgtag gattctctcc aacttcaatg atgcaataag caagaggata     180
aatgtcatta tctttcatgg acggagcaca atggcttttt acac                      225
```

<210> SEQ ID NO 44
<211> LENGTH: 161
<212> TYPE: DNA
<213> ORGANISM: Eucalyptus grandis

<400> SEQUENCE: 44

```
tcgcaccaga aaggagatct caaaatcaag cattgatgaa atgagaaact acccttaata      60
ctttccttcc tttctatttt ttccatcttc tgtcttatgt tgtctttgaa ccattgagca     120
tgtatttgta ttcaaatgaa cgattaagga ttgagaagaa c                         161
```

<210> SEQ ID NO 45
<211> LENGTH: 289
<212> TYPE: DNA
<213> ORGANISM: Eucalyptus grandis

<400> SEQUENCE: 45

```
cacccggtg aagcagtgcc tgtacgaaac tgtcaagagc ttgcaggaga aaggccacct       60 accgtccct ccccgccgg aagattcggt gcgtattcag gatgatcctt agatccatca      120
cggtgcgcat ttgtaatccg gagaaatgag agaaacatgt gggaatttgt ttgtacttt     180 ctaagtcaaa cctggagata ccaaccctga gttctgcatt ggaatggaag ttgtcaattg     240
atcaatcgtc gcaagttatc gttggcagaa acggaatgtc agttaccat                289
```

<210> SEQ ID NO 46
<211> LENGTH: 601
<212> TYPE: DNA
<213> ORGANISM: Eucalyptus grandis

<400> SEQUENCE: 46

```
gaagcttggc gcatcgctcg ccatggcgga gcacatcccg tggcttcgct ggatgttccc      60
```

```
gctggaggag gaagcgttcg ccaagcacag cgcgaggagg gaccgcctca cccgggccat    120
catggaggag cacacggtag cccgccagaa gagcggggcc aagcagcatt tcgtcgacgc    180
cctgctcacc ctcaaggaca aatacgacct cagcgaagat accatcatag gactcctctg    240
ggacatgatc acagcaggca tggacactac tgctatttca gtggagtggg cgatggcgga    300
gctgatcaag aacccgaggg tgcaacagaa ggcccaagag gagctcgacc gggtcgtcgg    360
gttcgagcgt gtggtgactg agtccgactt ctcgaacctc ccttacctcc agtgcattgc    420
taaggaagcg ctccggctgc accctccgac cccgctgatg ctcccccacc ggtccaactc    480
ccacgtcaag atcggcggct acgacatccc caaggggtcg aacgtccacg tgaatgtatg    540
ggccatcgcc cgcgacccgg ccgtctggaa tagcccgctc gagttcaggc ccgagcggtt    600
c                                                                   601

<210> SEQ ID NO 47
<211> LENGTH: 602
<212> TYPE: DNA
<213> ORGANISM: Eucalyptus grandis

<400> SEQUENCE: 47
ccctgaggct ccggatggcg atcccgctcc tcgtgcccca catgaacctc cacgacgcca     60
agctcggggg ctacgacatc cccgccgaga gcaagatcct ggtcaacgcg tggtggctgg    120
ccaacaaccc tgcccactgg aagaagcccg aggagttccg gcccgagcgg ttcctggagg    180
aggaggcgaa ggtcgaggcc aacgggaacg acttccggta cctccccttc ggagtcggcc    240
ggaggagctg ccctgggatc atcctggccc tgcccatcct cggggtcacc atcggccagt    300
tggtgcagaa cttcgagctc ttgccgcccc ctggacaatc gaagctcgac accactgaga    360
agggtggcca attcagcttg cacatattga agcactccac catcgtcttg aagccaagat    420
ccttttgaag ttagtctcca cagagattca acttttggtg gctgttgatt tcacttggac    480
agtattaaaa tatgaagaat tggacaaagc atattcagga gttgccatga gaacttatgt    540
tgtgtcttgt gttgggaaaa taacagcttt tatgtccttt gagaactgaa acttatcttt    600
tg                                                                  602

<210> SEQ ID NO 48
<211> LENGTH: 668
<212> TYPE: DNA
<213> ORGANISM: Pinus radiata

<400> SEQUENCE: 48
attcaattct tcccactgca ggctacattt gtcagacacg ttttccgcca tttttcgcct     60
gtttctgcgg agaatttgat caggttcgga ttgggattga atcaattgaa aggttttat    120 tttcagtatt tcgatcgcca tggccaacgg aatcaagaag gtcgagcatc tgtacagatc    180
gaagcttccc gatatcgaga tctccgacca tctgcctctt cattcgtatt gctttgagag    240
agtagcggaa ttcgcagaca gaccctgtct gatcgatggg gcgacagaca gaacttattg    300
cttttcagag gtggaactga tttctcgcaa ggtcgctgcc ggtctggcga agctcgggtt    360
gcagcagggg caggttgtca tgcttctcct tccgaattgc atcgaatttg cgtttgtgtt    420 catggggggcc tctgtccggg gcgccattgt gaccacggcc aatcctttct acaagccggg    480
cgagatcgcc aaacaggcca aggccgcggg cgcgcgcatc atagttaccc tggcagctta    540
tgttgagaaa ctggccgatc tgcagagcca cgatgtgctc gtcatcacaa tcgatgatgc    600
tcccaaggaa ggttgccaac atatttccgt tctgaccgaa gccgacgaaa cccaatgccc    660
``` ggccgtga                                                              668

<210> SEQ ID NO 49
<211> LENGTH: 6629
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 49
cgccggcgtt gtggatacct cgcggaaaac ttggccctca ctgacagatg aggggcggac    60
gttgacactt gaggggccga ctcacccggc gcggcgttga cagatgaggg gcaggctcga   120
tttcggccgg cgacgtggag ctggccagcc tcgcaaatcg gcgaaaacgc ctgattttac   180
gcgagtttcc cacagatgat gtggacaagc tggggataa gtgccctgcg gtattgacac   240
ttgaggggcg cgactactga cagatgaggg gcgcgatcct tgacacttga ggggcagagt   300
gctgacagat gaggggcgca cctattgaca tttgaggggc tgtccacagg cagaaaatcc   360
agcatttgca agggtttccg cccgtttttc ggccaccgct aacctgtctt ttaacctgct   420
tttaaaccaa tatttataaa ccttgttttt aaccagggct gcgccctgtg cgcgtgaccg   480
cgcacgccga agggggtgc cccccttct cgaaccctcc cggcccgcta acgcgggcct   540
cccatccccc caggggctgc gccctcggc gcgaacggc ctcaccccaa aaatggcagc   600
gctggcagtc cataattgtg gtttcaaaat cggctccgtc gatactatgt tatacgccaa   660
cttttgaaaac aactttgaaa aagctgtttt ctggtattta aggttttaga atgcaaggaa   720
cagtgaattg gagttcgtct tgttataatt agcttcttgg ggtatcttta aatactgtag   780
aaaagaggaa ggaaataata aatggctaaa atgagaatat caccggaatt gaaaaaactg   840
atcgaaaaat accgctgcgt aaaagatacg aaggaatgt ctcctgctaa ggtatataag   900
ctggtgggag aaaatgaaaa cctatattta aaaatgacgg acagccggta taaagggacc   960
acctatgatg tggaacggga aaaggacatg atgctatggc tggaaggaaa gctgcctgtt  1020
ccaaaggtcc tgcactttga acggcatgat ggctggagca atctgctcat gagtgaggcc  1080
gatggcgtcc tttgctcgga agagtatgaa gatgaacaaa gccctgaaaa gattatcgag  1140
ctgtatgcgg agtgcatcag gctctttcac tccatcgaca tatcggattg tccctatacg  1200
aatagcttag acagccgctt agccgaattg gattacttac tgaataacga tctggccgat  1260
gtggattgcg aaaactggga agaagacact ccatttaaag atccgcgcga gctgtatgat  1320
ttttttaaaga cggaaaagcc cgaagaggaa cttgtctttt cccacggcga cctgggagac  1380
agcaacatct tgtgaaaga tgcaaagta agtggcttta ttgatcttgg agaagcggc    1440
agggcggaca agtggtatga cattgccttc tgcgtccggt cgatcaggga ggatatcggg  1500
gaagaacagt atgtcgagct attttttgac ttactgggga tcaagcctga ttgggagaaa  1560
ataaaatatt atatttact ggatgaattg tttagtacc tagatgtggc gcaacgatgc  1620
cggcgacaag caggagcgca ccgacttctt ccgcatcaag tgttttggct ctcaggccga  1680
ggcccacggc aagtatttgg gcaagggtc gctggtattc gtgcagggca agattcggaa  1740
taccaagtac gagaaggacg gccagacggt ctacgggacc gacttcattg ccgataaggt  1800
ggattatctg gacaccaagg caccaggcgg gtcaaatcag gaataagggc acattgcccc  1860
ggcgtgagtc gggggcaatcc cgcaaggagg gtgaatgaat cggacgtttg accggaaggc  1920
atacaggcaa gaactgatcg acgcggggtt ttccgccgag gatgccgaaa ccatcgcaag  1980

```
ccgcaccgtc atgcgtgcgc cccgcgaaac cttccagtcc gtcggctcga tggtccagca   2040
agctacggcc aagatcgagc gcgacagcgt gcaactggct ccccctgccc tgcccgcgcc   2100
atcggccgcc gtggagcgtt cgcgtcgtct cgaacaggag gcggcaggtt tggcgaagtc   2160
gatgaccatc gacacgcgag gaactatgac gaccaagaag cgaaaaaccg ccggcgagga   2220
cctggcaaaa caggtcagcg aggccaagca ggccgcgttg ctgaaacaca cgaagcagca   2280
gatcaaggaa atgcagcttt ccttgttcga tattgcgccg tggccggaca cgatgcgagc   2340
gatgccaaac gacacggccc gctctgccct gttcaccacg cgcaacaaga aaatcccgcg   2400
cgaggcgctg caaaacaagg tcattttcca cgtcaacaag gacgtgaaga tcacctacac   2460
cggcgtcgag ctgcgggccg acgatgacga actggtgtgg cagcaggtgt tggagtacgc   2520
gaagcgcacc cctatcggcg agccgatcac cttcacgttc tacgagcttt gccaggacct   2580
gggctggtcg atcaatggcc ggtattacac gaaggccgag gaatgcctgt cgcgcctaca   2640
ggcgacggcg atgggcttca cgtccgaccg cgttgggcac ctggaatcgg tgtcgctgct   2700
gcaccgcttc cgcgtcctgg accgtggcaa gaaaacgtcc cgttgccagg tcctgatcga   2760
cgaggaaatc gtcgtgctgt ttgctggcga ccactacacg aaattcatat gggagaagta   2820
ccgcaagctg tcgccgacgg cccgacggat gttcgactat ttcagctcgc accgggagcc   2880
gtacccgctc aagctggaaa ccttccgcct catgtgcgga tcggattcca cccgcgtgaa   2940
gaagtggcgc gagcaggtcg gcgaagcctg cgaagagttg cgaggcagcg gctggtgga   3000 acacgcctgg gtcaatgatg acctggtgca ttgcaaacgc tagggccttg tggggtcagt   3060
tccggctggg ggttcagcag ccagcgcttt actggcattt caggaacaag cgggcactgc   3120
tcgacgcact tgcttcgctc agtatcgctc gggacgcacg gcgcgctcta cgaactgccg   3180
atagacaact gtcacggtta agcgagaaat gaataagaag gctgataatt cggatctctg   3240
cgagggagat gatatttgat cacaggcagc aacgctctgt catcgttaca atcaacatgc   3300
taccctccgc gagatcatcc gtgtttcaaa cccggcagct tagttgccgt tcttccgaat   3360
agcatcggta acatgagcaa agtctgccgc cttacaacgg ctctcccgct gacgccgtcc   3420
cggactgatg ggctgcctgt atcgagtggt gattttgtgc cgagctgccg gtcggggagc   3480
tgttggctgg ctggtggcag gatatattgt ggtgtaaaca aattgacgct tagacaactt   3540
aataacacac cgcggtctag aactagtgga tcccccctac gtgcgatcta gtaacataga   3600
tgacaccgcg cgcgataatt tatcctagtt tgcgcgctat attttgtttt ctatcgcgta   3660
ttaaatgtat aattgcggga ctctaatcat aaaaacccat ctcataaata acgtcatgca   3720
ttacatgtta attattacat gcttaacgta attcaacaga aattatatga taatcatcgc   3780
aagaccggca acaggattca atcttaagaa actttattgc caaatgtttg aacgatccct   3840
cagaagaact cgtcaagaag gcgatagaag gcgatgcgct gcgaatcggg agcggcgata   3900
ccgtaaagca cgaggaagcg gtcagcccat tcgccgccaa gctcttcagc aatatcacgg   3960
gtagccaacg ctatgtcctg atagcggtcc gccacaccca gccggccaca gtcgatgaat   4020
ccagaaaagc ggccattttc caccatgata ttcggcaagc aggcatcgcc atgggtcacg   4080
acgagatcct cgccgtcggg catgcgcgcc ttgagcctgg cgaacagttc ggctggcgcg   4140
agcccctgat gctcttcgtc cagatcatcc tgatcgacaa gaccggcttc catccgagta   4200
cgtgctcgct cgatgcgatg tttcgcttgg tggtcgaatg ggcaggtagc cggatcaagc   4260
gtatgcagcc gccgcattgc atcagccatg atggatactt tctcggcagg agcaaggtga   4320
```

```
gatgacagga gatcctgccc cggcacttcg cccaatagca gccagtccct tcccgcttca    4380
gtgacaacgt cgagcacagc tgcgcaagga acgcccgtcg tggccagcca cgatagccgc    4440
gctgcctcgt cctggagttc attcagggca ccggacaggt cggtcttgac aaaaagaacc    4500
gggcgcccct gcgctgacag ccggaacacg cggcatcag agcagccgat tgtctgttgt     4560
gcccagtcat agccgaatag cctctccacc caagcggccg gagaacctgc gtgcaatcca    4620
tcttgttcaa tcatagtact agttggggat ctgcatctga ataaaacaa tagaacaagt     4680
agaaaccaat cagcgaacat ataccaaatc aaagccgta agagaaatca aacaacacc      4740
aaagagaaac ggatctaaac ataagaaacc taaaacagag agaatcgaac aaagaaaaca    4800
caaaaattga atagatcgtc cttgaaaatc ctaatttcac aatcaagcaa gaaattacac    4860
agatgtaaac actacgaatc gatatcttag taatcaggac aaaatttaga agctggattg    4920
acgaaacgaa caatattgtc aaaagcaatt tatacaaaag attcaataat ccacataaca    4980
aaaattggag atcagatacg aatcaaaaac aaaagaatc agaaaatata ccttgaaaga     5040
gagagtcgcg agagatttgc agagatcgct ttaggctttg ggagagattg aagagtcaga    5100
aaaagacgaa aggatgaatt attatcttcc acacgaaggt cttctttata tcgcaaacca    5160
aaagcccaaa accgtctttt ctattaatga gaataaaata tctttagcca aaacaaaaaa    5220
aggaagatat cagttgagga ttattatcac gaaactaaag gaaggaatca tatgatacgt    5280
gtctattttc caccgtgcgt ttttaaaaga ccgactcaag tagaaacatc ctatggtggt    5340
ggttggatta ggtcatccat tacatctgct tcactgacat ttttctattt ttcttttttgt   5400
atatacttt cctcaaataa tttctttctt ttctatagaa gaatttaatc aataaggaaa    5460
aagttcaaaa aagattcttt ccattaagac tatgtcttgg ttaacccaac ccattaagaa    5520
taagcaatca taatatatat agagaatact aatactatat atgagatttt tcttttaatt    5580
tcatgttgat tatgatagtt tatcttcttg atttaattta tcaatacttg gcataaaaga    5640
ttctaatcta ctctaataaa gaaaagaaaa aaaagtatct accattgact aattaaaata    5700
aggaaactta tctaccaaat ttgagtattt tttagaacaa tcttttggt ttaattccaa     5760
aactctaaac ctaattgttg ggaaaaagga cctaattttt aagaaaagtt aataattaga    5820
agatctgtat gttttttttt ttgatccaag tttttatttc ttttctcttt ttttcatgat    5880
aaaatctatg ttttttttagt ctacaattaa agtaattgtt attattttct ttatcttttt   5940
ttgttgttgt tgttaattcc cttttttttt ttttaacagc aacttcttaa aaaaaaaaac    6000
agttgggcct tgaatttatt tcaggcctgc gttattaagc ccagataata actcaaaaca    6060
aaaaaaatgt tgaaccggaa taaacccgcg agattaaatg ccggttttca ggtaacatag    6120
aagaagaata tatgaggatt gaagaagtat tcaagaggcg gaacaattca caagtccaag    6180
agcttaaatt tctcctcact cttctgctac agactcggaa ctctttctct ttgctaaaat    6240
aagatgttca ggattttgt tgcccgacaa ttcatgtatc tcacactctc tctcttctct     6300
gttcttacta ctctgttaca ttaccaccaa ctcaagactt tcttccacaa tggcgtttat    6360
gagacttggc tccaaatccg aagcttatcg ataccgtcga cctctagagg cgcgccaagc    6420
ggccgcattt aaatgggccc tcgagagccc gggctcctgc aggtacctta attaaaagtt    6480
taaactatca gtgtttgaca ggatatattg gcgggtaaac ctaagagaaa agagcgttta    6540
ttagaataat cggatattta aagggcgtg aaaaggttta ccgttcgtc catttgtatg      6600
tgcatgccaa ccacagggtt ccccagatc                                      6629
```

```
<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gagagaccat aattgtggtc caatttgcag ccgtccgag                            39

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gagagaccat aattgtggtt tgtgtttcca tattgttcat c                         41

<210> SEQ ID NO 52
<211> LENGTH: 1878
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 52
ggcgcgccgt caacggatca ggatatcctt gtttaagatg ttgaactcta tggaggtttg     60
tatgaactga tgatctagga ccggataagt tcccttcttc atagcgaact tattcaaaga    120
atgttttgtg tatcattctt gttacattgt tattaatgaa aaatattat tggtcattgg    180 actgaacacg agtgttaaat atggaccagg ccccaaataa gatccattga tatatgaatt    240
aaataacaag aataaatcga gtcaccaaac cacttgcctt ttttaacgag acttgttcac    300
caacttgata caaaagtcat tatcctatgc aaatcaataa tcatacaaaa atatccaata    360
acactaaaaa attaaaagaa atggataatt tcacaatatg ttatacgata agaagttac    420 ttttccaaga aattcactga ttttataagc ccacttgcat tagataaatg gcaaaaaaaa    480
acaaaaagga aaagaaataa agcacgaaga attctagaaa atacgaaata cgcttcaatg    540
cagtgggacc cacggttcaa ttattgccaa ttttcagctc caccgtatat ttaaaaaata    600
aaacgataat gctaaaaaaa tataaatcgt aacgatcgtt aaatctcaac ggctggatct    660
tatgacgacc gttagaaatt gtggttgtcg acgagtcagt aataaacggc gtcaaagtgg    720
ttgcagccgg cacacacgag tcgtgtttat caactcaaag cacaaatact tttcctcaac    780
ctaaaaataa ggcaattagc caaaaacaac tttgcgtgta acaacgctc aatacacgtg    840 tcatttatt attagctatt gcttcaccgc cttagctttc tcgtgaccta gtcgtcctcg    900
tcttttcttc ttcttcttct ataaaacaat acccaaagag ctcttcttct tcacaattca    960
gatttcaatt tctcaaaatc ttaaaaactt tctctcaatt ctctctaccg tgatcaaggt   1020
aaatttctgt gttccttatt ctctcaaaat cttcgatttt gttttcgttc gatcccaatt   1080
tcgtatatgt tctttggttt agattctgtt aatcttagat cgaagacgat tttctgggtt   1140
tgatcgttag atatcatctt aattctcgat tagggtttca taaatatcat ccgatttgtt   1200
caaataattt gagtttgtc gaataattac tcttcgattt gtgatttcta tctagatctg   1260
gtgttagttt ctagtttgtg cgatcgaatt tgtcgattaa tctgagtttt tctgattaac   1320
```

```
agatgattga acaagatgga ttgcacgcag ttctccggc cgcttgggtg gagaggctat    1380
tcggctatga ctgggcacaa cagacaatcg gctgctctga tgccgccgtg ttccggctgt    1440
cagcgcaggg gcgcccggtt cttttgtca agaccgacct gtccggtgcc ctgaatgaac     1500
tccaggacga ggcagcgcgg ctatcgtggc tggccacgac gggcgttcct tgcgcagctg    1560
tgctcgacgt tgtcactgaa gcgggaaggg actggctgct attgggcgaa gtgccggggc    1620
aggatctcct gtcatctcac cttgctcctg ccgagaaagt atccatcatg gctgatgcaa    1680
tgcggcggct gcatacgctt gatccggcta cctgcccatt cgaccaccaa gcgaaacatc    1740
gcatcgagcg agcacgtact cggatggaag cgatcaggat gatctggacg aagagcatca    1800
ggggctcgcg ccagccgaac tgttcgccag gctcaaggcg cgcatgcccg acggcgagga    1860
tctcgtcgtg acccatgg                                                  1878
```

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
gagaggcgcg ccgtcaacgg atcaggatat ccttgtttaa ga                       42
```

<210> SEQ ID NO 54
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
tgctggcaat ccatcttgtt caatcatctg ttaatcagaa aaactcagat ta            52
```

<210> SEQ ID NO 55
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

```
taatctgagt ttttctgatt aacagatgat tgaacaagat ggattgcacg ca            52
```

<210> SEQ ID NO 56
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
tattgccaaa tgtttgaacg atccctcaga agaactcgtc aagaaggcga ta            52
```

<210> SEQ ID NO 57
<211> LENGTH: 52
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 57
tatcgccttc ttgacgagtt cttctgaggg atcgttcaaa catttggcaa ta          52

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gagacactac gtgcgatcta gtaacataga tgacac                            36

<210> SEQ ID NO 59
<211> LENGTH: 12290
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 59
cgccggcgtt gtggatacct cgcggaaaac ttggccctca ctgacagatg aggggcggac    60
gttgacactt gaggggccga ctcacccggc gcggcgttga cagatgaggg gcaggctcga   120
tttcggccgg cgacgtggag ctggccagcc tcgcaaatcg gcgaaaacgc ctgattttac   180
gcgagtttcc cacagatgat gtggacaagc ctggggataa gtgccctgcg gtattgacac   240
ttgaggggcg cgactactga cagatgaggg gcgcgatcct tgacacttga ggggcagagt   300
gctgacagat gaggggcgca cctattgaca tttgaggggc tgtccacagg cagaaaatcc   360
agcatttgca aggtttccg cccgtttttc ggccaccgct aacctgtctt ttaacctgct   420
tttaaaccaa tatttataaa ccttgttttt aaccagggct gcgccctgtg cgcgtgaccg   480
cgcacgccga agggggtgc cccccttct cgaaccctcc cggcccgcta acgcgggcct   540
cccatccccc caggggctgc gcccctcggc cgcgaacggc ctcaccccaa aaatggcagc   600
gctggcagtc cataattgtg gtccaatttg cagccgtccg agacaggagg acatcgtcca   660
gctgaaaccg gggcagaatc cggccatttc tgaagagaaa aatggtaaac tgatagaata   720
aaatcataag aaaggagccg cacatgaaaa aagcagtcat taacggggaa caaatcagaa   780
gtatcagcga cctccaccag acattgaaaa aggagcttgc ccttccggaa tactacggtg   840
aaaacctgga cgctttatgg gattgtctga ccggatgggt ggagtacccg ctcgttttgg   900
aatggaggca gtttgaacaa gcaagcagc tgactgaaaa tggcgccgag agtgtgcttc   960
aggttttccg tgaagcgaaa gcggaaggct gcgacatcac catcatactt tcttaatacg  1020
atcaatggga gatgaacaat atggaaacac aaaccacaat tgtggtttca aaatcggctc  1080
cgtcgatact atgttatacg ccaactttga aaacaacttt gaaaaagctg ttttctggta  1140
tttaaggttt tagaatgcaa ggaacagtga attggagttc gtcttgttat aattagcttc  1200
ttggggtatc tttaaatact gtagaaaaga ggaaggaaat aataaatggc taaaatgaga  1260
atatcaccgg aattgaaaaa actgatcgaa aaataccgct gcgtaaaaga tacggaagga  1320
atgtctcctg ctaaggtata taagctggtg ggagaaaatg aaaacctata tttaaaaatg  1380
acggacagcc ggtataaagg gaccacctat gatgtggaac gggaaaagga catgatgcta  1440

```
tggctggaag gaaagctgcc tgttccaaag gtcctgcact ttgaacggca tgatggctgg    1500
agcaatctgc tcatgagtga ggccgatggc gtcctttgct cggaagagta tgaagatgaa    1560
caaagccctg aaaagattat cgagctgtat gcggagtgca tcaggctctt tcactccatc    1620
gacatatcgg attgtcccta tacgaatagc ttagacagcc gcttagccga attggattac    1680
ttactgaata acgatctggc cgatgtggat tgcgaaaact gggaagaaga cactccattt    1740
aaagatccgc gcgagctgta tgatttttta aagacggaaa agcccgaaga ggaacttgtc    1800
ttttcccacg gcgacctggg agacagcaac atctttgtga agatggcaa agtaagtggc    1860 tttattgatc ttgggagaag cggcagggcg acaagtggt atgacattgc cttctgcgtc    1920
cggtcgatca gggaggatat cggggaagaa cagtatgtcg agctattttt tgacttactg    1980
gggatcaagc ctgattggga gaaaataaaa tattatattt tactggatga attgttttag    2040
tacctagatg tggcgcaacg atgccggcga caagcaggag cgcaccgact tcttccgcat    2100
caagtgtttt ggctctcagg ccgaggccca cggcaagtat ttgggcaagg ggtcgctggt    2160
attcgtgcag ggcaagattc ggaataccaa gtacgagaag gacggccaga cggtctacgg    2220
gaccgacttc attgccgata aggtggatta tctggacacc aaggcaccag gcgggtcaaa    2280
tcaggaataa gggcacattg ccccggcgtg agtcggggca atcccgcaag gagggtgaat    2340
gaatcggacg tttgaccgga aggcatacag gcaagaactg atcgacgcgg ggttttccgc    2400
cgaggatgcc gaaaccatcg caagccgcac cgtcatgcgt gcgccccgcg aaaccttcca    2460
gtccgtcggc tcgatggtcc agcaagctac ggccaagatc gagcgcgaca gcgtgcaact    2520
ggctccccct gccctgcccg cgccatcggc cgccgtggag cgttcgcgtc gtctcgaaca    2580
ggaggcggca ggtttggcga agtcgatgac catcgacacg cgaggaacta tgacgaccaa    2640
gaagcgaaaa accgccggcg aggacctggc aaaacaggtc agcgaggcca agcaggccgc    2700
gttgctgaaa cacacgaagc agcagatcaa ggaaatgcag cttttccttgt tcgatattgc    2760 gccgtggccg gacacgatgc gagcgatgcc aaacgacacg gcccgctctg ccctgttcac    2820
cacgcgcaac aagaaaatcc gcgcgaggc gctgcaaaac aaggtcattt tccacgtcaa    2880
caaggacgtg aagatcacct acaccggcgt cgagctgcgg gccgacgatg acgaactggt    2940
gtggcagcag gtgttggagt acgcgaagcg cacccctatc ggcgagccga tcaccttcac    3000
gttctacgag ctttgccagg acctgggctg gtcgatcaat ggccggtatt acacgaaggc    3060
cgaggaatgc ctgtcgcgcc tacaggcgac ggcgatgggc ttcacgtccg accgcgttgg    3120
gcacctggaa tcggtgtcgc tgctgcaccg cttccgcgtc ctggaccgtg caagaaaac    3180 gtcccgttgc caggtcctga tcgacgagga aatcgtcgtg ctgtttgctg gcgaccacta    3240
cacgaaattc atatgggaga agtaccgcaa gctgtcgccg acggcccgac ggatgttcga    3300
ctatttcagc tcgcaccggg agccgtaccc gctcaagctg gaaaccttcc gcctcatgtg    3360
cggatcggat tccacccgcg tgaagaagtg gcgcgagcag gtcggcgaag cctgcgaaga    3420
gttgcgaggc agcggcctgg tggaacacgc ctgggtcaat gatgacctgg tgcattgcaa    3480
acgctagggc cttgtggggt cagttccggc tgggggttca gcagccagcg ctttactggc    3540
atttcaggaa caagcgggca ctgctcgacg cacttgcttc gctcagtatc gctcgggacg    3600
cacggcgcgc tctacgaact gccgatagac aactgtcacg gttaagcgag aaatgaataa    3660
gaaggctgat aattcggatc tctgcgaggg agatgatatt tgatccggtg tgaaataccg    3720
cacagatgcg taaggagaaa ataccgcatc aggcgctctt ccgcttcctc gctcactgac    3780
tcgctgcgct cggtcgttcg gctgcggcga gcggtatcag ctcactcaaa ggcggtaata    3840
```

```
cggttatcca cagaatcagg ggataacgca ggaaagaaca tgtgagcaaa aggccagcaa   3900
aaggccagga accgtaaaaa ggccgcgttg ctggcgtttt tccataggct ccgcccccct   3960
gacgagcatc acaaaaatcg acgctcaagt cagaggtggc gaaacccgac aggactataa   4020
agataccagg cgtttccccc tggaagctcc ctcgtgcgct ctcctgttcc gaccctgccg   4080
cttaccggat acctgtccgc ctttctccct tcgggaagcg tggcgctttc tcatagctca   4140
cgctgtaggt atctcagttc ggtgtaggtc gttcgctcca agctgggctg tgtgcacgaa   4200
ccccccgttc agcccgaccg ctgcgcctta tccggtaact atcgtcttga gtccaacccg   4260
gtaagacacg acttatcgcc actggcagca gccactggta acaggattag cagagcgagg   4320
tatgtaggcg gtgctacaga gttcttgaag tggtggccta actacggcta cactagaagg   4380
acagtatttg gtatctgcgc tctgctgaag ccagttacct tcggaaaaag agttggtagc   4440
tcttgatccg gcaaacaaac caccgctggt agcggtggtt tttttgtttg caagcagcag   4500
attacgcgca gaaaaaagg atatcaagaa gatcctttga tcttttctac ggggtctgac   4560
gctcagtgga acgaaaactc acgttaaggg attttggtca tgagattatc aaaaaggatc   4620
ttcacctaga tccttttaaa ttaaaaatga agttttaaat caatctaaag tatatatgag   4680
taaacttggt ctgacagtta ccaatgcttc atcagtgagg ctgatcacag cagcaacgc   4740 tctgtcatcg ttacaatcaa catgctaccc tccgcgagat catccgtgtt tcaaacccgg   4800
cagcttagtt gccgttcttc cgaatagcat cggtaacatg agcaaagtct gccgccttac   4860
aacggctctc ccgctgacgc cgtcccggac tgatgggctg cctgtatcga gtggtgattt   4920
tgtgccgagc tgccggtcgg ggagctgttg gctggctggt ggcaggatat attgtggtgt   4980
aaacaaattg acgcttagac aacttaataa cacaccgcgg tctagaacta gtggatcccc   5040
cctacgtgcg atctagtaac atagatgaca ccgcgcgcga taatttatcc tagtttgcgc   5100
gctatatttt gttttctatc gcgtattaaa tgtataattg cgggactcta atcataaaaa   5160
cccatctcat aaataacgtc atgcattaca tgttaattat tacatgctta acgtaattca   5220
acagaaatta tatgataatc atcgcaagac cggcaacagg attcaatctt aagaaacttt   5280
attgccaaat gtttgaacga tccctcagaa gaactcgtca agaaggcgat agaaggcgat   5340
gcgctgcgaa tcgggagcgg cgataccgta aagcacgagg aagcggtcag cccattcgcc   5400
gccaagctct tcagcaatat cacgggtagc caacgctatg tcctgatagc ggtccgccac   5460
acccagccgg ccacagtcga tgaatccaga aaagcggcca ttttccacca tgatattcgg   5520
caagcaggca tcgccatggg tcacgacgag atcctcgccg tcgggcatgc gcgccttgag   5580
cctggcgaac agttcggctg cgcgagccc ctgatgctct tcgtccagat catcctgatc   5640
gacaagaccg gcttccatcc gagtacgtgc tcgctcgatg cgatgtttcg cttggtggtc   5700
gaatgggcag gtagccggat caagcgtatg cagccgccgc attgcatcag ccatgatgga   5760
tactttctcg gcaggagcaa ggtgagatga caggagatcc tgccccggca cttcgcccaa   5820
tagcagccag tcccttcccg cttcagtgac aacgtcgagc acagctgcgc aaggaacgcc   5880
cgtcgtggcc agccacgata gccgcgctgc ctcgtcctgg agttcattca gggcaccgga   5940
caggtcggtc ttgacaaaaa gaaccggcg ccctgcgct gacagccgga acacggcggc   6000
atcagagcag ccgattgtct gttgtgccca gtcatagccg aatagcctct ccacccaagc   6060
ggccggagaa cctgcgtgca atccatcttg ttcaatcatc tgttaatcag aaaaactcag   6120
attaatcgac aaattcgatc gcacaaacta gaaactaaca ccagatctag atagaaatca   6180
```

```
caaatcgaag agtaattatt cgacaaaact caaattattt gaacaaatcg gatgatattt    6240
atgaaaccct aatcgagaat taagatgata tctaacgatc aaacccagaa aatcgtcttc    6300
gatctaagat taacagaatc taaaccaaag aacatatacg aaattgggat cgaacgaaaa    6360
caaaatcgaa gattttgaga gaataaggaa cacagaaatt taccttgatc acggtagaga    6420
gaattgagag aaagttttta agattttgag aaattgaaat ctgaattgtg aagaagaaga    6480
gctctttggg tattgtttta tagaagaaga agaagaaaag acgaggacga ctaggtcacg    6540
agaaagctaa ggcggtgaag caatagctaa taataaaatg acacgtgtat tgagcgttgt    6600
ttacacgcaa agttgttttt ggctaattgc cttattttta ggttgaggaa aagtatttgt    6660
gctttgagtt gataaacacg actcgtgtgt gccggctgca accactttga cgccgtttat    6720
tactgactcg tcgacaacca caatttctaa cggtcgtcat aagatccagc cgttgagatt    6780
taacgatcgt tacgatttat attttttag cattatcgtt ttatttttta aatatacggt    6840
ggagctgaaa attggcaata attgaaccgt gggtcccact gcattgaagc gtatttcgta    6900
ttttctagaa ttcttcgtgc tttatttctt ttcctttttg tttttttttg ccatttatct    6960
aatgcaagtg ggcttataaa atcagtgaat ttcttggaaa agtaacttct ttatcgtata    7020
acatattgtg aaattatcca tttcttttaa tttttagtg ttattggata tttttgtatg    7080
attattgatt tgcataggat aatgactttt gtatcaagtt ggtgaacaag tctcgttaaa    7140
aaaggcaagt ggtttggtga ctcgatttat tcttgttatt taattcatat atcaatggat    7200
cttatttggg gcctggtcca tatttaacac tcgtgttcag tccaatgacc aataatattt    7260
tttcattaat aacaatgtaa caagaatgat acacaaaaca ttctttgaat aagttcgcta    7320
tgaagaaggg aacttatccg gtcctagatc atcagttcat acaaacctcc atagagttca    7380
acatcttaaa caaggatatc ctgatccgtt gacggcgcgc caagcggccg catttaaatg    7440
ggccctcgag agcccaaatg cggccgcaaa accctcaca aatacataaa aaaaattctt    7500
tatttaatta tcaaactctc cactaccttt cccaccaacc gttacaatcc tgaatgttgg    7560
aaaaaactaa ctacattgat ataaaaaac tacattactt cctaaatcat atcaaaattg    7620
tataaatata tccactcaaa ggagtctaga agatccactt ggacaaattg cccatagttg    7680
gaaagatgtt caccaagtca acaagattta tcaatggaaa aatccatcta ccaaacttac    7740
tttcaagaaa atccaaggat tatagagtaa aaaatctatg tattattaag tcaaaaagaa    7800
aaccaaagtg aacaaatatt gatgtacaag tttgagagga taagacattg gaatcgtcta    7860
accaggaggc ggaggaattc cctagacagt taaaagtggc cggaatcccg gtaaaaagaa    7920 ttaaatttt tttgtagagg gagtgcttga atcatgtttt ttatgatgga aatagattca    7980
gcaccatcaa aaacattcag gacacctaaa atttttgaagt ttaacaaaaa taacttggat    8040
ctacaaaaat ccgtatcgga ttttctctaa atataactag aattttcata actttcaaag    8100
caactcctcc cctaaccgta aaacttttcc tacttcaccg ttaattacat tccttaagag    8160
tgataaagaa ataaagtaaa taaaagtatt cacaaaccaa caatttattt cttttattta    8220
cttaaaaaaa caaaaagttt atttattta cttaaatggc ataatgacat atcggagatc    8280
cctcgaacga gaatctttta tctccctggt tttgtattaa aaagtaattt attgtggggt    8340
ccacgcggag ttggaatcct acagacgcgc tttacatacg tctcgagaag cgtgacggat    8400
gtgcgaccgg atgaccctgt ataacccacc gacacagcca gcgcacagta tacacgtgtc    8460
atttctctat tggaaaatgt cgttgttatc cccgctggta cgcaaccacc gatggtgaca    8520
ggtcgtctgt tgtcgtgtcg cgtagcggga gaagggtctc atccaacgct attaaatact    8580
```

```
cgccttcacc gcgttacttc tcatctttc tcttgcgttg tataatcagt gcgatattct    8640
cagagagctt ttcattcaaa ggtatggagt tttgaagggc tttactctta acatttgttt    8700
ttctttgtaa attgttaatg gtggtttctg tgggggaaga atcttttgcc aggtccttt     8760 gggtttcgca tgtttatttg ggttatttt ctcgactatg gctgacatta ctaggcttt     8820 cgtgctttca tctgtgtttt cttcccttaa taggtctgtc tctctggaat atttaatttt   8880
cgtatgtaag ttatgagtag tcgctgtttg taataggctc ttgtctgtaa aggtttcagc   8940
aggtgtttgc gttttattgc gtcatgtgtt tcagaaggcc tttgcagatt attgcgttgt   9000
actttaatat tttgtctcca accttgttat agtttccctc ctttgatctc acaggaaccc   9060
tttcttcttt gagcattttc ttgtggcgtt ctgtagtaat attttaattt tgggcccggg   9120
ttctgagggt aggtgattat tcacagtgat gtgctttccc tataaggtcc tctatgtgta   9180
agctgttagg gtttgtgcgt tactattgac atgtcacatg tcacatattt tcttcctctt   9240
atccttcgaa ctgatggttc ttttttctaat tcgtggattg ctggtgccat attttatttc   9300
tattgcaact gtattttagg gtgtctcttt cttttgatt tcttgttaat atttgtgttc    9360
aggttgtaac tatgggttgc tagggtgtct gccctcttct tttgtgcttc tttcgcagaa   9420
tctgtccgtt ggtctgtatt tgggtgatga attatttatt ccttgaagta tctgtctaat   9480
tagcttgtga tgatgtgcag gtatattcgt tagtcatatt tcaatttcaa gcgatccccc   9540
gggcccccat ggatccagta gaaaccccaa cccgtgaaat caaaaaactc gacggcctgt   9600
gggcattcag tctggatcgc gaaaactgtg gaattggtca gcgttggtgg gaaagcgcgt   9660
tacaagaaag ccgggcaatt gctgtgccag gcagttttaa cgatcagttc gccgatgcag   9720
atattcgtaa ttatgcgggc aacgtctggt atcagcgcga agtctttata ccgaaaggtt   9780
gggcaggcca gcgtatcgtg ctgcgtttcg atgcggtcac tcattacggc aaagtgtggg   9840
tcaataatca ggaagtgatg gagcatcagg gcggctatac gccatttgaa gccgatgtca   9900
cgccgtatgt tattgccggg aaaagtgtac gtaagtttct gcttctacct ttgatatata   9960
tataataatt atcattaatt agtagtaata taatatttca aatatttttt tcaaaataaa  10020
agaatgtagt atatagcaat tgcttttctg tagtttataa gtgtgtatat tttaatttat  10080
aactttccta atatatgacc aaaatttgtt gatgtgcagg tatcaccgtt tgtgtgaaca  10140
acgaactgaa ctggcagact atcccgccgg gaatggtgat taccgacgaa aacggcaaga  10200
aaaagcagtc ttacttccat gatttcttta actatgccgg aatccatcgc agcgtaatgc  10260
tctacaccac gccgaacacc tgggtggacg atatcaccgt ggtgacgcat gtcgcgcaag  10320
actgtaacca cgcgtctgtt gactggcagg tggtggccaa tggtgatgtc agcgttgaac  10380
tgcgtgatgc ggatcaacag gtggttgcaa ctggacaagg cactagcggg actttgcaag  10440
tggtgaatcc gcacctctgg caaccgggtg aaggttatct ctatgaactg tgcgtcacag  10500
ccaaaagcca gacagagtgt gatatctacc cgcttcgcgt cggcatccgg tcagtggcag  10560
tgaagggcga acagttcctg attaaccaca aaccgttcta ctttactggc tttggtcgtc  10620
atgaagatgc ggacttgcgt ggcaaaggat tcgataacgt gctgatggtg cacgaccacg  10680
cattaatgga ctggattggg gccaactcct accgtacctc gcattaccct tacgctgaag  10740
agatgctcga ctgggcagat gaacatggca tcgtggtgat tgatgaaact gctgctgtcg  10800
gctttaacct ctctttaggc attggtttcg aagcgggcaa caagccgaaa gaactgtaca  10860
gcgaagaggc agtcaacggg gaaactcagc aagcgcactt acaggcgatt aaagagctga  10920
```

```
tagcgcgtga caaaaaccac ccaagcgtgg tgatgtggag tattgccaac gaaccggata    10980
cccgtccgca aggtgcacgg gaatatttcg cgccactggc ggaagcaacg cgtaaactcg    11040
acccgacgcg tccgatcacc tgcgtcaatg taatgttctg cgacgctcac accgatacca    11100
tcagcgatct ctttgatgtg ctgtgcctga accgttatta cggatggtat gtccaaagcg    11160
gcgatttgga aacggcagag aaggtactgg aaaaagaact tctggcctgg caggagaaac    11220
tgcatcagcc gattatcatc accgaatacg gcgtggatac gttagccggg ctgcactcaa    11280
tgtacaccga catgtggagt gaagagtatc agtgtgcatg gctggatatg tatcaccgcg    11340
tctttgatcg cgtcagcgcc gtcgtcggtg aacaggtatg gaatttcgcc gattttgcga    11400
cctcgcaagg catattgcgc gttggcggta acaagaaagg gatcttcact cgcgaccgca    11460
aaccgaagtc ggcggctttt ctgctgcaaa acgctggac tggcatgaac ttcggtgaaa    11520
aaccgcagca gggaggcaaa caatgaatca acaactctcc tggcgcacca tcgtcggcta    11580
cagcctcggg aattgctacc gagggttcga atcgatgggt gttatttgt ggataataaa    11640
ttcgggtgat gttcagtgtt tgtcgtattt ctcacgaata aattgtgttt atgtatgtgt    11700
tagtgttgtt tgtctgtttc agaccctctt atgttatatt tttcttttcg tcggtcagtt    11760
gaagccaata ctggtgtcct ggccggcact gcaataccat ttcgtttaat ataaagactc    11820
tgttatccgt gagctcgaat ttccccgatc gttcaaacat ttggcaataa agtttcttaa    11880
gattgaatcc tgttgccggt cttgcgatga ttatcatata atttctgttg aattacgtta    11940
agcatgtaat aattaacatg taatgcatga cgttatttat gagatgggtt tttatgatta    12000
gagtcccgca attatacatt taatacgcga tagaaaacaa aatatagcgc gcaaactagg    12060
ataaattatc gcgcgcggtg tcatctatgt tactagatcg cggccgcatt tgggctcctg    12120
caggtacctt aattaaaagt ttaaactatc agtgtttgac aggatatatt ggcgggtaaa    12180
cctaagagaa aagagcgttt attagaataa tcggatattt aaaagggcgt gaaaaggttt    12240
atccgttcgt ccatttgtat gtgcatgcca accacagggt tccccagatc                12290
```

<210> SEQ ID NO 60
<211> LENGTH: 4289
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 60

```
cttccagggg gaaacgcctg gtatctttat agtcctgtcg ggtttcgcca cctctgactt      60
gagcgtcgat ttttgtgatg ctcgtcaggg gggcggagcc tatggaaaaa cgccagcaac     120
gcggcctttt tacggttcct ggccttttgc tggccttttg ctcacatgtt ctttcctgcg     180
ttatcccctg attctgtgga taaccgtatt accgcctttg agtgagctga taccgctcgc     240
cgcagccgaa cgaccgagcg cagcgagtca gtgagcgagg aagcggaaga gcgcccaata     300
cgcaaaccgc ctctccccgc gcgttggccg attcattaat gcagctggca cgacaggttt     360
cccgactgga aagcgggcag tgagcgcaac gcaattaatg tgagttagct cactcattag     420
gcaccccagg ctttacactt tatgcttccg gctcgtatgt tgtgtggaat tgtgagcgga     480
taacaatttc acacaggaaa cagctatgac catgattacg ccaagctgag agacataatt     540
gtggtttgtg tttccatatt gttcatctcc cattgatcgt attaagaaag tatgatggtg     600
atgtcgcagc cttccgcttt cgcttcacgg aaaacctgaa gcacactctc ggcgccattt     660
```

```
tcagtcagct gcttgctttg ttcaaactgc ctccattcca aaacgagcgg gtactccacc    720
catccggtca gacaatccca taaagcgtcc aggttttcac cgtagtattc cggaagggca    780
agctcctttt tcaatgtctg gtggaggtcg ctgatacttc tgatttgttc cccgttaatg    840
actgcttttt tcatgtgcgg ctcctttctt atgattttat tctatcagtt taccattttt    900
ctcttcagaa atggccggat tctgccccgg tttcagctgg acgatgtcct cctgtctcgg    960
acggctgctg caaattggac cacattatgg tctctcagct tgcatgccaa acttttaatt   1020
aaggtacctg caggagcccg ggctctcgag taaaacataa ttttggcagt aaaaagtgaa   1080
ttctattgtt ttgaaaacaa aacaaaatac aggaagcgtg attgtggggt tgttgttgaa   1140
cttgcccggg caaaagaaga atgattagcg gtagaggagt tagtagttac gttcaactaa   1200
atgcgtgact aaattattta tcctccgcca tggaagcagg tgattcacac acaacttgct   1260
gcacacattg ctctcaaacc tttcctataa atatccgtag caggggctgc gatgatacac   1320
aacgcattta tcaaactac tttgattact ttctgtgggt tctactttct ttgaatagtc   1380
agttctgctg tttttagaag atttatgaga atggccaaaa ttcaggtatc aaacgggaac   1440
atggcacagg ttatcaacac gtttgacggg gttgcggatt atcttcagac atatcataag   1500
ctacctgata attacattac aaaatcagaa gcacaagccc tcggctgggt ggcatcaaaa   1560
gggaaccttg cagacgtcgc tccggggaaa agcatcggcg gagacatctt ctcaaacagg   1620
gaaggcaaac tcccgggcaa aagcggacga acatggcgtg aagcggatat taactataca   1680
tcaggcttca gaaattcaga ccggattctt tactcaagcg actggctgat ttacaaaaca   1740
acggacgagt atcagacctt tacaaaaatc agataacgaa aaaacggct tccctgcggg   1800
aggccgtttt tttcagcttt acataaagtg tgtaataaat ttttcttcaa actctgatcg   1860
gtcaagagct cttctgagag acaatacata catgtctctg atgttgtaac tttactacca   1920
aaacctataa agattggctt atttcgttct attggatatg tatcatcatt actggtaaat   1980
caagtttctt tctaataatg tagaagatca gaaaatccat aagaagatat caacatttga   2040
gttctatggt aaaattgaatt atatcaactt agttgcaatg attcattctt gactgatgca   2100
ttgatggctt atcaaaccag tttacaaaat tcgattagat agggcccatt taaatgcggc   2160
cgcttggcgc gcctgttaat tcactggccg tcgttttaca acgtcgtgac tgggaaaacc   2220
ctggcgttac ccaacttaat cgccttgcag cacatccccc tttcgccagc tggcgtaata   2280
gcgaagaggc ccgcaccgat cgcccttccc aacagttgcg cagcctgaat ggcgaatggc   2340
gcctgatgcg gtattttctc cttacgcatc tgtgcggtat ttcacaccgc atatggtgca   2400
ctctcagtac aatctgctct gatgccgcat agttaagcca gccccgacac ccgccaacac   2460
ccgctgacgc gccctgacgg gcttgtctgc tcccggcatc cgcttacaga caagctgtga   2520
ccgtctccgg gagctgcatg tgtcagaggt tttcaccgtc atcaccgaaa cgcgcgagac   2580
gaaagggcct cgtgatacgc ctatttttat aggttaatgt catgataata atggtttctt   2640
agacgtcagg tggcactttt cggggaaatg tgcgcggaac ccctatttgt ttattttct   2700
aaatacattc aaatatgtat ccgctcatga caataaacc ctgataaatg cttcaataat   2760
attgaaaaag gaagagtatg agtattcaac atttccgtgt cgcccttatt ccctttttg   2820
cggcattttg ccttcctgtt tttgctcacc cagaaacgct ggtgaaagta aaagatgctg   2880
aagatcagtt gggtgcacga gtgggttaca tcgaactgga tctcaacagc ggtaagatcc   2940
ttgagagttt tcgccccgaa gaacgttttc caatgatgag cacttttaaa gttctgctat   3000
gtggcgcggt attatcccgt attgacgccg ggcaagagca actcggtcgc cgcatacact   3060
```

```
attctcagaa tgacttggtt gagtactcac cagtcacaga aaagcatctt acggatggca    3120
tgacagtaag agaattatgc agtgctgcca taaccatgag tgataacact gcggccaact    3180
tacttctgac aacgatcgga ggaccgaagg agctaaccgc ttttttgcac aacatggggg    3240
atcatgtaac tcgccttgat cgttgggaac cggagctgaa tgaagccata ccaaacgacg    3300
agcgtgacac cacgatgcct gtagcaatgg caacaacgtt gcgcaaacta ttaactggcg    3360
aactacttac tctagcttcc cggcaacaat taatagactg gatggaggcg ataaagttg    3420 caggaccact tctgcgctcg gcccttccgg ctggctggtt tattgctgat aaatctggag    3480
ccggtgagcg tgggtctcgc ggtatcattg cagcactggg gccagatggt aagccctccc    3540
gtatcgtagt tatctacacg acggggagtc aggcaactat ggatgaacga atagacaga    3600 tcgctgagat aggtgcctca ctgattaagc attggtaact gtcagaccaa gtttactcat    3660
atatacttta gattgattta aaacttcatt tttaatttaa aaggatctag gtgaagatcc    3720
tttttgataa tctcatgacc aaaatccctt aacgtgagtt ttcgttccac tgagcgtcag    3780
accccgtaga aaagatcaaa ggatcttctt gagatccttt ttttctgcgc gtaatctgct    3840
gcttgcaaac aaaaaaacca ccgctaccag cggtggtttg tttgccggat caagagctac    3900
caactctttt tccgaaggta actggcttca gcagagcgca gataccaaat actgtccttc    3960
tagtgtagcc gtagttaggc caccacttca agaactctgt agcaccgcct acatacctcg    4020
ctctgctaat cctgttacca gtggctgctg ccagtggcga taagtcgtgt cttaccgggt    4080
tggactcaag acgatagtta ccggataagg cgcagcggtc gggctgaacg ggggggttcgt    4140 gcacacagcc cagcttggag cgaacgacct acaccgaact gagatactca cagcgtgagc    4200
tatgagaaag cgccacgctt cccgaaggga gaaaggcgga caggtatccg gtaagcggca    4260
gggtcggaac aggagagcgc acgagggag                                      4289

<210> SEQ ID NO 61
<211> LENGTH: 13383
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 61
cgccggcgtt gtggatacct cgcggaaaac ttggccctca ctgacagatg aggggcggac      60
gttgacactt gaggggccga ctcacccggc gcggcgttga cagatgaggg gcaggctcga     120
tttcggccgg cgacgtggag ctggccagcc tcgcaaatcg gcgaaaacgc ctgattttac     180
gcgagtttcc cacagatgat gtggacaagc tggggataa gtgccctgcg gtattgacac     240
tcgaggggcg cgactactga cagatgaggg gcgcgatcct tgacacttga ggggcagagt     300
gctgacagat gaggggcgca cctattgaca tttgaggggc tgtccacagg cagaaaatcc     360
agcatttgca agggtttccg cccgttttc ggccaccgct aacctgtctt ttaacctgct     420
tttaaaccaa tatttataaa ccttgttttt aaccagggct gcgccctgtg cgcgtgaccg     480
cgcacgccga aggggggtgc ccccccttct cgaaccctcc cggcccgcta acgcgggcct     540
cccatccccc caggggctgc gccctcggc gcgaacggc ctcaccccaa aaatggcagc     600
gctggcagtc cataattgtg gtccaatttg cagccgtccg agacaggagg acatcgtcca     660
gctgaaaccg gggcagaatc cggccatttc tgaagagaaa aatggtaaac tgatagaata     720
aaatcataag aaaggagccg cacatgaaaa aagcagtcat taacgggaa caaatcagaa     780
```

| | |
|---|---|
| gtatcagcga cctccaccag acattgaaaa aggagcttgc ccttccggaa tactacggtg | 840 |
| aaaacctgga cgctttatgg gattgtctga ccggatgggt ggagtacccg ctcgttttgg | 900 |
| aatggaggca gtttgaacaa agcaagcagc tgactgaaaa tggcgccgag agtgtgcttc | 960 |
| aggttttccg tgaagcgaaa gcggaaggct gcgacatcac catcatactt tcttaatacg | 1020 |
| atcaatggga gatgaacaat atggaaacac aaaccacaat tgtggtttca aaatcggctc | 1080 |
| cgtcgatact atgttatacg ccaactttga aaacaacttt gaaaaagctg ttttctggta | 1140 |
| tttaaggttt tagaatgcaa ggaacagtga attggagttc gtcttgttat aattagcttc | 1200 |
| ttggggtatc tttaaatact gtagaaaaga ggaaggaaat aataaatggc taaaatgaga | 1260 |
| atatcaccgg aattgaaaaa actgatcgaa aaataccgct gcgtaaaaga tacggaagga | 1320 |
| atgtctcctg ctaaggtata taagctggtg ggagaaaatg aaaacctata tttaaaaatg | 1380 |
| acggacagcc ggtataaagg gaccacctat gatgtggaac gggaaaagga catgatgcta | 1440 |
| tggctggaag gaaagctgcc tgttccaaag gtcctgcact ttgaacggca tgatggctgg | 1500 |
| agcaatctgc tcatgagtga ggccgatggc gtcctttgct cggaagagta tgaagatgaa | 1560 |
| caaagccctg aaaagattat cgagctgtat gcggagtgca tcaggctctt tcactccatc | 1620 |
| gacatatcgg attgtcccta tacgaatagc ttagacagcc gcttagccga attggattac | 1680 |
| ttactgaata cgatctggc cgatgtggat tgcgaaaact gggaagaaga cactccattt | 1740 |
| aaagatccgc gcgagctgta tgattttta aagacggaaa agcccgaaga ggaacttgtc | 1800 |
| ttttcccacg gcgacctggg agacagcaac atctttgtga agatggcaa agtaagtggc | 1860 |
| tttattgatc ttgggagaag cggcagggcg acaagtggt atgacattgc cttctgcgtc | 1920 |
| cggtcgatca gggaggatat cggggaagaa cagtatgtcg agctatttt tgacttactg | 1980 |
| gggatcaagc ctgattggga gaaaataaaa tattatattt tactggatga attgttttag | 2040 |
| tacctagatg tggcgcaacg atgccggcga caagcaggag cgcaccgact tcttccgcat | 2100 |
| caagtgtttt ggctctcagg ccgaggccca cggcaagtat ttgggcaagg ggtcgctggt | 2160 |
| attcgtgcag ggcaagattc ggaataccaa gtacgagaag gacggccaga cggtctacgg | 2220 |
| gaccgacttc attgccgata aggtggatta tctggacacc aaggcaccag gcgggtcaaa | 2280 |
| tcaggaataa gggcacattg ccccggcgtg agtcggggca atcccgcaag gagggtgaat | 2340 |
| gaatcggacg tttgaccgga aggcatacag gcaagaactg atcgacgcgg ggttttccgc | 2400 |
| cgaggatgcc gaaaccatcg caagccgcac cgtcatgcgt gcgccccgcg aaaccttcca | 2460 |
| gtccgtcggc tcgatggtcc agcaagctac ggccaagatc gagcgcgaca gcgtgcaact | 2520 |
| ggctcccct gccctgcccg cgccatcggc cgccgtggag cgttcgcgtc gtctcgaaca | 2580 |
| ggaggcggca ggtttggcga agtcgatgac catcgacacg cgaggaacta tgacgaccaa | 2640 |
| gaagcgaaaa accgccggcg aggacctggc aaaacaggtc agcgaggcca agcaggccgc | 2700 |
| gttgctgaaa cacacgaagc agcagatcaa ggaaatgcag ctttccttgt tcgatattgc | 2760 |
| gccgtggccg gacacgatgc gagcgatgcc aaacgacacg gcccgctctg ccctgttcac | 2820 |
| cacgcgcaac aagaaaatcc cgcgcgaggc gctgcaaaac aaggtcattt tccacgtcaa | 2880 |
| caaggacgtg aagatcacct acaccggcgt cgagctgcgg gccgacgatg acgaactggt | 2940 |
| gtggcagcag gtgttggagt acgcgaagcg cacccctatc ggcgagccga tcaccttcac | 3000 |
| gttctacgag ctttgccagg acctgggctg gtcgatcaat ggccggtatt acacgaaggc | 3060 |
| cgaggaatgc ctgtcgcgcc tacaggcgac ggcgatgggc ttcacgtccg accgcgttgg | 3120 |

```
gcacctggaa tcggtgtcgc tgctgcaccg cttccgcgtc ctggaccgtg gcaagaaaac      3180
gtcccgttgc caggtcctga tcgacgagga atcgtcgtg  ctgtttgctg gcgaccacta      3240
cacgaaattc atatgggaga agtaccgcaa gctgtcgccg acggcccgac ggatgttcga      3300
ctatttcagc tcgcaccggg agccgtaccc gctcaagctg gaaaccttcc gcctcatgtg      3360
cggatcggat tccacccgcg tgaagaagtg gcgcgagcag gtcggcgaag cctgcgaaga      3420
gttgcgagcc agcggcctgg tggaacacgc ctgggtcaat gatgacctgg tgcattgcaa      3480
acgctagggc cttgtggggt cagttccggc tggggttca  gcagccagcg ctttactggc      3540
atttcaggaa caagcgggca ctgctcgacg cacttgcttc gctcagtatc gctcgggacg      3600
cacggcgcgc tctacgaact gccgatagac aactgtcacg gttaagcgag aaatgaataa      3660
gaaggctgat aattcggatc tctgcgaggg agatgatatt tgatccggtg tgaaataccg      3720
cacagatgcg taaggagaaa ataccgcatc aggcgctctt ccgcttcctc gctcactgac      3780
tcgctgcgct cggtcgttcg gctgcggcga gcggtatcag ctcactcaaa ggcggtaata      3840
cggttatcca cagaatcagg ggataacgca ggaaagaaca tgtgagcaaa aggccagcaa      3900
aaggccagga accgtaaaaa ggccgcgttg ctggcgtttt tccataggct ccgcccccct      3960
gacgagcatc acaaaaatcg acgctcaagt cagaggtggc gaaacccgac aggactataa      4020
agataccagg cgtttccccc tggaagctcc ctcgtgcgct ctcctgttcc gaccctgccg      4080
cttaccggat acctgtccgc ctttctccct tcggaagcg  tggcgctttc tcatagctca      4140
cgctgtaggt atctcagttc ggtgtaggtc gttcgctcca agctgggctg tgtgcacgaa      4200
ccccccgttc agcccgaccg ctgcgcctta tccggtaact atcgtcttga gtccaacccg      4260
gtaagacacg acttatcgcc actggcagca gccactggta acaggattag cagagcgagg      4320
tatgtaggcg gtgctacaga gttcttgaag tggtggccta actacggcta cactagaagg      4380
acagtatttg gtatctgcgc tctgctgaag ccagttacct tcggaaaaag agttggtagc      4440
tcttgatccg gcaaacaaac caccgctggt agcggtggtt tttttgtttg caagcagcag      4500
attacgcgca gaaaaaaagg atatcaagaa gatcctttga tcttttctac ggggtctgac      4560
gctcagtgga acgaaaactc acgttaaggg attttggtca tgagattatc aaaaaggatc      4620
ttcacctaga tcctttaaa  ttaaaaatga agttttaaat caatctaaag tatatatgag      4680
taaacttggt ctgacagtta ccaatgcttc atcagtgagg ctgatcacag gcagcaacgc      4740
tctgtcatcg ttacaatcaa catgctaccc tccgcgagat catccgtgtt tcaaacccgg      4800
cagcttagtt gccgttcttc cgaatagcat cggtaacatg agcaaagtct gccgccttac      4860
aacggctctc ccgctgacgc cgtcccggac tgatgggctg cctgtatcga gtggtgattt      4920
tgtgccgagc tgccggtcgg ggagctgttg gctggctggt ggcaggatat attgtggtgt      4980
aaacaaattg acgcttagac aacttaataa cacaccgcgg tctagaacta gtggatcccc      5040
cctacgtgcg atctagtaac atagatgaca ccgcgcgcga taatttatcc tagtttgcgc      5100
gctatatttt gttttctatc gcgtattaaa tgtataattg cgggactcta atcataaaaa      5160
cccatctcat aaataacgtc atgcattaca tgttaattat tacatgctta acgtaattca      5220
acagaaatta tatgataatc atcgcaagac cggcaacagg attcaatctt aagaaacttt      5280
attgccaaat gtttgaacga tccctcagaa gaactcgtca agaaggcgat agaaggcgat      5340
gcgctgcgaa tcgggagcgg cgataccgta agcacgagg  aagcggtcag cccattcgcc      5400
gccaagctct tcagcaatat cacgggtagc caacgctatg tcctgatagc ggtccgccac      5460
acccagccgg ccacagtcga tgaatccaga aaagcggcca ttttccacca tgatattcgg      5520
```

```
caagcaggca tcgccatggg tcacgacgag atcctcgccg tcgggcatgc gcgccttgag   5580
cctggcgaac agttcggctg gcgcgagccc ctgatgctct tcgtccagat catcctgatc   5640
gacaagaccg gcttccatcc gagtacgtgc tcgctcgatg cgatgtttcg cttggtggtc   5700
gaatgggcag gtagccggat caagcgtatg cagccgccgc attgcatcag ccatgatgga   5760
tactttctcg gcaggagcaa ggtgagatga caggagatcc tgccccggca cttcgcccaa   5820
tagcagccag tcccttcccg cttcagtgac aacgtcgagc acagctgcgc aaggaacgcc   5880
cgtcgtggcc agccacgata gccgcgctgc ctcgtcctgg agttcattca gggcaccgga   5940
caggtcggtc ttgacaaaaa gaaccgggcg cccctgcgct gacagccgga acacggcggc   6000
atcagagcag ccgattgtct gttgtgccca gtcatagccg aatagcctct ccacccaagc   6060
ggccggagaa cctgcgtgca atccatcttg ttcaatcatc tgttaatcag aaaaactcag   6120
attaatcgac aaattcgatc gcacaaacta gaaactaaca ccagatctag atagaaatca   6180
caaatcgaag agtaattatt cgacaaaact caaattattt gaacaaatcg gatgatattt   6240
atgaaaccct aatcgagaat taagatgata tctaacgatc aaacccagaa atcgtcttc    6300 gatctaagat taacagaatc taaaccaaag aacatatacg aaattgggat cgaacgaaaa   6360
caaaatcgaa gattttgaga gaataaggaa cacagaaatt taccttgatc acggtagaga   6420
gaattgagag aaagttttta agattttgag aaattgaaat ctgaattgtg aagaagaaga   6480
gctctttggg tattgtttta tagaagaaga agaagaaaag acgaggacga ctaggtcacg   6540
agaaagctaa ggcggtgaag caatagctaa taataaaatg acacgtgtat tgagcgttgt   6600
ttacacgcaa agttgttttt ggctaattgc cttatttta ggttgaggaa aagtatttgt     6660
gctttgagtt gataaacacg actcgtgtgt gccggctgca accactttga cgccgtttat   6720
tactgactcg tcgacaacca caatttctaa cggtcgtcat aagatccagc cgttgagatt   6780
taacgatcgt tacgatttat attttttttag cattatcgtt ttatttttta aatatacggt   6840
ggagctgaaa attggcaata attgaaccgt gggtcccact gcattgaagc gtatttcgta   6900
ttttctagaa ttcttcgtgc tttatttctt ttcctttttg ttttttttttg ccatttatct    6960 aatgcaagtg ggcttataaa atcagtgaat ttcttggaaa agtaacttct ttatcgtata   7020
acatattgtg aaattatcca tttctttta tttttttagtg ttattggata tttttgtatg    7080
attattgatt tgcataggat aatgactttt gtatcaagtt ggtgaacaag tctcgttaaa   7140
aaaggcaagt ggtttggtga ctcgatttat tcttgttatt taattcatat atcaatggat   7200
cttatttggg gcctggtcca tatttaacac tcgtgttcag tccaatgacc aataatattt   7260
tttcattaat aacaatgtaa caagaatgat acacaaaaca ttctttgaat aagttcgcta   7320
tgaagaaggc aacttatccg gtcctagatc atcagttcat acaaacctcc atagagttca   7380
acatcttaaa caaggatatc ctgatccgtt gacggcgcgc caagcggggc cgcatttaaa   7440
tgggccctat ctaatcgaat tttgtaaact ggtttgataa gccatcaatg catcagtcaa   7500
gaatgaatca ttgcaactaa gttgatataa ttcaatttac catagaactc aaatgttgat   7560
atcttcttat ggattttctg atcttctaca ttattagaaa gaaacttgat ttaccagtaa   7620
tgatgataca tatccaatag aacgaaataa gccaatcttt ataggttttg gtagtaaagt    7680
tacaacatca gagacatgta tgtattgtct ctcagaagag ctcttgaccg atcagagttt   7740
gaagaaaaat ttattacaca ctttatgtaa agctgaaaaa aacggcctcc cgcagggaag   7800
ccgttttttt cgttatctga ttttttgtaaa ggtctgatac tcgtccgttg ttttgtaaat   7860
```

```
cagccagtcg cttgagtaaa gaatccggtc tgaatttctg aagcctgatg tatagttaat    7920
atccgcttca cgccatgttc gtccgctttt gcccgggagt ttgccttccc tgtttgagaa    7980
gatgtctccg ccgatgcttt tccccggagc gacgtctgca aggttccctt ttgatgccac    8040
ccagccgagg gcttgtgctt ctgattttgt aatgtaatta tcaggtagct tatgatatgt    8100
ctgaagataa tccgcaaccc cgtcaaacgt gttgataacc tgtgccatgt tcccgtttga    8160
tacctgaatt ttggccattc tcataaatct tctaaaaaca gcagaactga ctattcaaag    8220
aaagtagaac ccacagaaag taatcaaagt agtttgatta aatgcgttgt gtatcatcgc    8280
agcccctgct acggatattt ataggaaagg tttgagagca atgtgtgcag caagttgtgt    8340
gtgaatcacc tgcttccatg gcggaggata aataatttag tcacgcattt agttgaacgt    8400
aactactaac tcctctaccg ctaatcattc ttcttttgcc cgggcaagtt caacaacaac    8460
cccacaatca cgcttcctgt attttgtttt gttttcaaaa caatagaatt cacttttac     8520
tgccaaaatt atgttttact cgagagccca aatgcggccg caaaacccct cacaaataca    8580
taaaaaaaat tctttatttta attatcaaac tctccactac ctttcccacc aaccgttaca    8640
atcctgaatg ttggaaaaaa ctaactacat tgatataaaa aaactacatt acttcctaaa    8700
tcatatcaaa attgtataaa tatatccact caaaggagtc tagaagatcc acttggacaa    8760
attgcccata gttggaaaga tgttcaccaa gtcaacaaga tttatcaatg gaaaaatcca    8820
tctaccaaac ttactttcaa gaaaatccaa ggattataga gtaaaaaatc tatgtattat    8880
taagtcaaaa agaaaaccaa agtgaacaaa tattgatgta caagtttgag aggataagac    8940
attggaatcg tctaaccagg aggcggagga attccctaga cagttaaaag tggccggaat    9000
cccggtaaaa aagattaaaa ttttttttgta gagggagtgc ttgaatcatg tttttttatga   9060
tggaaataga ttcagcacca tcaaaaacat tcaggacacc taaaattttg aagtttaaca    9120
aaaataactt ggatctacaa aaatccgtat cggatttttct ctaaatataa ctagaatttt    9180
cataactttc aaagcaactc ctcccctaac cgtaaaactt ttcctacttc accgttaatt    9240
acattcctta agagtgataa agaaataaag taaataaaag tattcacaaa ccaacaattt    9300
atttcttttta tttacttaaa aaaacaaaaa gtttatttat tttacttaaa tggcataatg    9360
acatatcgga gatccctcga acgagaatct tttatctccc tggttttgta ttaaaaagta    9420
atttattgtg gggtccacgc ggagttggaa tcctacagac gcgctttaca tacgtctcga    9480
gaagcgtgac ggatgtgcga ccggatgacc ctgtataacc caccgacaca gccagcgcac    9540
agtatacacg tgtcatttct ctattggaaa atgtcgttgt tatccccgct ggtacgcaac    9600
caccgatggt gacaggtcgt ctgttgtcgt gtcgcgtagc gggagaaggg tctcatccaa    9660
cgctattaaa tactcgcctt caccgcgtta cttctcatct tttctcttgc gttgtataat    9720
cagtgcgata ttctcagaga ctttttcatt caaaggtatg gagttttgaa gggctttact    9780
cttaacattt gttttctttt gtaaattgtt aatggtggtt tctgtggggg aagaatcttt    9840
tgccaggtcc ttttgggttt cgcatgttta tttgggttat ttttctcgac tatggctgac    9900
attactaggg ctttcgtgct ttcatctgtg ttttcttccc ttaataggtc tgtctctctg    9960
gaatatttaa ttttcgtatg taagttatga gtagtcgctg tttgtaatag gctcttgtct   10020
gtaaaggttt cagcaggtgt ttgcgtttta ttgcgtcatg tgtttcagaa ggcctttgca   10080
gattattgcg ttgtactttta atattttgtc tccaaccttg ttatagtttc cctcctttga   10140
tctcacagga acccttttctt ctttgagcat tttcttgtgg cgttctgtag taatattta    10200
attttgggcc cgggttctga gggtaggtga ttattcacag tgatgtgctt tccctataag   10260
```

```
gtcctctatg tgtaagctgt tagggtttgt gcgttactat tgacatgtca catgtcacat    10320
attttcttcc tcttatcctt cgaactgatg gttcttttc taattcgtgg attgctggtg     10380
ccatatttta tttctattgc aactgtattt tagggtgtct ctttcttttt gatttcttgt    10440
taatatttgt gttcaggttg taactatggg ttgctagggt gtctgccctc ttcttttgtg    10500
cttctttcgc agaatctgtc cgttggtctg tatttgggtg atgaattatt tattccttga    10560
agtatctgtc taattagctt gtgatgatgt gcaggtatat tcgttagtca tatttcaatt    10620
tcaagcgatc ccccgggccc ccatggatcc agtagaaacc ccaacccgtg aaatcaaaaa    10680
actcgacggc ctgtgggcat tcagtctgga tcgcgaaaac tgtggaattg gtcagcgttg    10740
gtgggaaagc gcgttacaag aaagccggc aattgctgtg ccaggcagtt ttaacgatca     10800
gttcgccgat gcagatattc gtaattatgc gggcaacgtc tggtatcagc gcgaagtctt    10860
tataccgaaa ggttgggcag gccagcgtat cgtgctgcgt ttcgatgcgg tcactcatta    10920
cggcaaagtg tgggtcaata atcaggaagt gatggagcat cagggcggct atacgccatt    10980
tgaagccgat gtcacgccgt atgttattgc cgggaaaagt gtacgtaagt ttctgcttct    11040
acctttgata tatatataat aattatcatt aattagtagt aatataatat ttcaaatatt    11100
tttttcaaaa taaagaatg tagtatatag caattgcttt tctgtagttt ataagtgtgt     11160
atattttaat ttataacttt tctaatatat gaccaaaatt tgttgatgtg caggtatcac    11220
cgtttgtgtg aacaacgaac tgaactggca gactatcccg ccgggaatgg tgattaccga    11280
cgaaaacggc aagaaaaagc agtcttactt ccatgatttc tttaactatg ccggaatcca    11340
tcgcagcgta atgctctaca ccacgccgaa cacctgggtg gacgatatca ccgtggtgac    11400
gcatgtcgcg caagactgta accacgcgtc tgttgactgg caggtggtgg ccaatggtga    11460
tgtcagcgtt gaactgcgtg atgcggatca acaggtggtt gcaactggac aaggcactag    11520
cgggactttg caagtggtga atccgcacct ctggcaaccg ggtgaaggtt atctctatga    11580
actgtgcgtc acagccaaaa gccagacaga gtgtgatatc tacccgcttc gcgtcggcat    11640
ccggtcagtg gcagtgaagg cgaacagtt cctgattaac cacaaaccgt tctactttac     11700
tggctttggt cgtcatgaag atgcggactt gcgtggcaaa ggattcgata acgtgctgat    11760
ggtgcacgac cacgcattaa tggactggat tggggccaac tcctaccgta cctcgcatta    11820
cccttacgct gaagagatgc tcgactgggc agatgaacat ggcatcgtgg tgattgatga    11880
aactgctgct gtcggcttta acctctcttt aggcattggt ttcgaagcgg caacaagcc     11940 gaaagaactg tacagcgaag aggcagtcaa cggggaaact cagcaagcgc acttacaggc    12000
gattaaagag ctgatagcgc gtgacaaaaa ccacccaagc gtggtgatgt ggagtattgc    12060
caacgaaccg gataccgtc gcaaggtgc acgggaatat tcgcgccac tggcggaagc       12120 aacgcgtaaa ctcgacccga cgcgtccgat cacctgcgtc aatgtaatgt tctgcgacgc    12180
tcacaccgat accatcagcg atctctttga tgtgctgtgc ctgaaccgtt attacgatg     12240 gtatgtccaa agcggcgatt tggaaacggc agagaaggta ctggaaaaag aacttctggc    12300
ctggcaggag aaactgcatc agccgattat catcaccgaa tacggcgtgg atacgttagc    12360
cgggctgcac tcaatgtaca ccgacatgtg gagtgaagag tatcagtgtg catggctgga    12420
tatgtatcac cgcgtctttg atcgcgtcag cgccgtcgtc ggtgaacagg tatggaattt    12480
cgccgatttt gcgacctcgc aaggcatatt gcgcgttggc ggtaacaaga aagggatctt    12540
cactcgcgac cgcaaaccga gtcggcggc ttttctgctg caaaaacgct ggactggcat     12600
```

```
gaacttcggt gaaaaaccgc agcagggagg caaacaatga atcaacaact ctcctggcgc   12660
accatcgtcg gctacagcct cgggaattgc taccggggtt cgaaatcgat gggtgttatt   12720
tgtggataat aaattcgggt gatgttcagt gtttgtcgta tttctcacga ataaattgtg   12780
tttatgtatg tgttagtgtt gtttgtctgt ttcagaccct cttatgttat attttctttt   12840
tcgtcggtca gttgaagcca atactggtgt cctggccggc actgcaatac catttcgttt   12900
aatataaaga ctctgttatc cgtgagctcg aatttccccg atcgttcaaa catttggcaa   12960
taaagtttct taagattgaa tcctgttgcc ggtcttgcga tgattatcat ataatttctg   13020
ttgaattacg ttaagcatgt aataattaac atgtaatgca tgacgttatt tatgagatgg   13080
gtttttatga ttagagtccc gcaattatac atttaatacg cgatagaaaa caaaatatag   13140
cgcgcaaact aggataaatt atcgcgcgcg gtgtcatcta tgttactaga tcgcggccgc   13200
atttgggctc ctgcaggtac cttaattaaa agtttaaact atcagtgttt gacaggatat   13260
attggcgggt aaacctaaga gaaaagagcg tttattagaa taatcggata tttaaaaggg   13320
cgtgaaaagg tttatccgtt cgtccatttg tatgtgcatg ccaaccacag ggttccccag   13380
atc                                                                13383

<210> SEQ ID NO 62
<211> LENGTH: 11300
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 62
cgccggcgtt gtggatacct cgcggaaaac ttggccctca ctgacagatg aggggcggac     60
gttgacactt gaggggccga ctcacccggc gcggcgttga cagatgaggg gcaggctcga    120
tttcggccgg cgacgtggag ctggccagcc tcgcaaatcg gcgaaaacgc ctgattttac    180
gcgagtttcc cacagatgat gtggacaagc ctggggataa gtgccctgcg gtattgacac    240
ttgaggggcg cgactactga cagatgaggg gcgcgatcct tgacacttga ggggcagagt    300
gctgacagat gaggggcgca cctattgaca tttgaggggc tgtccacagg cagaaaatcc    360
agcatttgca agggtttccg cccgtttttc ggccaccgct aacctgtctt ttaacctgct    420
tttaaaccaa tatttataaa ccttgttttt aaccagggct gcgccctgtg cgcgtgaccg    480
cgcacgccga aggggggtgc cccccttct cgaaccctcc cggcccgcta acgcgggcct    540
cccatccccc caggggctgc gcccctcggc cgcgaacggc ctcaccccaa aaatggcagc    600
gctggcagtc cataattgtg ggctgagaga cataattgtg gtttgtgttt ccatattgtt    660
catctcccat tgatcgtatt aagaaagtat gatggtgatg tcgcagcctt ccgctttcgc    720
ttcacggaaa acctgaagca cactctcggc gccattttca gtcagctgct tgctttgttc    780
aaactgcctc cattccaaaa cgagcgggta ctccacccat ccggtcagac aatcccataa    840
agcgtccagg ttttcaccgt agtattccgg aagggcaagc tccttttca atgtctggtg    900 gaggtcgctg atacttctga tttgttcccc gttaatgact gctttttca tgtgcggctc    960 ctttcttatg attttattct atcagttac cattttctc ttcagaaatg gccggattct    1020
gcccgggttt cagctggacg atgtcctcct gtctcggacg gctgctgcaa attggaccac   1080
attatggtct ctcccataat tgtggtttca aaatcggctc cgtcgatact atgttatacg   1140
ccaactttga aaacaacttt gaaaaagctg ttttctggta tttaaggttt tagaatgcaa   1200
```

```
ggaacagtga attggagttc gtcttgttat aattagcttc ttggggtatc tttaaatact    1260
gtagaaaaga ggaaggaaat aataaatggc taaaatgaga atatcaccgg aattgaaaaa    1320
actgatcgaa aaataccgct gcgtaaaaga tacggaagga atgtctcctg ctaaggtata    1380
taagctggtg ggagaaaatg aaaacctata tttaaaaatg acggacagcc ggtataaagg    1440
gaccacctat gatgtggaac gggaaaagga catgatgcta tggctggaag aaagctgcc    1500 tgttccaaag gtcctgcact ttgaacggca tgatggctgg agcaatctgc tcatgagtga    1560
ggccgatggc gtcctttgct cggaagagta tgaagatgaa caaagccctg aaaagattat    1620
cgagctgtat gcggagtgca tcaggctctt tcactccatc gacatatcgg attgtcccta    1680
tacgaatagc ttagacagcc gcttagccga attggattac ttactgaata acgatctggc    1740
cgatgtggat tgcgaaaact gggaagaaga cactccattt aaagatccgc gcgagctgta    1800
tgatttttta aagacggaaa agcccgaaga ggaacttgtc ttttcccacg gcgacctggg    1860
agacagcaac atctttgtga agatggcaa agtaagtggc tttattgatc ttgggagaag    1920
cggcagggcg gacaagtggt atgacattgc cttctgcgtc cggtcgatca gggaggatat    1980
cggggaagaa cagtatgtcg agctattttt tgacttactg ggatcaagc ctgattggga    2040 gaaaataaaa tattatattt tactggatga attgttttag tacctagatg tggcgcaacg    2100
atgccggcga caagcaggag cgcaccgact tcttccgcat caagtgtttt ggctctcagg    2160
ccgaggccca cggcaagtat ttgggcaagg ggtcgctggt attcgtgcag ggcaagattc    2220
ggaataccaa gtacgagaag gacggccaga cggtctacgg gaccgacttc attgccgata    2280
aggtggatta tctggacacc aaggcaccag gcgggtcaaa tcaggaataa gggcacattg    2340
ccccggcgtg agtcggggca atcccgcaag gagggtgaat gaatcggacg tttgaccgga    2400
aggcatacag gcaagaactg atcgacgcgg ggttttccgc cgaggatgcc gaaaccatcg    2460
caagccgcac cgtcatgcgt gcgccccgcg aaaccttcca gtccgtcggc tcgatggtcc    2520
agcaagctac ggccaagatc gagcgcgaca gcgtgcaact ggctccccct gccctgcccg    2580
cgccatcggc cgccgtggag cgttcgcgtc gtctcgaaca ggaggcggca ggtttggcga    2640
agtcgatgac catcgacacg cgaggaacta tgacgaccaa gaagcgaaaa accgccggcg    2700
aggacctggc aaaacaggtc agcgaggcca agcaggccgc gttgctgaaa cacacgaagc    2760
agcagatcaa ggaaatgcag cttttccttgt tcgatattgc gccgtggccg gacacgatgc    2820
gagcgatgcc aaacgacacg gcccgctctg ccctgttcac cacgcgcaac aagaaaatcc    2880
cgcgcgaggc gctgcaaaac aaggtcattt tccacgtcaa caaggacgtg aagatcacct    2940
acaccggcgt cgagctgcgg gccgacgatg acgaactggt gtggcagcag gtgttggagt    3000
acgcgaagcg caccccctatc ggcgagccga tcaccttcac gttctacgag ctttgccagg    3060
acctgggctg gtcgatcaat ggccggtatt acacgaaggc cgaggaatgc ctgtcgcgcc    3120
tacaggcgac ggcgatgggc ttcacgtccg accgcgttgg gcacctggaa tcggtgtcgc    3180
tgctgcaccg cttccgcgtc ctggaccgtg caagaaaac gtcccgttgc caggtcctga    3240
tcgacgagga aatcgtcgtg ctgtttgctg gcgaccacta cacgaaattc atatgggaga    3300
agtaccgcaa gctgtcgccg acggcccgac ggatgttcga ctatttcagc tcgcaccggg    3360
agccgtaccc gctcaagctg gaaaccttcc gcctcatgtg cggatcggat tccacccgcg    3420
tgaagaagtg gcgcgagcag gtcggcgaag cctgcgaaga gttgcgaggc agcggcctgg    3480
tggaacacgc ctgggtcaat gatgacctgg tgcattgcaa acgctagggc cttgtgggg   3540 cagttccggc tgggggttca gcagccagcg ctttactggc atttcaggaa caagcgggca    3600
```

```
ctgctcgacg cacttgcttc gctcagtatc gctcggacg cacgcgcgc tctacgaact    3660
gccgatagac aactgtcacg gttaagcgag aaatgaataa gaaggctgat aattcggatc    3720
tctgcgaggg agatgatatt tgatcacagg cagcaacgct ctgtcatcgt tacaatcaac    3780
atgctaccct ccgcgagatc atccgtgttt caaacccggc agcttagttg ccgttcttcc    3840
gaatagcatc ggtaacatga gcaaagtctg ccgccttaca acggctctcc cgctgacgcc    3900
gtcccggact gatgggctgc ctgtatcgag tggtgatttt gtgccgagct gccggtcggg    3960
gagctgttgg ctggctggtg gcaggatata ttgtggtgta aacaaattga cgcttagaca    4020
acttaataac acattgcgga cgttttaat gtactgggt ggttttctt ttcaccagtg    4080
agacgggcaa cagctgattg cccttcaccg cctggccctg agagagttgc agcaagcggt    4140
ccacgctggt ttgccccagc aggcgaaaat cctgtttgat ggtggttccg aaatcggcaa    4200
aatcccttat aaatcaaaag aatagcccga gatagggttg agtgttgttc cagtttggaa    4260
caagagtcca ctattaaaga acgtggactc caacgtcaaa gggcgaaaaa ccgtctatca    4320
gggcgatggc ccacggccgc tctagaacta gtggatccac cagaaccacc accagagccg    4380
ccgccagcat tgacaggagg cccgatctag taacatagat gacaccgcgc gcgataattt    4440
atcctagttt gcgcgctata ttttgttttc tatcgcgtat taaatgtata attgcgggac    4500
tctaatcata aaacccatc tcataaataa cgtcatgcat tacatgttaa ttattacatg    4560
cttaacgtaa ttcaacagaa attatatgat aatcatcgca agaccggcaa caggattcaa    4620
tcttaagaaa cttattgcc aaatgtttga acgatcgggg atcatccggg tctgtggcgg    4680
gaactccacg aaaatatccg aacgcagcaa gatatcgcgg tgcatctcgg tcttgcctgg    4740
gcagtcgccg ccgacgccgt tgatgtggac gccgggccg atcatattgt cgctcaggat    4800
cgtggcgttg tgcttgtcgg ccgttgctgt cgtaatgata tcggcacctt cgaccgcctg    4860
ttccgcagag atcccgtggg cgaagaactc cagcatgaga tccccgcgct ggaggatcat    4920
ccagccggcg tcccggaaaa cgattccgaa gcccaacctt tcatagaagg cggcggtgga    4980
atcgaaatct cgtgatggca ggttgggcgt cgcttggtcg tcatttcga accccagagt    5040
cccgctcaga agaactcgtc aagaaggcga tagaaggcga tgcgctgcga atcgggagcg    5100
gcgataccgt aaagcacgag gaagcggtca gcccattcgc cgccaagctc ttcagcaata    5160
tcacgggtag ccaacgctat gtcctgatag cggtccgcca cacccagccg ccacagtcg    5220
atgaatccag aaaagcggcc attttccacc atgatattcg gcaagcaggc atcgccatgg    5280
gtcacgacga gatcatcgcc gtcgggcatg cgcgccttga gcctggcgaa cagttcggct    5340
ggcgcgagcc cctgatgctc ttcgtccaga tcatcctgat cgacaagacc ggcttccatc    5400
cgagtacgtg ctcgctcgat gcgatgtttc gcttggtggt cgaatgggca ggtagccgga    5460
tcaagcgtat gcagccgccg cattgcatca gccatgatgg atactttctc ggcaggagca    5520
aggtgagatg acaggagatc ctgccccggc acttcgccca atagcagcca gtcccttccc    5580
gcttcagtga acgtcgag cacagctgcg caaggaacgc ccgtcgtggc cagccacgat    5640
agccgcgctg cctcgtcctg cagttcattc agggcaccgg acaggtcggt cttgacaaaa    5700
agaaccgggc gcccctgcgc tgacagccgg aacacgcgg catcagagca gccgattgtc    5760
tgttgtgccc agtcatagcc gaatagcctc tccacccaag cggccggaga acctgcgtgc    5820
aatccatctt gttcaatcat gcgaaacgat ccagatccgg tgcagattat ttggattgag    5880
agtgaatatg agactctaat tggataccga ggggaattta tggaacgtca gtggagcatt    5940
```

```
tttgacaaga aatatttgct agctgatagt gaccttaggc gacttttgaa cgcgcaataa    6000
tggtttctga cgtatgtgct tagctcatta aactccagaa acccgcggct gagtggctcc    6060
ttcaacgttg cggttctgtc agttccaaac gtaaaacggc ttgtcccgcg tcatcggcgg    6120
gggtcataac gtgactccct taattctccg ctcatgatca gattgtcgtt tcccgccttc    6180
agtttaaact atcagtgttg cggccgcggc gcgccttccc gatctagtaa catagatgac    6240
accgcgcgcg ataatttatc ctagtttgcg cgctatattt tgttttctat cgcgtattaa    6300
atgtataatt gcgggactct aatcataaaa acccatctca taaataacgt catgcattac    6360
atgttaatta ttacatgctt aacgtaattc aacagaaatt atatgataat catcgcaaga    6420
ccggcaacag gattcaatct taagaaactt tattgccaaa tgtttgaacg atcggggaaa    6480
ttcgagctca aagtgcaatt gaccgatcag agtttgaaga aaaatttatt acacacttta    6540
tgtaaagctg aaaaaaacgg cctcccgcag ggaagccgtt ttttcgtta tctgattttt    6600
gtagaggtct gataatggtc cgttgttttg taaatcagcc agtcgcttga gtaaagaatc    6660
cggtctgaat ttctgaagcc tgatgtatag ttaatatccg cttcacgcca tgttcgtccg    6720
cttttgcccg ggagtttgcc ttccctgttt gagaagatgt ctccgccgat gcttttcccc    6780
ggagcgacgt ctgcaaggtt ccctttgat gccacccagc cgagggcttg tgcttctgat    6840
tttgtaatgt aattatcagg tagcttatga tatgtctgaa gataatccgc aaccccgtca    6900
aacgtgttga taacctgtgc catgatttgt acacaaaatt tccgcgcaca gatcctcaca    6960
gcgtatgcaa aacaaagctg caactactaa taccagtcca aaagcaatgg gcgcaacagc    7020
aacagcaaaa gctgcaaccc cttgtgctgg ttcgttccta cagttggacg cagcccgagt    7080
tctgagaaac aaataaccac aaggcaagtt aggtaccaaa ccccttaagc tcaacttaag    7140
caaatattac aatcgtttgt ttctacaaac aaatctttt cagaacggct tcaggtgggg    7200
aatattgtcc atttaagtac ctgaaaatct aagaacacgg ccaatccggg cgcctttgct    7260
tgaaagtggg aagaaacctg aatgattgaa cagtggataa gagatttata agcaagatta    7320
gcagggctga tcagattgtt ttttcgggta ggttgatcaa tacatatgcc ccttccctct    7380
tcctttcctc tacaatcgat tgccaggaag agatagagat accatcatga tgatgatggt    7440
ggggatggcg atgatggtaa tgatgatgat ccagcagaaa aaattgcgca gaagaagaag    7500
atgagcggtc ggtcggtcga tagcctttca gtcggagggg aaagaacaaa ataatgccta    7560
tttgaaggca gatggattga ctaagacgtg tgcaggcagt ggaggagtta caaggcagga    7620
catatttact aggtataggt gtaggtaata gtaatggaga ggataaattt aggttttggg    7680
atgaatggat ttgttggtac atgttgcaac tcccacactg caatcaaagg accgctatga    7740
cacccctga atgcgacgcc catgagaatg ccgaccccac atatacattt ctggaaataa    7800
tagggaaatg caccttgca ttatatttca tttattcgtc ctccattttg tgcgctctcc    7860
attcattttc aaatgcgctc cactcttcct ttatttctta ccaccattat ctcgtattcg    7920
aggtccagaa atcaagttgt gaatctgcct tggttgcgca ttgttaaagt actcttctgt    7980
gtatatttct gccccaccgt tttcacttcc aacacttaaa ttttttatt ttttattta    8040
tatatttctt ataaattgtt ggcttctcac acgaacccaa gccatccaag ccccgacaaa    8100
ggcaatccaa tgtacttgac tagagtcaaa tacctttac ttctttactt ctcatattac    8160
ccagaagcca agccaacctt accaaactaa tgtacctgag cagagtccac tacctttcct    8220
caagtacagt ggcagtcaga gtatatcacc gcttgttatg tatatgcttt aatgctatgc    8280
ttatttctag gtcataatct aaatcatatt tgctgtcgag tttaagctta tcgataccgt    8340
```

```
cgacctcgag cttcttcttg aatgctctta tgggtaggat tattttttcac ttttttcctt    8400
catattccac acacatatat atataaacac actaacatta gtgggaatat tgtttgata     8460
tgtttatttt atttacttcg ggggttttg taacaatttt gtagatctaa tttcttgtct    8520
tcatgtgtat attaatttc ccttaagact taaataaaaa gagagagttt gttatatata    8580
gatatatgaa gtgagggaaa tggtacaaag ttaaggaga tctgagtgag agttagataa    8640
taaatgaaaa gaaataagaa accatcaggg ttttttctaa tgtggagttt tagattcagt   8700
tttgtagaac taagattcac tttgttgggt gttctttctt cactcatttc tgttattata   8760
ataataataa aatcttatat ctttctattt tccttactaa caagtacttg aagatttaga   8820
tatatttata gatctggtgt tgtaataggt aaaaacttga ttttatgac tataaaagta    8880
agttttggga aacaaattgg ggagagagta aggaaggact atgaggtcat atcttctgtt   8940
ttgtgatcat ccatcctcca ttgttgttaa tgtctgtgtc tctctttttc ttctcttctt   9000
tctcttactt tccttctta tctctagctc tctttctctc tcatgaatta tatcatatca    9060
tatatttgat acaaacacat gtgatggtaa gtgagagtga ataaggtgaa actagctaga   9120
tttttgagtt ttcatgaaat tttaacttat atgagtgata gaaataatg gaacttatac    9180
gtacatgtag gacaatttag atggttatct aagttttgt ttttgttttc tcttgagaat    9240
gttaaatgtt agtgttattt ttgtagtttt ggaaaattat atatgagcta agattagttt   9300
agaagtggtc aaaagaaaca tagatttgaa atttcaactg aattttcaag atttcaaata   9360
gtcaatgaaa caaggaggta attaagacaa attagcttat ggggactctt ttttgttatt   9420
ccttaaaatt actctttta aaattaaaaa taactaatct catttcgaac tacattactc    9480
aaactagtaa tctctaattc gacacgcaat ttccaaatac ttattagtag agagtcccac   9540
gtgattactt tcttctccac caaaacataa aacatgtcaa gattaaatgg tgtttgaaaa   9600
ttaaagatc aatttttctta atcgtttaca gttgtcaact ctcatgtcct gaaatatata   9660
attctcatgt ccaaaacaag aaaagctaac aacgacttca aattaaatca gtcaatcaaa   9720
attagtcttc atttacctac taatttcttt ttatatatcc gatgggtact ctacgaaatc   9780
agagtttcgt ttcttatt atttttcttt ataagatttt tgaggttttt tcagaggttg     9840
gaattgagcg caagattagg ttttgggtct gtaagatttg ttgtctttgt taaagaatct   9900
ttgatcacgt catcactcag atattattc ttttttattt tcatttgtat ttttactaat    9960
ttattataaa gttttgttag tttcagttct tgacttctga caagaaggtt ttatgtcata  10020
atgaattaat ttgtaaccta tttataaatt caaaaatgtc atcatattac tacttttgac  10080
catttaatat tagatttctc atttggtcaa tacccaatgt tcatattaca tatatagaga  10140
caaaaattat aaggatacta aattgttcat atttcttgga agtaaaaaga ttaatgatca  10200
ctgaataaat agatttggca tagaagtata gcattggaat tgcttcaaca tctttggtgt  10260
agatagattt atgcaatttc tctttctttt tgaagtatct tttttttttct agagagagaa  10320
taatgttagg gatttttatc attttctctc tcattatggg tactgagagg aaagtgagat  10380
ttttagtacg gatccaatag tttaagagtt tggtctgcct tctacgatcc aaaaaaatct  10440
acggtcatga tctctccatc gagaaggttg agagttcaga catcaaagtc tataatatgt  10500
cattgtaata cgtatttgtg catatatatc tatgtacaag tacatataca ggaaactcaa  10560
gaaaaaagaa taaatggtaa atttaattat attccaaata aggaaagtat ggaacgttgt  10620
gatgttactc ggacaagtca tttagttaca tccatcacgt ttaaatttaa tccaatggtt  10680
```

-continued

```
acaattttaa tactatcaaa tgtctattgg atttataccc aatgtgttaa tgggttgttg    10740
acacatgtca catgtctgaa accctagaca tgttcagacc aatcatgtca ctctaatttt    10800
gccagcatgg cagttggcag ccaatcacta gctcgataaa tttaaggttt cagaggaatt    10860
ttaatttatt tagggttcat attgtttcat aaaatgattc tttatttgtt acaactttaa    10920
ggaaatattt tattaactat ttaattgttc ccttttctta tattacttt gttttttctt      10980 cacatcatgt gtcacattaa gttgcatttc ttctgactca aaagaaccga tgtttgcttt    11040
taaggtttcg tattagaatc acttaactgt gcaagtggtc gatttgaccc tatcaagctt    11100
gatatcgaat tcctgcagcc cgggctcctg caggtacctt aattaaaagt ttaaactatc    11160
agtgtttgac aggatatatt ggcgggtaaa cctaagagaa aagagcgttt attagaataa    11220
tcggatattt aaaagggcgt gaaaaggttt atccgttcgt ccatttgtat gtgcatgcca    11280
accacagggt tccccagatc                                                11300
```

<210> SEQ ID NO 63
<211> LENGTH: 12509
<212> TYPE: DNA
<213> ORGANISM: Artificial Sequence
<220> FEATURE:
<223> OTHER INFORMATION: Description of Artificial Sequence: Synthetic oligonucleotide construct

<400> SEQUENCE: 63

```
cgccggcgtt gtggatacct cgcggaaaac ttggccctca ctgacagatg aggggcggac      60
gttgacactt gaggggccga ctcacccggc gcggcgttga cagatgaggg gcaggctcga    120
tttcggccgg cgacgtggag ctggccagcc tcgcaaatcg gcgaaaacgc ctgattttac    180
gcgagtttcc cacagatgat gtggacaagc ctggggataa gtgccctgcg gtattgacac    240
ttgaggggcg cgactactga cagatgaggg gcgcgatcct tgacacttga ggggcagagt    300
gctgacagat gaggggcgca cctattgaca tttgaggggc tgtccacagg cagaaaatcc    360
agcatttgca agggtttccg cccgtttttc ggccaccgct aacctgtctt ttaacctgct    420
tttaaaccaa tatttataaa ccttgttttt aaccagggct gcgccctgtg cgcgtgaccg    480
cgcacgccga agggggtgc cccccttct cgaaccctcc cggcccgcta acgcgggcct      540
cccatccccc caggggctgc gcccctcggc cgcgaacggc ctcacccaa aaatggcagc      600 gctggcagtc cataattgtg gtccaatttg cagccgtccg agacaggagg acatcgtcca    660
gctgaaaccg ggcagaatc cggccatttc tgaagagaaa aatggtaaac tgatagaata    720
aaatcataag aaaggagccg cacatgaaaa agcagtcat taacggggaa caaatcagaa    780
gtatcagcga cctccaccag acattgaaaa aggagcttgc ccttccggaa tactacggtg    840
aaaacctgga cgctttatgg gattgtctga ccggatgggt ggagtacccg ctcgttttgg    900
aatggaggca gtttgaacaa agcaagcagc tgactgaaaa tggcgccgag agtgtgcttc    960
aggttttccg tgaagcgaaa gcggaaggct gcgacatcac catcatactt tcttaatacg    1020
atcaatggga gatgaacaat atggaaacac aaaccacaat tgtggtttca aaatcggctc    1080
cgtcgatact atgttatacg ccaactttga aaacaacttt gaaaagctg tttctggta     1140 tttaaggttt tagaatgcaa ggaacagtga attggagttc gtcttgttat aattagcttc    1200
ttggggtatc tttaaatact gtagaaaaga ggaaggaaat aataaatggc taaaatgaga    1260
atatcaccgg aattgaaaaa actgatcgaa aaataccgct gcgtaaaaga tacgaagga    1320 atgtctcctg ctaaggtata taagctggtg ggagaaaatg aaaacctata tttaaaaatg    1380
```

```
acggacagcc ggtataaagg gaccacctat gatgtggaac gggaaaagga catgatgcta      1440
tggctggaag gaaagctgcc tgttccaaag gtcctgcact ttgaacggca tgatggctgg      1500
agcaatctgc tcatgagtga ggccgatggc gtcctttgct cggaagagta tgaagatgaa      1560
caaagccctg aaaagattat cgagctgtat gcggagtgca tcaggctctt tcactccatc      1620
gacatatcgg attgtcccta tacgaatagc ttagacagcc gcttagccga attggattac      1680
ttactgaata cgatctggc cgatgtggat tgcgaaaact gggaagaaga cactccattt       1740
aaagatccgc gcgagctgta tgatttttta aagacggaaa agcccgaaga ggaacttgtc      1800
ttttcccacg gcgacctggg agacagcaac atctttgtga agatggcaa agtaagtggc       1860 tttattgatc ttgggagaag cggcagggcg acaagtggt atgacattgc cttctgcgtc       1920
cggtcgatca ggaggatat cggggaagaa cagtatgtcg agctattttt tgacttactg       1980
gggatcaagc ctgattggga gaaaataaaa tattatattt tactggatga attgttttag      2040
tacctagatg tggcgcaacg atgccggcga caagcaggag cgcaccgact tcttccgcat      2100
caagtgtttt ggctctcagg ccgaggccca cggcaagtat ttgggcaagg ggtcgctggt      2160
attcgtgcag ggcaagattc ggaataccaa gtacgagaag gacggccaga cggtctacgg      2220
gaccgacttc attgccgata aggtggatta tctggacacc aaggcaccag gcgggtcaaa      2280
tcaggaataa gggcacattg ccccggcgtg agtcggggca atcccgcaag gagggtgaat      2340
gaatcggacg tttgaccgga aggcatacag gcaagaactg atcgacgcgg ggttttccgc      2400
cgaggatgcc gaaaccatcg caagccgcac cgtcatgcgt gcgccccgcg aaaccttcca      2460
gtccgtcggc tcgatggtcc agcaagctac ggccaagatc gagcgcgaca gcgtgcaact      2520 ggctcccct gccctgcccg cgccatcggc cgccgtggag cgttcgcgtc gtctcgaaca       2580
ggaggcggca ggtttggcga agtcgatgac catcgcacg cgaggaacta tgacgaccaa       2640
gaagcgaaaa accgccggcg aggacctggc aaaacaggtc agcgaggcca agcaggccgc      2700
gttgctgaaa cacacgaagc agcagatcaa ggaaatgcag cttttccttgt tcgatattgc      2760 gccgtggccg gacacgatgc gagcgatgcc aaacgacacg gcccgctctg ccctgttcac      2820
cacgcgcaac aagaaaatcc gcgcgcgagg gctgcaaaac aaggtcattt tccacgtcaa      2880
caaggacgtg aagatcacct acaccggcgt cgagctgcgg gccgacgatg acgaactggt      2940
gtggcagcag gtgttggagt acgcgaagcg caccccctatc ggcgagccga tcaccttcac      3000
gttctacgag ctttgccagg acctgggctg gtcgatcaat ggccggtatt acacgaaggc      3060
cgaggaatgc ctgtcgcgcc tacaggcgac ggcgatgggc ttcacgtccg accgcgttgg      3120
gcacctggaa tcggtgtcgc tgctgcaccg cttccgcgtc ctggaccgtg gcaagaaaac      3180
gtcccgttgc caggtcctga tcgacgagga atcgtcgtg ctgtttgctg gcgaccacta       3240
cacgaaattc atatgggaga agtaccgcaa gctgtcgccg acggcccgac ggatgttcga      3300
ctatttcagc tcgcaccggg agccgtaccc gctcaagctg gaaaccttcc gcctcatgtg      3360
cggatcggat tccacccgcg tgaagaagtg gcgcgagcag gtcggcgaag cctgcgaaga      3420
gttgcgaggc agcggcctgg tggaacacgc ctgggtcaat gatgacctgg tgcattgcaa      3480
acgctagggc cttgtgggt cagttccggc tgggggttca gcagccagcg ctttactggc       3540
atttcaggaa caagcgggca ctgctcgacg cacttgcttc gctcagtatc gctcgggacg      3600
cacggcgcgc tctacgaact gccgatagac aactgtcacg gttaagcgag aaatgaataa      3660
gaaggctgat aattcggatc tctgcgaggg agatgatatt tgatccggtg tgaaataccg      3720
cacagatgcg taaggagaaa ataccgcatc aggcgctctt ccgcttcctc gctcactgac      3780
```

```
tcgctgcgct cggtcgttcg gctgcggcga gcggtatcag ctcactcaaa ggcggtaata   3840
cggttatcca cagaatcagg ggataacgca ggaaagaaca tgtgagcaaa aggccagcaa   3900
aaggccagga accgtaaaaa ggccgcgttg ctggcgtttt tccataggct ccgcccccct   3960
gacgagcatc acaaaaatcg acgctcaagt cagaggtggc gaaacccgac aggactataa   4020
agataccagg cgtttccccc tggaagctcc ctcgtgcgct ctcctgttcc gaccctgccg   4080
cttaccggat acctgtccgc ctttctccct tcgggaagcg tggcgctttc tcatagctca   4140
cgctgtaggt atctcagttc ggtgtaggtc gttcgctcca agctgggctg tgtgcacgaa   4200
ccccccgttc agcccgaccg ctgcgcctta tccggtaact atcgtcttga gtccaacccg   4260
gtaagacacg acttatcgcc actggcagca gccactggta acaggattag cagagcgagg   4320
tatgtaggcg gtgctacaga gttcttgaag tggtggccta actacggcta cactagaagg   4380
acagtatttg gtatctgcgc tctgctgaag ccagttacct tcggaaaaag agttggtagc   4440
tcttgatccg gcaaacaaac caccgctggt agcggtggtt tttttgtttg caagcagcag   4500
attacgcgca gaaaaaaagg atatcaagaa gatcctttga tcttttctac ggggtctgac   4560
gctcagtgga acgaaaactc acgttaaggg attttggtca tgagattatc aaaaaggatc   4620
ttcacctaga tccttttaaa ttaaaaatga agttttaaat caatctaaag tatatatgag   4680
taaacttggt ctgacagtta ccaatgcttc atcagtgagg ctgatcacag gcagcaacgc   4740
tctgtcatcg ttacaatcaa catgctaccc tccgcgagat catccgtgtt tcaaacccgg   4800
cagcttagtt gccgttcttc cgaatagcat cggtaacatg agcaaagtct gccgccttac   4860
aacggctctc ccgctgacgc cgtcccggac tgatgggctg cctgtatcga gtggtgattt   4920
tgtgccgagc tgccggtcgg ggagctgttg gctggctggt ggcaggatat attgtggtgt   4980
aaacaaattg acgcttagac aacttaataa cacaccgcgg tctagaacta gtggatcccc   5040
cctacgtgcg atctagtaac atagatgaca ccgcgcgcga taatttatcc tagtttgcgc   5100
gctatatttt gttttctatc gcgtattaaa tgtataattg cgggactcta atcataaaaa   5160
cccatctcat aaataacgtc atgcattaca tgttaattat tacatgctta acgtaattca   5220 acagaaaatta tatgataatc atcgcaagac cggcaacagg attcaatctt aagaaacttt   5280
attgccaaat gtttgaacga tccctcagaa gaactcgtca agaaggcgat agaaggcgat   5340
gcgctgcgaa tcgggagcgg cgataccgta agcacgagg aagcggtcag cccattcgcc   5400
gccaagctct tcagcaatat cacgggtagc caacgctatg tcctgatagc ggtccgccac   5460
acccagccgg ccacagtcga tgaatccaga aaagcggcca ttttccacca tgatattcgg   5520
caagcaggca tcgccatggg tcacgacgag atcctcgccg tcgggcatgc gcgccttgag   5580
cctggcgaac agttcggctg gcgcgagccc ctgatgctct tcgtccagat catcctgatc   5640
gacaagaccg gcttccatcc gagtacgtgc tcgctcgatg cgatgtttcg cttggtggtc   5700
gaatgggcag gtagccggat caagcgtatg cagccgccgc attgcatcag ccatgatgga   5760
tactttctcg gcaggagcaa ggtgagatga caggagatcc tgccccggca cttcgcccaa   5820
tagcagccag tcccttcccg cttcagtgac aacgtcgagc acagctgcgc aaggaacgcc   5880
cgtcgtggcc agccacgata gccgcgctgc ctcgtcctgg agttcattca gggcaccgga   5940
caggtcggtc ttgacaaaaa gaaccgggcg cccctgcgct gacagccgga acacggcggc   6000
atcagagcag ccgattgtct gttgtgccca gtcatagccg aatagcctct ccacccaagc   6060
ggccggagaa cctgcgtgca atccatcttg ttcaatcatc tgttaatcag aaaaactcag   6120
```

```
attaatcgac aaattcgatc gcacaaacta gaaactaaca ccagatctag atagaaatca    6180
caaatcgaag agtaattatt cgacaaaact caaattattt gaacaaatcg gatgatattt    6240
atgaaaccct aatcgagaat taagatgata tctaacgatc aaacccagaa aatcgtcttc    6300
gatctaagat taacagaatc taaaccaaag aacatatacg aaattgggat cgaacgaaaa    6360
caaaatcgaa gattttgaga gaataaggaa cacagaaatt taccttgatc acggtagaga    6420
gaattgagag aaagttttta agattttgag aaattgaaat ctgaattgtg aagaagaaga    6480
gctctttggg tattgtttta tagaagaaga agaagaaaag acgaggacga ctaggtcacg    6540
agaaagctaa ggcggtgaag caatagctaa taataaaatg acacgtgtat tgagcgttgt    6600
ttacacgcaa agttgttttt ggctaattgc cttatttta ggttgaggaa aagtatttgt     6660
gctttgagtt gataaacacg actcgtgtgt gccggctgca accactttga cgccgtttat    6720
tactgactcg tcgacaacca caatttctaa cggtcgtcat aagatccagc cgttgagatt    6780
taacgatcgt tacgatttat atttttttag cattatcgtt ttattttta aatatacggt     6840 ggagctgaaa attggcaata attgaaccgt gggtcccact gcattgaagc gtatttcgta    6900
ttttctagaa ttcttcgtgc tttatttctt ttcctttttg ttttttttg ccatttatct     6960 aatgcaagtg ggcttataaa atcagtgaat ttcttggaaa agtaacttct ttatcgtata    7020
acatattgtg aaattatcca tttctttaa ttttttagtg ttattggata tttttgtatg     7080
attattgatt tgcataggat aatgactttt gtatcaagtt ggtgaacaag tctcgttaaa    7140
aaaggcaagt ggtttggtga ctcgatttat tcttgttatt taattcatat atcaatggat    7200
cttatttggg gcctggtcca tatttaacac tcgtgttcag tccaatgacc aataatattt    7260
tttcattaat aacaatgtaa caagaatgat acacaaaaca ttctttgaat aagttcgcta    7320
tgaagaaggg aacttatccg gtcctagatc atcagttcat acaaacctcc atagagttca    7380
acatcttaaa caaggatatc ctgatccgtt gacggcgcgc cttcccgatc tagtaacata    7440
gatgacaccg cgcgcgataa tttatcctag tttgcgcgct atattttgtt ttctatcgcg    7500
tattaaatgt ataattgcgg gactctaatc ataaaaaccc atctcataaa taacgtcatg    7560
cattacatgt taattattac atgcttaacg taattcaaca gaaattatat gataatcatc    7620
gcaagaccgg caacaggatt caatcttaag aaactttatt gccaaatgtt tgaacgatcg    7680
gggaaattcg agctcaaagt gcaattgacc gatcagagtt tgaagaaaaa tttattacac    7740
actttatgta aagctgaaaa aaacggcctc ccgcagggaa gccgtttttt tcgttatctg    7800
atttttgtaa aggtctgata atggtccgtt gttttgtaaa tcagccagtc gcttgagtaa    7860
agaatccggt ctgaatttct gaagcctgat gtatagttaa tatccgctcc acgccatgtt    7920
cgtccgcttt tgcccgggag tttgccttcc ctgtttgaga agatgtctcc gccgatgctt    7980
ttccccggag cgacgtctgc aaggttccct tttgatgcca cccagccgag ggcttgtgct    8040
tctgattttg taatgtaatt atcaggtagc ttatgatatg tctgaagata atccgcaacc    8100
ccgtcaaacg tgttgataac ctgtgccatg atttgtacac aaaatttccg cgcacagatc    8160
ctcacagcgt atgcaaaaca aagctgcaac tactaatacc agtccaaaag caatgggcgc    8220
aacagcaaca gcaaaagctg caaccccttg tgctggttcg ttcctacagt tggacgcagc    8280
ccgagttctg agaaacaaat aaccacaagg caagttaggt accaaacccc ttaagctcaa    8340
cttaagcaaa tattcaaatc gtttgttttct acaaacaaat cttttcaga acggcttcag     8400 gtggggaata ttgtccattt aagtacctga aaatctaaga acacggccaa tccgggcgcc    8460
tttgcttgaa agtgggaaga aacctgaatg attgaacagt ggataagaga tttataagca    8520
```

```
agattagcag ggctgatcag attgttttt cgggtaggtt gatcaataca tatgcccctt    8580
ccctcttcct ttcctctaca atcgattgcc agggagagat agatatacca tcatgatgat    8640
gatggtgggg atggcgatga tggtaatgat gatgatccag cagaaaaaat tgcgcagaag    8700
aagaagatga gcggtcggtc ggtcgatagc ctttcagtcg gaggggaaag aacaaaataa    8760
tgcctatttg aaggcagatg gattgactaa gacgtgtgca ggcagtggag gagttacaag    8820
gcaggacata tttactaggt ataggtgtag gtaatagtaa tggagaggat aaatttaggt    8880
tttgggatga atggatttgt tggtacatgt tgcaactccc acactgcaat caaaggaccg    8940
ctatgacacc ccctgaatgc gacgcccatg agaatgccga ccccacatat acatttctgg    9000
aaataatagg gaaatgcacc cttgcattat atttcattta ttcgtcctcc attttgtgcg    9060
ctctccattc attttcaaat gcgctccact cttcctttat ttcttaccac cattatctcg    9120
tattcgaggt ccagaaatca agttgtgaat ctgccttggt tgcgcattgt taaagtactc    9180
ttctgtgtat atttctgccc caccgttttc acttccaaca cttaaatttt tttatttttt    9240
attttatata tttcttataa attgttggct tctcacacga acccaagcca tccaagcccc    9300
gacaaaggca atccaatgta cttgactaga gtcaaatacc ttttacttct ttacttctca    9360
tattacccag aagccaagcc aaccttacca aactaatgta cctgagcaga gtccactacc    9420
tttcctcaag tacagtggca gtcagagtat atcaccgctt gttatgtata tgctttaatg    9480
ctatgcttat ttctaggtca taatctaaat catatttgct gtcgagttta agcttatcga    9540
taccgtcgac ctcgagcttc ttcttgaatg ctcttatggg taggattatt tttcactttt    9600
ttccttcata ttccacacac atatatatat aaacacacta acattagtgg gaatatttgt    9660
ttgatatgtt tatttatttt acttcggggg tttttgtaac aattttgtag atctaatttc    9720
ttgttcttca tgtgtatatt aattttccct taagacttaa ataaaagag agagtttgtt    9780
atatatagat atatgaagtg agggaaatgg tacaaagtta aaggagatct gagtgagagt    9840
tagataataa atgaaaagaa ataagaaacc atcagggttt tttctaatgt ggagttttag    9900
attcagtttt gtagaactaa gattcacttt gttgggtgtt ctttcttcac tcatttctgt    9960
tattataata ataataaaat cttatatctt tctattttcc ttactaacaa gtacttgaag   10020
atttagatat atttatagat ctggtgttgt aataggtaaa aacttgattt ttatgactat   10080
aaaagtaagt tttgggaaac aaattgggga gagagtaagg aaggactatg aggtcatatc   10140
ttctgttttg tgatcatcca tcctccattg ttgttaatgt ctgtgtctct cttttttcttc   10200
tcttctttct cttactttcc tttccttatct ctagctctct ttctctctca tgaattatat   10260
catatcatat atttgataca aacacatgtg atggtaagtg agagtgaata aggtgaaact   10320
agctagattt ttgagttttc atgaaatttt aacttatatg agtgatagaa aataatggaa   10380
cttatacgta catgtaggac aatttagatg gttatctaag tttttgtttt tgttttctct   10440
tgagaatgtt aaatgttagt gttattttg tagtttggaa aaattatata tgagctaaga   10500
ttagtttaga agtggtcaaa agaaacatag atttgaaatt tcaactgaat tttcaagatt   10560
tcaaatagtc aatgaaacaa ggaggtaatt aagacaaatt agcttatggg gactcttttt   10620
tgttattcct taaaattact ctttttaaaa ttaaaaataa ctaatctcat ttcgaactac   10680
attactcaaa ctagtaatct ctaattcgac acgcaatttc caaatactta ttagtagaga   10740
gtcccacgtg attactttct tctccaccaa aacataaaac atgtcaagat taaatggtgt   10800
ttgaaaatta aaagatcaat tttcttaatc gtttacagtt gtcaactctc atgtcctgaa   10860
```

```
atatataatt ctcatgtcca aaacaagaaa agctaacaac gacttcaaat taaatcagtc    10920
aatcaaaatt agtcttcatt tacctactaa tttcttttta tatatccgat gggtactcta    10980
cgaaatcaga gtttcgtttc tttatttatt ttcttttata agattttga ggttttttca     11040 gaggttggaa ttgagcgcaa gattaggttt tgggtctgta agatttgttg tctttgttaa    11100
agaatctttg atcacgtcat cactcagata ttatttcttt ttattttca tttgtatttt     11160 tactaattta ttataaagtt ttgttagttt cagttcttga cttctgacaa gaaggtttta    11220
tgtcataatg aattaatttg taacctattt ataaattcaa aaatgtcatc atattactac    11280
ttttgaccat ttaatattag atttctcatt tggtcaatac ccaatgttca tattacatat    11340
atagagacaa aaattataag gatactaaat tgttcatatt tcttggaagt aaaaagatta    11400
atgatcactg aataaataga tttggcatag aagtatagca ttggaattgc ttcaacatct    11460
ttggtgtaga tagatttatg caatttctct ttcttttga agtatctttt tttttctaga     11520
gagagaataa tgttagggat ttttatcatt ttctctctca ttatgggtac tgagaggaaa    11580
gtgagatttt tagtacggat ccaatagttt aagagtttgg tctgccttct acgatccaaa    11640
aaaatctacg gtcatgatct ctccatcgag aaggttgaga gttcagacat caaagtctat    11700
aatatgtcat tgtaatacgt atttgtgcat atatatctat gtacaagtac atatacagga    11760
aactcaagaa aaaagaataa atggtaaatt taattatatt ccaataagg aaagtatgga     11820 acgttgtgat gttactcgga caagtcattt agttacatcc atcacgttta aatttaatcc    11880
aatggttaca attttaatac tatcaaatgt ctattggatt tatacccaat gtgttaatgg    11940
gttgttgaca catgtcacat gtctgaaacc ctagacatgt tcagaccaat catgtcactc    12000
taattttgcc agcatggcag ttggcagcca atcactagct cgataaattt aaggtttcag    12060 aggaattttta atttatttag ggttcatatt gtttcataaa atgattcttt atttgttaca    12120
actttaagga aatattttat taactattta attgttccct tttcttatat tactttgtt    12180 ttttcttcac atcatgtgtc acattaagtt gcatttcttc tgactcaaaa gaaccgatgt    12240
ttgcttttaa ggtttcgtat tagaatcact taactgtgca agtggtcgat ttgaccctat    12300
caagcttgat atcgaattgc ggccgcattt gggctcctgc aggtaccta attaaaagtt     12360 taaactatca gtgtttgaca ggatatattg gcgggtaaac ctaagagaaa agagcgttta    12420
ttagaataat cggatattta aaagggcgtg aaaaggttta tccgttcgtc catttgtatg    12480
tgcatgccaa ccacagggtt ccccagatc                                      12509

<210> SEQ ID NO 64
<211> LENGTH: 597
<212> TYPE: DNA
<213> ORGANISM: Arabidopsis thaliana

<400> SEQUENCE: 64
tgccaagaat gtaagttttt atttcttta tatgttcaaa cagttttata aagtactata       60
agcttttttt agccaaaaga aatatcttaa gttttagtaa ccaataaaga attattgcgg     120
cctccttatt taattatagt acatatgtca tagtagatgt ttttttttatt attattattt    180 tttattttt tatagttttt tacaaattcg acttggagac cttatgattt ggaagatact     240
ccatttaatt ttatgagttg tgtttgaaaa catatttaa gactaaacac gtagagaaca     300
ttcttaacaa atttgtaaat aaataaattt aactctattc tctaggattt aaatattata    360
ggtatatata taattttcta ataagtttat atcgagtcac tcatacgagt tgtgtagaaa    420
gttaatcacg ggtaccaatt ttaaattaaa aataagaata attatatgat cttaaattta    480
```

```
tacaactctg ataaaagatt gggctttgac atctttgaag aaaactagat ttagtaatat    540
tctgattaaa ttgggttcac actttgtagt gggcacactt tccgggttcg aaatcga      597

<210> SEQ ID NO 65
<211> LENGTH: 2043
<212> TYPE: DNA
<213> ORGANISM: Eucalyptus grandis

<400> SEQUENCE: 65
gcgccaccac caaacgctca ccttctcatc atcagccctc tgtctctgtc tctgtctctc    60
gattctccgc cccgccacga caatggaggc gaagccgtcg gagcagcccc gcgagttcat   120
cttccggtcg aagctccccg acatctacat tcccgacaac ctctccctcc acgcctactg   180
cttcgagaac atctccgagt tcgccgaccg ccctgcgtc atcaacgggg ccaccggccg    240
gacctacacc tatgccgagg tcgagctgat ctcccgccgg gtctcagccg gcctcaacgg   300
gctcggcgtc ggacagggcg acgtgatcat gctgctcctc cagaactgcc ctgagttcgt   360
gttcgcgttc ctcggcgcgt cctaccgggg cgccatcagc acgaccgcga accgttcta    420 caccccgggc gagatcgcca agcaggcctc agctgcccgg gccaagatcg tgatcacgca   480
ggccgcgttc gccgacaagg tgaggccgtt cgcggaggag aacggggtga aggtcgtgtg   540
catcgatacc gcgccggagg gctgcctgca cttctcggaa ttgatgcagg cggacgagaa   600
cgccgccccc gcggcggacg tcaagccgga cgacgtcttg gcgctcccct attcgtcggg   660
cacgacgggg cttcccaagg gagtgatgct tacgcacagg ggtcaagtga ccagcgtggc   720
gcagcaggtc gacggagaca accccaactt gtacttccac aaggaggacg tgatcctgtg   780
cacgctcccg ttgttccaca tatactccct caactcggtg atgttctgcg cgctccgtgt   840
cggcgccgcc atcctgatca tgcagaagtt cgagatcgtg cgctgatgg agctcgtgca    900 gcggtaccgg gtgacgatcc tgcccattgt cccgccgatc gtgctggaga tcgccaagag   960
cgccgaggtg gaccggtacg acctgtcgtc gatccggacc atcatgtcgg gtgcggcccc   1020
gatggggaag gagctcgagg acaccgtgcg agccaagctg cccaatgcca agctcggaca   1080
gggctatggg atgacggagg cgggcccggt gctggcaatg tgcccggcat ttgcaaagga   1140
gccgttcgag atcaagtcag gcgcatgcgg gaccgtcgtg aggaacgcgg agatgaagat   1200
cgtcgacccg gagacagggg cctcgctccc gcggaaccag gccggcgaga tctgcatccg   1260
gggtcaccag atcatgaaag gttatctgaa cgacgccgag gcgaccgcaa ataccataga   1320
caaagaaggg tggctgcaca ccggcgacat cggctacata gacgatgacg acgagctctt   1380
cattgtcgat cggttgaagg aactcatcaa gtacaagggc ttccaggttg ctccggccga   1440
gctagaggca atgctgattg cacacccaag tatctcggat gccgctgttg tgccgatgaa   1500
ggatgaggtt gccggtgagg ttcctgttgc attcgtggtg aaatccaatg gttccgtaat   1560
caccgaggac gaaatcaagc aatacatctc gaagcaggtc gtgttttaca agaggatcaa   1620
gcgggttttc ttcacggacg caattccgaa agccccctcc ggaaaaatct tgaggaagga   1680
cctaagagca aagttggcct ctggtgttta caattaattt ctcatacccct tttctttttc   1740 aacctgccc ctgtacttgc ttaaagaccc atgtagttga aatgaatgta acctcttcgg    1800
aggggccaaa tatggaaggg ggaaagaaag acatatggcg atgatttgat ttcacatgct   1860
attgtaatgt atttattgtt tcaattccga attagacaaa gtgcttaaag ctctcttttc   1920
ggattttttt tttcattaat gtataataat tgcggacatt acaatatact gtacaacgtg   1980
```

```
atttgagctt gatgaattac aagattggaa gaacttcgaa gacaaaaaaa aaaaaaaaaa    2040
aaa                                                                  2043

<210> SEQ ID NO 66
<211> LENGTH: 2005
<212> TYPE: DNA
<213> ORGANISM: Pinus radiata

<400> SEQUENCE: 66
attcaattct tcccactgca ggctacattt gtcagacacg tttccgcca ttttcgcct        60 gtttctgcgg agaatttgat caggttcgga ttgggattga atcaattgaa aggtttttat    120
tttcagtatt tcgatcgcca tggccaacgg aatcaagaag gtcgagcatc tgtacagatc    180
gaagcttccc gatatcgaga tctccgacca tctgcctctt cattcgtatt gctttgagag    240
agtagcggaa ttcgcagaca gaccctgtct gatcgatggg gcgacagaca gaacttattg    300
cttttcagag gtggaactga tttctcgcaa ggtcgctgcc ggtctggcga agctcgggtt    360
gcagcagggg caggttgtca tgcttctcct tccgaattgc atcgaatttg cgtttgtgtt    420
catgggggcc tctgtccggg gcgccattgt gaccacggcc aatcctttct acaagccggg    480
cgagatcgcc aaacaggcca aggccgcggg cgcgcgcatc atagttaccc tggcagctta    540
tgttgagaaa ctggccgatc tgcagagcca cgatgtgctc gtcatcacaa tcgatgatgc    600
tcccaaggaa ggttgccaac atatttccgt tctgaccgaa gccgacgaaa cccaatgccc    660
ggccgtgaca atccacccgg acgatgtcgt ggcgttgccc tattcttccg gaaccacggg    720
gctccccaag ggcgtgatgt taacgcacaa aggcctggtg tccagcgttg cccagcaggt    780
cgatggtgaa aatcccaatc tgtatttcca ttccgatgac gtgatactct gtgtcttgcc    840
tcttttccac atctattctc tcaattcggt tctcctctgc gcgctcagag ccggggctgc    900
gaccctgatt atgcagaaat tcaacctcac gacctgtctg gagctgattc agaaatacaa    960
ggttaccgtt gccccaattg tgcctccaat tgtcctggac atcacaaaga gcccatcgt    1020 ttcccagtac gatgtctcgt ccgtccggat aatcatgtcc ggcgctgcgc tctcgggaa    1080 ggaactcgaa gatgccctca gagagcgttt tcccaaggcc attttcgggc agggctacgg    1140
catgacagaa gcaggcccgg tgctggcaat gaacctagcc ttcgcaaaga tccttttccc    1200
cgtcaaatct ggctcctgcg aacagtcgt ccggaacgct caaataaaga tcctcgatac    1260
agaaactggc gagtctctcc cgcacaatca agccggcgaa atctgcatcc gcggacccga    1320
aataatgaaa ggatatatta acgacccgga atccacggcc gctacaatcg atgaagaagg    1380
ctggctccac acaggcgacg tcgggtacat tgacgatgac gaagaaatct tcatagtcga    1440
cagagtaaag gagattatca aatataaggg cttccaggtg gctcctgctg agctggaagc    1500
tttacttgtt gctcatccgt caatcgctga cgcagcagtc gttcctcaaa agcacgagga    1560
ggcgggcgag gttccggtgg cgttcgtggt gaagtcgtcg gaaatcagcg agcaggaaat    1620
caaggaattc gtggcaaagc aggtgatttt ctacaagaaa atacacagag tttactttgt    1680
ggatgcgatt cctaagtcgc cgtccggcaa gattctgaga aaggatttga gaagcagact    1740
ggcagcaaaa tgaaatgaa tttccatatg attctaagat tcctttgccg ataattatag    1800
gattcctttc tgttcacttc tatttatata ataaagtggt gcagagtaag cgccctataa    1860
ggagagagag agcttatcaa ttgtatcata tggattgtca acgccctaca ctcttgcgat    1920 cgcttttcaat atgcatatta ctataaacga tatatgttt ttttataaat ttactgcact    1980
tctcgttcaa aaaaaaaaa aaaaa                                          2005
```

<210> SEQ ID NO 67
<211> LENGTH: 372
<212> TYPE: DNA
<213> ORGANISM: Pinus radiata

<400> SEQUENCE: 67

```
atccttgggc agggatacgg catgacagaa gcaggcccgg tgctggcaat gaacctagcc      60
ttcgcaaaga atcctttccc cgtcaaatct ggctcctgcg aacagtcgt ccggaacgct      120 caaataaaga tcctcgatac agaaactggc gagtctctcc cgcacaatca agccggcgaa     180
atctgcatcc gcggacccga ataatgaaa ggatatatta acgacccgga atccacggcc      240
gctacaatcg atgaagaagg ctggctccac acaggcgacg tcgggtacat tgacgatgac     300
gaagaaatct tcatagtcga cagagtaaag gagattatca atataaaggc ttccaggtgg     360
atcctgctaa tc                                                          372
```

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 68

```
gaagaaagcc gaaataaaga gg                                                22
```

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 69

```
ttgaacgtat agtcgccgat ag                                                22
```

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 70

```
aaggagatat aacaatgatt gaacaagatg gattgc                                 36
```

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 71

```
tcagaagaac tcgtcaagaa gg                                                22
```

<210> SEQ ID NO 72
<211> LENGTH: 22
<212> TYPE: DNA

<213> ORGANISM: Artificial Sequence
<220> FEATURE:
<223> OTHER INFORMATION: Description of Artificial Sequence: Synthetic primer

<400> SEQUENCE: 72
cgaaaacggc aagaaaaagc ag                                           22

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
acgaccaaag ccagtaaagt ag                                           22

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
aatgggaagc ctgagtttac a                                            21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
ggccagcatg ttttcctcca g                                            21

<210> SEQ ID NO 76
<211> LENGTH: 2064
<212> TYPE: DNA
<213> ORGANISM: Pinus radiata

<400> SEQUENCE: 76 aaaaccctc acaaatacat aaaaaaaatt ctttatttaa ttatcaaact ctccactacc    60
tttcccacca accgttacaa tcctgaatgt tggaaaaaac taactacatt gatataaaaa   120
aactacatta cttcctaaat catatcaaaa ttgtataaat atatccactc aaaggagtct   180
agaagatcca cttggacaaa ttgcccatag ttggaaagat gttcaccaag tcaacaagat   240
ttatcaatgg aaaaatccat ctaccaaact tactttcaag aaaatccaag gattatagag   300
taaaaaatct atgtattatt aagtcaaaaa gaaaaccaaa gtgaacaaat attgatgtac   360
aagtttgaga ggataagaca ttggaatcgt ctaaccagga ggcggaggaa ttccctagac   420
agttaaaagt ggccggaatc ccggtaaaaa agattaaaat ttttttgtag agggagtgct   480
tgaatcatgt tttttatgat ggaaatagat tcagcaccat caaaaacatt caggacacct   540
aaaattttga agtttaacaa aaataacttg gatctacaaa aatccgtatc ggattttctc   600
taaatataac tagaattttc ataacttttca aagcaactcc tcccctaacc gtaaaacttt   660
tcctacttca ccgttaatta cattccttaa gagtagataa agaaataaag taaataaaag   720

```
tattcacaaa ccaacaattt atttcttta tttacttaaa aaaacaaaaa gtttatttat      780
tttacttaaa tggcataatg acatatcgga gatccctcga acgagaatct tttatctccc     840
tggttttgta ttaaaaagta atttattgtg gggtccacgc ggagttggaa tcctacagac     900
gcgctttaca tacgtctcga gaagcgtgac ggatgtgcga ccggatgacc ctgtataacc     960
caccgacaca gccagcgcac agtatacacg tgtcatttct ctattggaaa atgtcgttgt    1020
tatccccgct ggtacgcaac caccgatggt gacaggtcgt ctgttgtcgt gtcgcgtagc    1080
gggagaaggg tctcatccaa cgctattaaa tactcgcctt caccgcgtta cttctcatct    1140
tttctcttgc gttgtataat cagtgcgata ttctcagaga gcttttcatt caaaggtatg    1200
gagttttgaa gggctttact cttaacattt gttttttcttt gtaaattgtt aatggtggtt   1260
tctgtggggg aagaatcttt tgccaggtcc ttttgggttt cgcatgttta tttgggttat   1320
ttttctcgac tatggctgac attactaggg ctttcgtgct ttcatctgtg ttttcttccc    1380
ttaataggtc tgtctctctg gaatatttaa ttttcgtatg taagttatga gtagtcgctg    1440
tttgtaatag gctcttgtct gtaaaggttt cagcaggtgt ttgcgtttta ttgcgtcatg    1500
tgtttcagaa ggccttttgca gattattgcg ttgtacttta atattttgtc tccaaccttg   1560
ttatagtttc cctcctttga tctcacagga accctttctt ctttgagcat tttcttgtgg    1620
cgttctgtag taatatttta atttttgggcc cgggttctga gggtaggtga ttattccagt   1680
gatgtgcttt ccctataagg tcctctatgt gtaagctgtt agggtttgtg cgttactatt   1740
gacatgtcac atgtcacata ttttcttcct cttatccttc gaactgatgg ttcttttttct  1800 aattcgtgga ttgctggtgc catattttat ttctattgca actgtatttt agggtgtctc    1860 tttcttttttg atttcttgtt aatatttgtg ttcaggttgt aactatgggt tgctagggtg   1920
tctgccctct tcttttgtgc ttcttcgca gaatctgtcc gttggtctgt atttgggtga    1980
tgaattattt attccttgaa gtatctgtct aattagcttg tgatgatgtg caggtatatt    2040
cgttagtcat atttcaattt caag                                           2064
```

<210> SEQ ID NO 77
<211> LENGTH: 2251
<212> TYPE: DNA
<213> ORGANISM: Pinus taeda

<400> SEQUENCE: 77

```
ggccgggtgg tgacatttat tcataaattc atctcaaaac aagaaggatt tacaaaaata     60
aaagaaaaca aaattttcat ctttaacata attataattg tgttcacaaa attcaaactt    120
aaacccttaa tataaagaat ttctttcaac aatacacttt aatcacaact tcttcaatca    180
caacctcctc caacaaaatt aaaatagatt aataaataaa taaacttaac tatttaaaaa    240 aaatattat acaaaattta ttaaaacttc aaaataaaca aactttttat acaaaattca     300
tcaaaacttt aaaataaagc taaacactga aaatgtgagt acatttaaaa ggacgctgat    360
cacaaaaatt ttgaaaacat aaacaaactt gaaactctac cttttaagaa tgagtttgtc    420
gtctcattaa ctcattagtt ttatagttcg aatccaatta acgtatcttt tatttttatgg   480 aataagggtg ttttaataag tgattttggg attttttttag taatttattt gtgatatgtt   540
atggagtttt taaaatata tatatatata tatattttg ggttgagttt acttaaaatt     600
tggaaaaggt tggtaagaac tataaattga gttgtgaatg agtgttttat ggattttta    660 agatgttaaa tttatatatg taattaaaat tttatttga ataacaaaaa ttataattgg    720
```

-continued

```
ataaaaaatt gttttgttaa atttagagta aaaatttcaa aatctaaaat aattaaacac    780
tattattttt aaaaaatttg ttggtaaatt ttatcttata tttaagttaa aatttagaaa    840
aaattaattt taaattaata aacttttgaa gtcaaatatt ccaaatattt tccaaaatat    900
taaatctatt ttgcattcaa aatacaattt aaataataaa acttcatgga atagattaac    960
caatttgtat aaaaaccaaa aatctcaaat aaaatttaaa ttacaaaaca ttatcaacat   1020
tatgatttca agaaagacaa taaccagttt ccaataaaat aaaaaacctc atggcccgta   1080
attaagatct cattaattaa ttcttatttt ttaattttt tacatagaaa atatctttat    1140
attgtatcca agaaatatag aatgttctcg tccagggact attaatctcc aaacaagttt   1200
caaaatcatt acattaaagc tcatcatgtc atttgtggat tggaaattat attgtataag   1260
agaaatatag aatgttctcg tctagggact attaatttcc aaacaaattt caaaatcatt   1320
acattaaagc tcatcatgtc atttgtggat tggaaattag acaaaaaaaa tcccaaatat   1380
ttctctcaat ctcccaaaat atagttcgaa ctccatattt ttggaaattg agaattttt    1440 tacccaataa tatattttt tatacatttt agagattttc cagacatatt tgctctggga    1500
tttattggaa tgaaggttga gttataaact ttcagtaatc caagtatctt cggttttga    1560 agatactaaa tccattatat aataaaaaca cattttaaac accaatttaa tgggatttca   1620
gatttgtatc ccatgctatt ggctaaggca tttttcttat tgtaatctaa ccaattctaa   1680
tttccaccct ggtgtgaact gactgacaaa tgcggtccga aaacagcgaa tgaaatgtct   1740
gggtgatcgg tcaaacaagc ggtgggcgag agagcgcggg tgttggccta gccgggatgg   1800
gggtaggtag acggcgtatt accggcgagt tgtccgaatg gagttttcgg ggtaggtagt   1860
aacgtagacg tcaatggaaa aagtcataat ctccgtcaaa aatccaaccg ctccttcaca   1920
tcgcagagtt ggtggccacg ggaccctcca cccactcact cgatcgcctg ccgtggttgc   1980
ccattattca accatacgcc acttgactct tcaccaacaa ttccaggccg gctttctata   2040
caatgtactg cacaggaaaa tccaatataa aaagccggcc tctgcttcct tctcagtagc   2100
ccccagctca ttcaattctt cccactgcag gctacatttg tcagacacgt tttccgccat   2160
ttttcgcctg tttctgcgga gaatttgatc aggttcggat tgggattgaa tcaattgaaa   2220
ggtttttatt ttcagtattt cgatcgccat g                                  2251
```